(12) United States Patent
Ajellal et al.

(10) Patent No.: US 11,352,376 B2
(45) Date of Patent: Jun. 7, 2022

(54) CATALYSTS

(71) Applicant: BOREALIS AG, Vienna (AT)

(72) Inventors: Noureddine Ajellal, Helsinki (FI); Luigi Resconi, Neuhofen an der Krems (AT); Vyatcheslav V. Izmer, Moscow (RU); Dmitry S. Kononovich, Moscow (RU); Alexander Z. Voskoboynikov, Moscow (RU); Ville Virkkunen, Helsinki (FI)

(73) Assignee: BOREALIS AG, Vienna (AT)

( * ) Notice: Subject to any disclaimer, the term of this patent is extended or adjusted under 35 U.S.C. 154(b) by 242 days.

(21) Appl. No.: 16/461,517

(22) PCT Filed: Nov. 17, 2017

(86) PCT No.: PCT/EP2017/079662
§ 371 (c)(1),
(2) Date: May 16, 2019

(87) PCT Pub. No.: WO2018/091684
PCT Pub. Date: May 24, 2018

(65) Prior Publication Data
US 2019/0308995 A1 Oct. 10, 2019

(30) Foreign Application Priority Data

Nov. 18, 2016 (EP) .................... 16199646

(51) Int. Cl.
*C07F 17/00* (2006.01)
*C08F 4/6592* (2006.01)
(Continued)

(52) U.S. Cl.
CPC ............... *C07F 7/081* (2013.01); *C07C 1/20* (2013.01); *C07C 13/32* (2013.01); *C07C 41/00* (2013.01);
(Continued)

(58) Field of Classification Search
CPC ..... C07F 17/00; C08F 4/65927; C08F 210/16
See application file for complete search history.

(56) References Cited

U.S. PATENT DOCUMENTS

| | | | |
|---|---|---|---|
| 6,057,408 A | 5/2000 | Winter et al. |
| 6,252,019 B1 | 6/2001 | Ewen et al. |
| 10,167,355 B2 | 1/2019 | Ajellal et al. |
| 10,301,411 B2 | 5/2019 | Ajellal et al. |
| 2005/0288461 A1 | 12/2005 | Jensen et al. |

(Continued)

FOREIGN PATENT DOCUMENTS

| | | |
|---|---|---|
| EP | 1858907 B1 | 10/2008 |
| EP | 2532687 A2 | 12/2012 |

(Continued)

OTHER PUBLICATIONS

Cheng. Carbon-$^{13}$NMR analysis of ethylene-propylene rubbers, Macromolecules, 1984, 17, 1950-1955.

(Continued)

*Primary Examiner* — Caixia Lu
(74) *Attorney, Agent, or Firm* — Meunier Carlin & Curfman LLC

(57) ABSTRACT

A complex of formula (I)

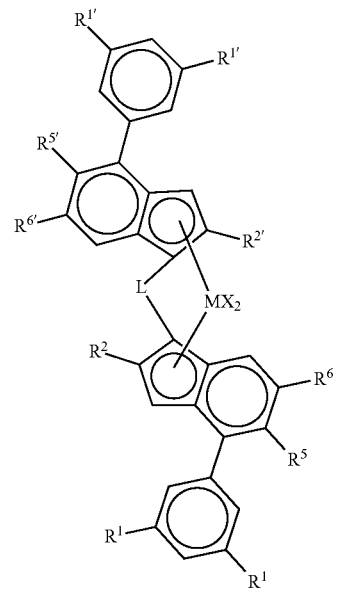

wherein

M is zirconium or hafnium;

each X independently is a sigma ligand; L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom or a $C_1$-$C_{20}$-hydrocarbyl group optionally containing one or more silicon atoms or heteroatoms of Group 14-16 of the periodic table or fluorine atoms, and optionally two R' groups taken together can form a ring;

$R^2$ and $R^{2'}$ are each independently a $C_1$-$C_{20}$ hydrocarbyl group, —$OC_{1-20}$ hydrocarbyl group or —$SC_{1-20}$ hydrocarbyl group;

$R^5$ is a —$OC_{1-20}$ hydrocarbyl group or —$SC_{1-20}$ hydrocarbyl group, said $R^5$ group being optionally substituted by one or more halo groups;

$R^{5'}$ is hydrogen or a $C_{1-20}$ hydrocarbyl group; —$OC_{1-20}$ hydrocarbyl group or —$SC_{1-20}$ hydrocarbyl group; said $C_{1-20}$ hydrocarbyl group being optionally substituted by one or more halo groups;

$R^6$ and $R^{6'}$ are each independently a $C_{1-20}$ hydrocarbyl group; —$OC_{1-20}$ hydrocarbyl group or —$SC_{1-20}$ hydrocarbyl group;

each $R^1$ and $R^{1'}$ are independently —$CH_2R^x$ wherein $R^x$ are each independently H, or a $C_{1-20}$ hydrocarbyl group, optionally containing heteroatoms.

16 Claims, No Drawings

(51) Int. Cl.

| | | |
|---|---|---|
| C08F 110/06 | (2006.01) | |
| C07F 7/08 | (2006.01) | |
| C07C 1/20 | (2006.01) | |
| C07C 13/32 | (2006.01) | |
| C07C 41/00 | (2006.01) | |
| C07C 45/68 | (2006.01) | |
| C07C 49/443 | (2006.01) | |
| C08F 4/649 | (2006.01) | |
| C08F 10/06 | (2006.01) | |
| C07C 41/18 | (2006.01) | |
| C08F 4/659 | (2006.01) | |

(52) U.S. Cl.
CPC .............. *C07C 41/18* (2013.01); *C07C 45/68* (2013.01); *C07C 49/443* (2013.01); *C08F 4/6498* (2013.01); *C08F 4/65927* (2013.01); *C08F 10/06* (2013.01); *C07C 2602/08* (2017.05); *C08F 4/65908* (2013.01); *C08F 4/65912* (2013.01); *C08F 4/65916* (2013.01)

(56) References Cited

U.S. PATENT DOCUMENTS

| | | |
|---|---|---|
| 2008/0081887 A1 | 4/2008 | Wang et al. |
| 2014/0206819 A1 | 7/2014 | Hafner et al. |
| 2016/0009838 A1 | 1/2016 | Itagaki et al. |
| 2017/0037164 A1 | 2/2017 | Ajellal et al. |
| 2017/0037165 A1 | 2/2017 | Ajellal et al. |
| 2017/0342175 A1 | 11/2017 | Hagadorn et al. |
| 2019/0308995 A1 | 10/2019 | Ajellal et al. |

FOREIGN PATENT DOCUMENTS

| | | |
|---|---|---|
| EP | 2657285 A1 | 10/2013 |
| EP | 2722346 A1 | 4/2014 |
| EP | 2933277 A1 | 10/2015 |
| EP | 2729529 B1 | 4/2016 |
| EP | 1548018 B1 | 10/2018 |
| EP | 2511305 B1 | 5/2019 |
| EP | 2813517 B2 | 6/2019 |
| JP | 2014193846 A | 10/2014 |
| WO | 94014856 A1 | 7/1994 |
| WO | 95012622 A1 | 5/1995 |
| WO | 9714727 A1 | 4/1997 |
| WO | 98040331 A1 | 9/1998 |
| WO | 0009515 A1 | 2/2000 |
| WO | 00024792 A1 | 5/2000 |
| WO | 00024793 A1 | 5/2000 |
| WO | 02002576 A1 | 1/2002 |
| WO | 03049856 A1 | 6/2003 |
| WO | 03051934 A2 | 6/2003 |
| WO | 2003050131 A1 | 6/2003 |
| WO | 03102042 A1 | 12/2003 |
| WO | 2006069733 A1 | 7/2006 |
| WO | 2006097497 A1 | 9/2006 |
| WO | 2006100258 A1 | 9/2006 |
| WO | 2007116034 A1 | 10/2007 |
| WO | 2007122098 A1 | 11/2007 |
| WO | 2009054831 A1 | 4/2009 |
| WO | 2010052260 A1 | 5/2010 |
| WO | 2010052263 A1 | 5/2010 |
| WO | 2010052264 A1 | 5/2010 |
| WO | 2011076443 A1 | 6/2011 |
| WO | 2011076780 A1 | 6/2011 |
| WO | 2011135004 A2 | 11/2011 |
| WO | 2011135005 A2 | 11/2011 |
| WO | 2012001051 A1 | 1/2012 |
| WO | 2012001052 A2 | 1/2012 |
| WO | 2012075560 A1 | 6/2012 |
| WO | 2012084961 A1 | 6/2012 |
| WO | 2013007650 A1 | 1/2013 |
| WO | 2014096171 A1 | 6/2014 |
| WO | 2015011135 A1 | 1/2015 |
| WO | 2015158790 A1 | 10/2015 |
| WO | 2015158791 A2 | 10/2015 |
| WO | 2016038210 A1 | 3/2016 |
| WO | 2016038211 A1 | 3/2016 |
| WO | 2018108917 A1 | 6/2018 |
| WO | 2018108918 A1 | 6/2018 |
| WO | 2018122134 A1 | 7/2018 |
| WO | 2019002345 A1 | 1/2019 |
| WO | 2019052820 A1 | 3/2019 |
| WO | 2019179959 A1 | 9/2019 |

OTHER PUBLICATIONS

Gahleitner et al. Crystallinity and mechanical properties of PP-homopolymers as influenced by molecular structure and nucleation, Journal of Applied Polymer Science, 1996, 61(4), 649-657.

Grein et al. Impact modified isotactic polypropylene with controlled rubber intrinsic viscosities: Some new aspects about morphology and fracture, Journal of Applied Polymer Science, 2003, 87(10), 1702-1712.

Kuklin et al. Quantitative structure-property relationships in propene polymerization by zirconocenes with a rac-SiMe$_2$[Ind]$_2$ based ligand frameworks, Journal of Molecular Catalysis A: Chemical, 2016, 412, 39-46.

Premphet et al. Polypropylene/metallocene ethylene-octene copolymer blends with a bimodal particle size distribution: Mechanical properties and their controlling factors, Journal of Applied Polymer Science, 2002, 85(11), 2412-2418.

Singh et al. Triad sequence determination of ethylene-propylene copolymers—application of quantitative $^{13}$C NMR, Polymer Testing, 2009, 28(5), 475.

Wang et al. Structural Analysis of Ethylene/Propylene Copolymers Synthesized with a Constrained Geometry Catalyst, Macromolecules, 2000, 33(4), 1157-1162.

Del Hierro et al. "Soluble Fraction analysis in propylene", The Column, Feb. 2014, 18-23.

Endres, et al., "Die fluorige Phase: Organische Chemie mit hochfluorierten Reagenzien und Lösungsmitteln", Chemie in unserer Zeit, 2000, 34(6), 382-393.

Ewen, et al., "Crystal structures and stereospecific propylene polymerizations with chiral hafnium metallocene catalysts", JACS, 1987, 109, 6544-6545.

Lo Nostro, "Phase separation properties of fluorocarbons, hydrocarbons and their copolymers", Advances in Colloid and Interface Science, 1995, 56, 245-287.

Busico et al. Microstructure of polypropylene, Process in Polymer Science, 2001, 26(3), 443-533.

Busico et al. Full Assignment of the $^{13}$C NMR Spectra of Regioregular Polypropylenes: Methyl and Methylene Region, Macromolecules 1997, 30(20), 6251-6263.

Busico et al., Alk-1-ene Polymerization in the Presence of a Monocyclopentadienyl Zirconium(IV) Actamidinate Catalyst: Microstructural and Mechanistic Insights, Macromol. Rapid Commun, vol. 28, 2007, pp. 1128-1134.

Castignolles et al., Detection and quantification of branching in polyacrylates by size-exclusion chromatography (SEC) and melt-state $^{13}$C NMR spectroscopy, Polymer 50 (2009) 2373-83.

Chukanova, et al., "Polymerization of propylene using isospecific rac-Me2Si(2-Me,4-PhInd)2ZrCl2 catalyst immobilized on polyethylene with grafted poly(acrylic acid)", Polymer science. Series A, Chemistry, physics 43.8 (2001): 787-792.

Ewen, et al., "Evaluation of the dimethylsilyl-bis(2-methyl-4-phenyl-1-indenyl) ligand with group 4 triad metals in propene polymerizations with methylaluminoxane", Macromolecular Rapid Communications vol. 19, Issue 1, Jan. 1998, pp. 71-73.

Filip, et al., "Heteronuclear decoupling under fast MAS by a rotor-synchronized Hahn-echo pulse train", Journal of Magnetic Resonance, vol. 176, Issue 2, Oct. 2005, pp. 239-243.

Griffin, et al., "Low-load rotor-synchronised Hahn-echo pulse train (RS-HEPT) 1H decoupling in solid-state NMR: factors affecting MAS spin-echo dephasing times.", Mag. Res. in Chem. 2007 45, S1, S198.

(56) References Cited

OTHER PUBLICATIONS

Hasegawa et al. High-temperature ethylene/alpha-olefin copolymerization with a zirconene catalyst: Effects of the zirconene ligand and polymerization conditions on copolymerization behavior, Journal of Polymer Science: Part A; Polymer Chemistry, 2000, 38, 4641-4648.

Hintermann, et al., Beilstein J. Org. Chem. 2007, 3, 1-5.

Klimke, et al., "Optimisation and Application of Polyolefin Branch Quantification by Melt-State 13C NMR Spectroscopy", Macromolecular Chemistry and Physics vol. 207, Issue Feb. 24, 2006 pp. 382-395.

Liu, et al., "Poly(ethylene-co-1-octene) Characterization by High-Temperature Multidimensional NMR at 750 MHz", Macromolecules 2001, 34, 4757-4767.

Matsubara, et al., "Synthesis and Structures of Nickel Halide Complexes Bearing Mono- and Bis-coordinated N-Heterocyclic Carbene Ligands, Catalyzing Grignard Cross-Coupling Reactions", Organometallics, 2006, 25 (14), pp. 3422-3427.

Parkinson, et al., "Effect of Branch Length on 13C NMR Relaxation Properties in Molten Poly[ethylene-co-($\alpha$-olefin)] Model Systems", Macromol. Chem. Phys. 2007;208:2128-2133.

Parkinson, et al., "NMR Spectroscopy of Polymers: Innovative Strategies for Complex Macromolecules, Chapter 24, 401 (2011)".

Pollard, "Observation of Chain Branching in Polyethylene in the Solid State and Melt via 13C NMR Spectroscopy and Melt NMR Relaxation Time Measurements", Macromolecules, 2004, 37 (3), pp. 813-825.

Qui, et al., "Improved Peak Assignments for the 13C NMR Spectra of Poly(ethylene-co-1-octene)s", Macromolecules 2007, 40, 6879-6884.

Randall, A Review of high resolution liquid $^{13}$Carbon nuclear magnetic resonance characterizations of ethylene-based polymers, Journal of Macromolecular Science, Reviews in Macromolecular Chemistry and Physics, 1989, C29, 201-317.

Resconi et al. Selectivity in Propene Polymerization with Metallocene Catalysts, Chemical Reviews, 2000, 100, 1253-1346.

Song et al. Synthesis of aryl-substituted indanones and indenes via a highly efficient ligand-free palladium-catalyzed Suzuki coupling process, Arkiovic, 2016, 4, 306-327.

Stork, et al., "The Stereochemistry of the SN2' Reaction. I. Preparation of Pure trans-6-Alkyl-2-cyclohexen-1-ols", J. Am. Chem. Soc. 1956, 78, 4604-4608.

Tynys et al. Propylene polymerisations with novel heterogeneous combination metallocene catalyst systems, Polymer, 2007, 48, 1893-1902.

Ushakova, et al., Ethylene polymerization and ethylene-1-hexene copolymerization over immobilized metallocene catalysts, Kinetics and Catalysis, Feb. 2012, vol. 53, Issue 1, pp. 75-83.

Wang, et al., "Long Chain Branching in Ethylene Polymerization Using Binary Homogeneous Metallocene Catalyst System", Polymer Reaction Engineering, vol. 7, 1999—Issue 3, pp. 327-346.

Zhou, et al., "A new decoupling method for accurate quantification of polyethylene copolymer composition and triad sequence distribution with 13C NMR.", J Magn Reson. Aug. 2007;187(2):225-33. Epub May 23, 2007.

International Search Report and Written Opinion dated Feb. 2, 2018 in International Application No. PCT/EP2017/079662 (13 pages).

Hopf et al. Highly syndiotactic polypropene with $C_s$-symmetric metallocene/MAO catalysts. Catalysis Communications, 2002, 2, 459.

Kaminsky et al. Polymerization of Ethene and Longer Chained Olefins by Metallocene Catalysis, Macromol Symp 2005, 226, 25.

Kim et al. Ethylene/1-Hexene Copolymerizations of Syndioselective Metallocenes: Direct Comparison of $Me_2C(Cp)(Flu)ZrMe_2$ with $Et(Cp)(Flu)ZrMe_2$, J Polym Sci Part A Polym Chem, 1999, 37, 2763.

Stadler et al. Influence of Type and Content of Various Comonomers on Long-Chain Branching of Ethene/alpha-olefin Copolymers, Macromolecules, 2006, 39, 1474.

Yano et al. Novel zirconocene catalysts for the production of high molecular weight LLDPE in high-temperature polymerization, Macromolecular Chemistry and Physics, 1999, 200(4), 933-941.

Yano et al. Ethylene/1-hexene copolymerization with $Ph_2C(Cp)(Flu)ZrCl_2$ derivatives: correlation between ligand structure and copolymerization behavior at high temperature, Macromolecular Chemistry and Physics, 1999, 200, 1542.

Yano et al. Effect of ligand structures on high temperature homo- and copolymerization of ethylene by cationic hafnocene catalysts based on tetrakis(pentafluorophenyl)borate, Journal of Molecular Catalysis A: Chemical, 2000, 156(1-2), 133-141.

Nifant'ev, I. E., 5-Methoxy-Substituted Zirconium Bis-idenyl ansa-Complexes: Synthesis, Structure, and Catalytic Activity in the Polymerization and Copolymerization of Alkenes, Organometallics, 2012, vol. 31, No. 14, pp. 4962-4970.

CATALYSTS

This invention relates to new bisindenyl ligands, complexes thereof and catalysts comprising those complexes. The invention also relates to the use of the new bisindenyl metallocene catalysts for the production of polypropylene homopolymers or copolymers with high activity levels, high molecular weight, especially at low MFR, and with ideal melting points. The catalysts are especially useful in the manufacture of polypropylene copolymers as they exhibit remarkable catalyst activity in such polymerisations.

Metallocene catalysts have been used to manufacture polyolefins for many years. Countless academic and patent publications describe the use of these catalysts in olefin polymerisation. Metallocenes are now used industrially and polyethylenes and polypropylenes in particular are often produced using cyclopentadienyl based catalyst systems with different substitution patterns.

The present inventors sought new metallocenes, which provide high activity, especially in the case of copolymerization between propylene and ethylene or α-olefins of 4 to 8 C atoms to form propylene copolymers. The desired catalysts should also have improved performance in the production of high molecular weight polypropylene homopolymers and copolymers. Various prior art references aim for one or more of these features.

$C_2$-symmetric metallocenes similar to those we claim are disclosed for example in WO2007/116034. This document reports the synthesis and characterisation of the metallocene rac-Me$_2$Si(2-Me-4-Ph-5-OMe-6-tBuInd)$_2$ZrCl$_2$ and the use of it as a polymerisation catalyst after activation with MAO for the homopolymerisation of propylene and copolymerisation of propylene with ethylene and higher alpha-olefins in solution polymerisation.

WO02/02576 describes, inter alia, rac-Me$_2$Si[2-Me-4-(3,5-tBu$_2$Ph)Ind]$_2$ZrCl$_2$ and rac-Me$_2$Si[2-Me-4-(3,5-tBu$_2$Ph)Ind]$_2$ZrCl$_2$ (see also WO2014/096171) and its use in the manufacture of high Mw and high melting point polypropylene.

Asymmetrical metallocenes able to produce isotactic polypropylene have been described in the literature. WO2013/007650, describes certain asymmetrical catalysts comprising alkoxy groups at the 5-position of one of the rings such as dimethylsilylene($\eta^5$-6-tert-butyl-5-methoxy-2-methyl-4-phenyl-1H-inden-1-yl)-($\eta^5$-6-tert-butyl-2-methyl-4-phenyl-1H-inden-1-yl)zirconium dichloride. Despite its good performance, catalysts based on this reference are limited in terms of polypropylene homopolymer melting temperature, productivity at low MFR. In addition, the overall productivity of the catalyst still needs to be improved.

The catalysts of the invention should ideally be suited for use in solution or in conventional solid supported form, e.g. using silica or alumina supports, or can be used in solid form, however, being free of external support or carrier.

The present applicant has developed an alternative to conventional inorganic supports. In WO03/051934, the inventors proposed an alternative form of catalyst which is provided in solid form but does not require a conventional external carrier material such as silica. The invention is based on the finding that a homogeneous catalyst system containing an organometallic compound of a transition metal can be converted, in a controlled way, to solid, uniform catalyst particles by first forming a liquid/liquid emulsion system, which comprises as the dispersed phase, said solution of the homogeneous catalyst system, and as the continuous phase a solvent immiscible therewith, and then solidifying said dispersed droplets to form solid particles comprising the said catalyst.

The invention described in WO03/051934 enabled the formation of solid spherical catalyst particles of said organo transition metal catalyst without using e.g. external porous carrier particles, such as silica, normally required in the art. Thus, problems relating to catalyst silica residues can be solved by this type of catalyst. Further, it could be seen that catalyst particles having improved morphology, will give, due to the replica effect, polymer particles having improved morphology as well. Catalysts of this invention should be able to utilise this method.

The inventors have found new metallocene catalysts, which are easy and cheap to make synthetically, have improved polymerisation behaviour, higher catalyst productivity, improved performance in the production of high molecular weight polypropylene homopolymer, and reduced chain transfer to ethylene, enabling the production of copolymers. During copolymer manufacture, the reduced chain transfer to ethylene, enables the production of high molecular weight copolymers.

The metallocene structures of the prior art do not provide these key polymer properties in one structure.

When designing an improved metallocene structure, one possibility might be to combine the substitution patterns in the prior art above. For example, we combined metallocenes identified herein as MC-CE2 and MC-CE3 to make metallocene MC-CE4. This metallocene did not however offer the properties we desired.

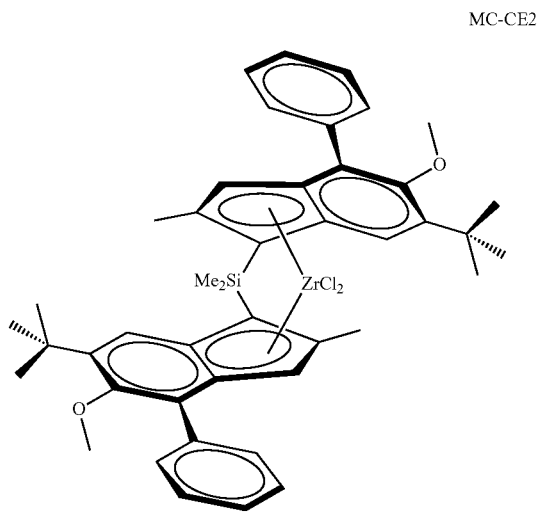

MC-CE2 rac-Me$_2$Si(2-Me-4-Ph-5-OMe-6-tBuInd)$_2$ZrCl$_2$
WO 2007/116034

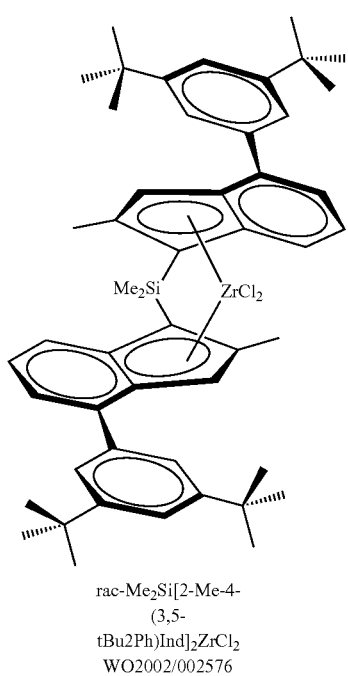

rac-Me$_2$Si[2-Me-4-
(3,5-
tBu2Ph)Ind]$_2$ZrCl$_2$
WO2002/002576

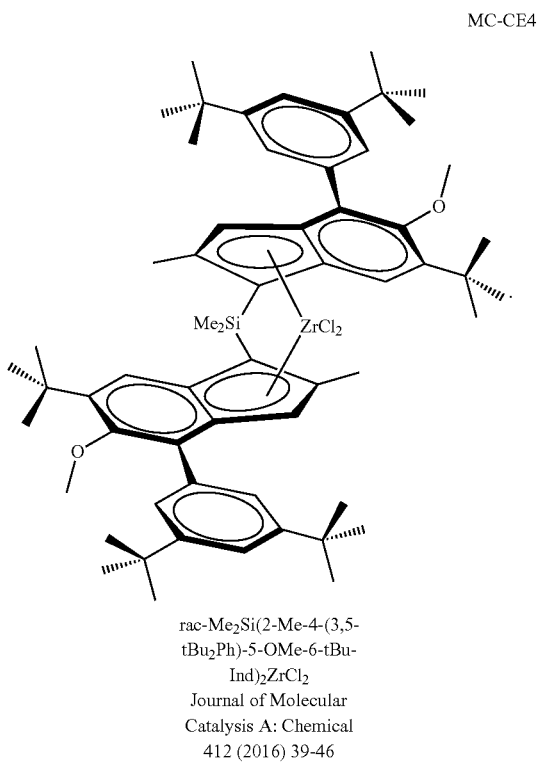

rac-Me$_2$Si(2-Me-4-(3,5-
tBu$_2$Ph)-5-OMe-6-tBu-
Ind)$_2$ZrCl$_2$
Journal of Molecular
Catalysis A: Chemical
412 (2016) 39-46

The structure rac-Me$_2$Si(2-Me-4-(3,5-tBu$_2$Ph)-5-OMe-6-tBu-Ind)$_2$ZrCl$_2$ (MC-CE4) demonstrated that simple sum of substitution patterns does not yield the desired performance, i.e. the combination of high molecular weight and high activity from MC-CE2 with the high homopolymer polypropylene melting point from MC-CE3.

The inventors have now realised that a particular substitution pattern on the 4-position phenyl ring on the metallocenes of the invention leads to the advantageous properties that we desire. The use of 3,5-disubstituted phenyl groups in which the 3,5-substituents are not tertiary has been found to lead to remarkable properties in the manufacture of propylene polymers.

In particular, the catalysts of the invention enable very high activity in propylene homopolymerisation;
very high molecular weight capability;
extremely high activity in C2/C3 copolymerisation activity;
high molecular weight for C2/C3 copolymers;
improved comonomer incorporation in propylene copolymers;
high activity for low MFR (high Mw) polymer products;
desirable melting points.

SUMMARY OF INVENTION

Thus, viewed from one aspect the invention provides a complex of formula (I)

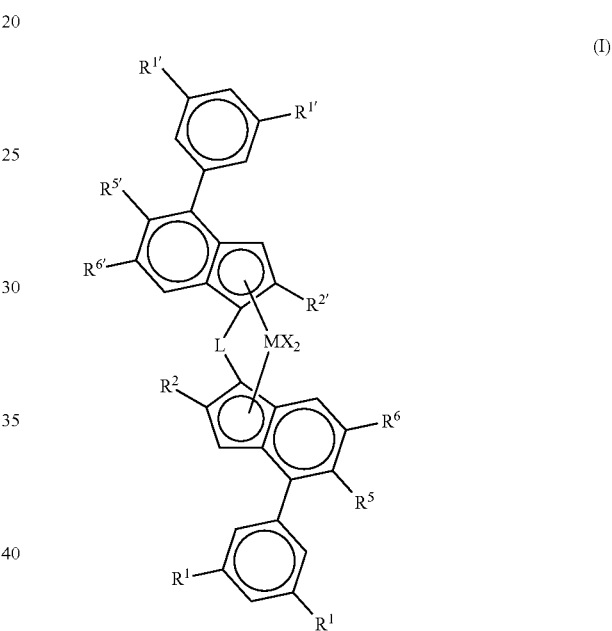

(I)

wherein
M is zirconium or hafnium;
each X independently is a sigma ligand;
L is a divalent bridge selected from —R'$_2$C—, —R'$_2$C—CR'$_2$—, —R'$_2$Si—, R'$_2$Si—SiR'$_2$—, —R'$_2$Ge—, wherein each R' is independently a hydrogen atom or a C$_1$-C$_{20}$-hydrocarbyl group optionally containing one or more silicon atoms or heteroatoms of Group 14-16 of the periodic table or fluorine atoms, and optionally two R' groups taken together can form a ring;

R$^2$ and R$^{2'}$ are each independently a C$_1$-C$_{20}$ hydrocarbyl group, —OC$_{1-20}$ hydrocarbyl group or —SC$_{1-20}$ hydrocarbyl group;

R$^5$ is a —OC$_{1-20}$ hydrocarbyl group or —SC$_{1-20}$ hydrocarbyl group, said R$^5$ group being optionally substituted by one or more halo groups;

R$^{5'}$ is hydrogen or a C$_{1-20}$ hydrocarbyl group; —OC$_{1-20}$ hydrocarbyl group or —SC$_{1-20}$ hydrocarbyl group; said C$_{1-20}$ hydrocarbyl group being optionally substituted by one or more halo groups;

R$^6$ and R$^{6'}$ are each independently a C$_{1-20}$ hydrocarbyl group; —OC$_{1-20}$ hydrocarbyl group or —SC$_{1-20}$ hydrocarbyl group;

each $R^1$ and $R^{1'}$ are independently —$CH_2R^x$ wherein $R^x$ are each independently H, or a $C_{1-20}$ hydrocarbyl group, optionally containing heteroatoms.

Viewed from another aspect the invention provides a catalyst comprising
(i) a complex of formula (I) as hereinbefore defined; and
(ii) a cocatalyst comprising a compound of a group 13 metal, e.g. aluminium or boron.

The catalyst of the invention can be used in non-supported form or in solid form. The catalyst of the invention may be used as a homogeneous catalyst or heterogeneous catalyst.

The catalyst of the invention in solid form, preferably in solid particulate form can be either supported on an external carrier material, like silica or alumina, or, in a particularly preferred embodiment, is free from an external carrier, however still being in solid form. For example, the solid catalyst is obtainable by a process in which
(a) a liquid/liquid emulsion system is formed, said liquid/liquid emulsion system comprising a solution of the catalyst components (i) and (ii) dispersed in a solvent so as to form dispersed droplets; and
(b) solid particles are formed by solidifying said dispersed droplets.

Viewed from another aspect the invention provides a process for the manufacture of a catalyst as hereinbefore defined comprising obtaining a complex of formula (I) and a cocatalyst as hereinbefore described;
forming a liquid/liquid emulsion system, which comprises a solution of catalyst components (i) and (ii) dispersed in a solvent, and solidifying said dispersed droplets to form solid particles.

Viewed from another aspect the invention provides the use in olefin polymerisation of a catalyst as hereinbefore defined, preferably for the formation of a polyethylene or polypropylene, especially a polypropylene homopolymer or copolymer, more especially a propylene copolymer with ethylene or α-olefins of 4 to 8 C atoms, especially hexene.

Viewed from another aspect the invention provides a process for the polymerisation of at least one olefin comprising reacting said at least one olefin with a catalyst as hereinbefore described, especially for the formation of propylene homopolymers or copolymers with ethylene or α-olefins of 4 to 8 C atoms, especially hexene.

Definitions

Throughout the description the following definitions are employed.

By free from an external carrier is meant that the catalyst does not contain an external support, such as an inorganic support, for example, silica or alumina, or an organic polymeric support material.

The term $C_{1-20}$ hydrocarbyl group includes $C_{1-20}$ alkyl, $C_{2-20}$ alkenyl, $C_{2-20}$ alkynyl, $C_{3-20}$ cycloalkyl, $C_{3-20}$ cycloalkenyl, $C_{6-20}$ aryl groups, $C_{7-20}$ alkylaryl groups or $C_{7-20}$ arylalkyl groups or of course mixtures of these groups such as cycloalkyl substituted by alkyl. Linear and branched hydrocarbyl groups cannot contain cyclic units. Aliphatic hydrocarbyl groups cannot contain aryl rings.

Unless otherwise stated, preferred $C_{1-20}$ hydrocarbyl groups are $C_{1-20}$ alkyl, $C_{4-20}$ cycloalkyl, $C_{5-20}$ cycloalkylalkyl groups, $C_{7-20}$ alkylaryl groups, $C_{7-20}$ arylalkyl groups or $C_{6-20}$ aryl groups, especially $C_{1-10}$ alkyl groups, $C_{6-10}$ aryl groups, or $C_{7-12}$ arylalkyl groups, e.g. $C_{1-8}$ alkyl groups. Most especially preferred hydrocarbyl groups are methyl, ethyl, propyl, isopropyl, tert-butyl, isobutyl, $C_{5-6}$-cycloalkyl, cyclohexylmethyl, phenyl or benzyl. Also preferred $C_{1-20}$ hydrocarbyl groups are isopentyl or neopentyl.

The term halo includes fluoro, chloro, bromo and iodo groups, especially chloro or fluoro groups, when relating to the complex definition.

Where a hydrocarbyl group comprises one or more heteroatoms, that heteroatom can be in the middle of the hydrocarbyl group or at the ends thereof. Thus a $C_{1-6}$alkyl comprising a heteroatom might be an alkoxy group —OMe or an ether type group —$CH_2$—O—$CH_3$.

The oxidation state of the metal ion is governed primarily by the nature of the metal ion in question and the stability of the individual oxidation states of each metal ion.

It will be appreciated that in the complexes of the invention, the metal ion M is coordinated by ligands X so as to satisfy the valency of the metal ion and to fill its available coordination sites. The nature of these 6-ligands can vary greatly.

The invention requires that the pendant carbon atom on the meta-positions of the 4-position phenyl rings, must be bound to two or three hydrogen atoms.

Catalyst activity is defined in this application to be the amount of polymer produced/g catalyst/h. Catalyst metal activity is defined here to be the amount of polymer produced/g Metal/h. The term productivity is also sometimes used to indicate the catalyst activity although herein it designates the amount of polymer produced per unit weight of catalyst.

The term molecular weight is used herein to refer to weight average molecular weight Mw unless otherwise stated.

DETAILED DESCRIPTION OF INVENTION

The complexes of the invention can be asymmetrical or symmetrical. Asymmetrical means simply that the two indenyl ligands forming the metallocene are different, that is, each indenyl ligand bears a set of substituents that are either chemically different, or located in different positions with respect to the other indenyl ligand. Symmetrical complexes are based on two identical indenyl ligands.

The complexes of the invention are chiral, racemic bridged bisindenyl metallocenes. The metallocenes of the invention are either $C_2$-symmetric or $C_1$-symmetric. When they are $C_1$-symmetric they still maintain a pseudo-$C_2$-symmetry since they maintain $C_2$-symmetry in close proximity of the metal center, although not at the ligand periphery. By nature of their chemistry, both a meso form and a racemic enantiomer pair (in case of $C_2$-symmetric complexes) or anti and syn enantiomer pairs (in case of $C_1$-symmetric complexes) are formed during the synthesis of the complexes. For the purpose of this invention, racemic-anti means that the two indenyl ligands are oriented in opposite directions with respect to the cyclopentadienyl-metal-cyclopentadienyl plane, while racemic-syn means that the two indenyl ligands are oriented in the same direction with respect to the cyclopentadienyl-metal-cyclopentadienyl plane, as shown in the Figure below.

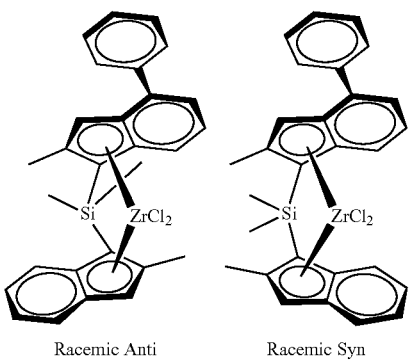

Racemic Anti    Racemic Syn

Formula (I) is intended to cover both syn- and anti-configurations, preferably anti.

It is preferred if the metallocenes of the invention are employed as the racemic or racemic-anti isomers. Ideally therefore at least 95% mol, such as at least 98% mol, especially at least 99% mol of the metallocene is in the racemic or racemic-anti isomeric form.

In the catalysts of the invention the following preferences apply.

M is preferably Zr or Hf

Each X, which may be the same or different, is preferably a hydrogen atom, a halogen atom, a R, OR, $OSO_2CF_3$, OCOR, SR, $NR_2$ or $PR_2$ group wherein R is a linear or branched, cyclic or acyclic, $C_{1-20}$ alkyl, $C_{2-20}$ alkenyl, $C_{2-20}$ alkynyl, $C_{6-20}$ aryl, $C_{7-20}$ alkylaryl or $C_{7-20}$ arylalkyl radical; optionally containing heteroatoms belonging to groups 14-16. R is preferably a $C_{1-6}$ alkyl, phenyl or benzyl group.

Most preferably each X is independently a hydrogen atom, a halogen atom, $C_{1-6}$ alkoxy group or an R group, e.g. preferably a $C_{1-6}$ alkyl, phenyl or benzyl group. Most preferably X is chlorine, benzyl or a methyl group. Preferably both X groups are the same. The most preferred options are two chlorides, two methyl or two benzyl groups.

L is preferably an alkylene linker or a bridge comprising a heteroatom, such as silicon or germanium, e.g. —$SiR^8_2$—, wherein each $R^8$ is independently $C_{1-20}$ alkyl, $C_{3-10}$ cycloalkyl, $C_{6-20}$ aryl or tri($C_{1-20}$ alkyl)silyl, such as trimethylsilyl. So $R^8$ may represent a cyclic group. Also, two $R^8$ groups taken together can also form a ring.

More preferably $R^8$ is $C_{1-6}$ alkyl, especially methyl or $C_{3-7}$ cycloalkyl, such as cyclohexyl, or the two $R^8$ groups can also be part of a ring. Most preferably, L is a dimethylsilyl, or a methylcyclohexylsilyl bridge (i.e. Me-Si-cyclohexyl), ethylene or methylene.

$R^2$ and $R^{2'}$ may be the same or different, preferably the same. $R^2$ and $R^{2'}$ are preferably linear or branched $C_{1-10}$ alkyl group. More preferably it is a linear or branched $C_{1-6}$ alkyl group, especially linear $C_{1-6}$ alkyl group such as methyl or ethyl. If branched, they are not branched at the alpha carbon, i.e. not at the carbon atom of $R^2$ or $R^{2'}$,' which is bound to indene. Most especially $R^2$ and $R^{2'}$ are methyl, ethyl, isobutyl or neopentyl. In one embodiment both are either methyl or neopentyl.

$R^6$ and $R^{6'}$ may be the same or different. It is preferred if each $R^6$ and $R^{6'}$ is a $C_{1-20}$ hydrocarbyl group, such as a $C_{1-20}$ alkyl group or $C_{6-10}$ aryl group. More preferably, $R^6$ and $R^{6'}$ are a linear or branched $C_{1-10}$ alkyl group such as linear or branched $C_{3-8}$ alkyl group. Most preferably $R^6$ is a branched $C_{3-8}$ alkyl such as tert-butyl group. Most preferably $R^{6'}$ is a linear $C_{1-8}$ alkyl group or branched $C_{3-8}$ alkyl group, such as methyl, ethyl, isopropyl or tert-butyl group. Branching might be alpha or beta to the indenyl ring.

$R^5$ is preferably a group $ZR^3$. $R^{5'}$ is preferably hydrogen or a group $Z'R^{3'}$.

Z and Z' are each O or S, preferably O.

$R^3$ and $R^{3'}$ are each independently preferably a $C_{1-10}$ hydrocarbyl group, especially a $C_{1-10}$ linear or branched alkyl, $C_{2-10}$ alkenyl, $C_{3-10}$ cycloalkyl or $C_{3-10}$ cycloalkenyl group, or $C_{6-10}$ aryl, $C_{7-10}$ alkylaryl or $C_{7-10}$ arylalkyl group optionally substituted by one or more halo groups. Most especially $R^3$ and $R^{3'}$ are $C_{1-6}$ alkyl group, such as a linear $C_{1-6}$ alkyl groups, e.g. methyl or ethyl or are phenyl based groups optionally substituted with one or more halo groups such as phenyl or $C_6F_5$. Preferably, $R^3$ and $R^{3'}$ are linear $C_{1-3}$ alkyl groups, especially methyl. $R^5$ is preferably a group $OC_{1-6}$ alkyl such as methoxy.

Whilst the $R^1$ groups can be the same or different, it is preferred if they are the same. $R^1$ groups are preferably H or $C_{1-10}$ alkyl, more preferably H or $C_{1-6}$ alkyl. $R^1$ groups are still more preferably H or $C_{1-2}$ alkyl group. Thus, the groups $R^1$ and $R^{1'}$ are independently preferably a methyl, ethyl or propyl group.

In a most preferred embodiment all $R^1$ and all $R^{1'}$ groups are methyl or ethyl. In a most preferred embodiment all $R^1$ and all $R^{1'}$ groups are methyl.

It is within the scope of the invention for the two 4-aryl groups to be different (e.g. 3,5-dimethylphenyl on one indene and 3,5-di-ethylphenyl on the other) or the same. Alternatively, the two 3,5-substituents on each aryl group can be different (e.g. 3-methyl-5-propyl) or the same.

It is preferred if the two 3,5-substituents on each aryl group are the same. It is preferred if the two 4-position aryl groups are the same. Most especially, it is preferred the 4-position aryl groups are the same on both ligands and that both 3,5-substituents are the same.

Thus, preferred complexes of the invention are of formula (II)

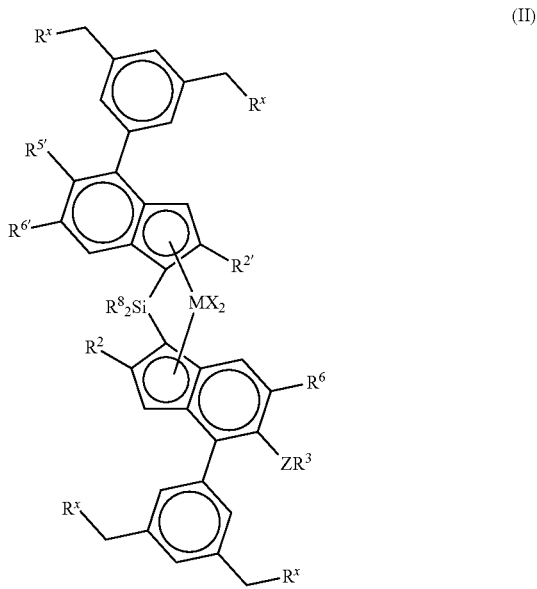

(II)

wherein

M is zirconium (Zr) or hafnium (Hf);

each X is a sigma ligand, preferably each X is independently a hydrogen atom, a halogen atom, $C_{1-6}$ alkoxy group, $C_{1-6}$ alkyl, phenyl or benzyl group;

each $R^8$ is a $C_{1-20}$ hydrocarbyl group or two $R^8$ groups taken together can form a ring;

each $R^2$ or $R^{2'}$ is a $C_{1-10}$ alkyl group;

$R^6$ is $C_{1-10}$ alkyl group or $C_{6-10}$ aryl group;

$R^{6'}$ is $C_{1-10}$ alkyl group or $C_{6-10}$ aryl group;

$R^{5'}$ is hydrogen or $ZR^{3'}$

Z is O or S;

$R^3$ and $R^{3'}$, which can be same or different, are $C_{1-10}$ hydrocarbyl groups such as $C_{1-10}$ linear or branched alkyl, $C_{2-10}$ alkenyl, $C_{3-10}$ cycloalkyl or $C_{3-10}$ cycloalkenyl group, or $C_{6-10}$ aryl, $C_{7-10}$ alkylaryl or $C_{7-10}$ arylalkyl group optionally substituted by one or more halo groups;

each $R^x$ is independently H or a $C_{1-12}$ hydrocarbyl group, e.g. $C_{1-10}$ alkyl group.

Viewed from another aspect the invention provides a complex of formula (IIIa) or (IIIb)

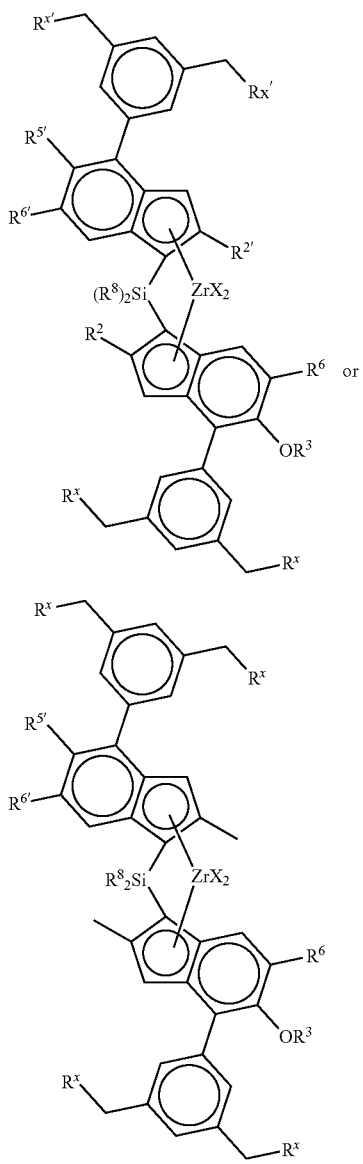

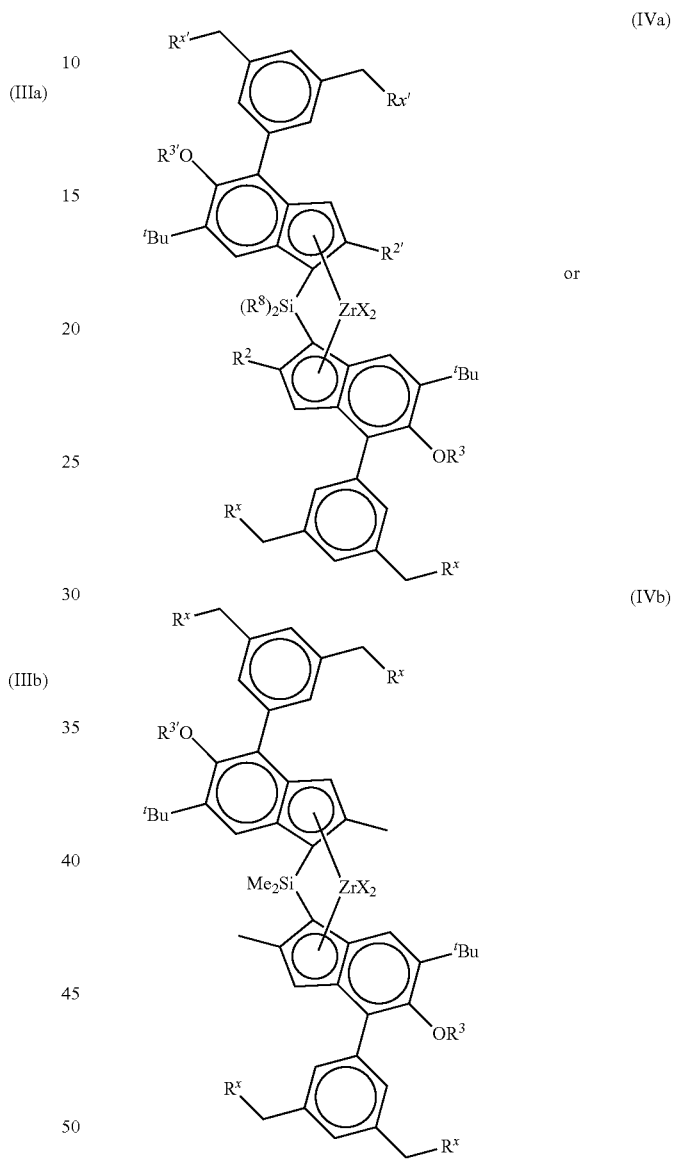

each X is a sigma ligand, preferably each X is independently a hydrogen atom, a halogen atom, $C_{1-6}$ alkoxy group, $C_{1-6}$ alkyl, phenyl or benzyl group;

$R^8$ is a $C_{1-6}$ alkyl group or $C_{3-7}$ cycloalkyl group;

$R^6$ is a $C_{1-10}$ alkyl group;

$R^{6'}$ is a $C_{1-10}$ alkyl group;

$R^{5'}$ is hydrogen or $OR^{3'}$;

$R^3$ and $R^{3'}$, which can be same or different, are $C_{1-10}$ hydrocarbyl groups such as $C_{1-10}$ linear or branched alkyl, $C_{2-10}$ alkenyl, $C_{3-10}$ cycloalkyl or $C_{3-10}$ cycloalkenyl group, or $C_{6-10}$ aryl, $C_{7-10}$ alkylaryl or $C_{7-10}$ arylalkyl group optionally substituted by one or more halo groups;

$R^2$ and $R^{2'}$ which can be same or different are $C_{1-6}$ alkyl; and each $R^x$ is independently H or a $C_{1-10}$ alkyl group.

Viewed from a preferred aspect, the complex of the invention is of formula (IVa) or (IVb):

wherein each X is a sigma ligand, preferably each X is independently a hydrogen atom, a halogen atom, $C_{1-6}$-alkoxy group, $C_{1-6}$-alkyl, phenyl or benzyl group;

$R^x$ is H or a $C_{1-4}$ alkyl group;

$R^3$ and $R^{3'}$, which can be same or different, are $C_{1-10}$ hydrocarbyl groups such as $C_{1-10}$ linear or branched alkyl, $C_{2-10}$ alkenyl, $C_{3-10}$ cycloalkyl or $C_{3-10}$ cycloalkenyl group, or $C_{6-10}$ aryl, $C_{7-10}$ alkylaryl or $C_{7-10}$ arylalkyl group optionally substituted by one or more halo groups; and $R^2$ and $R^{2'}$ which can be same or different are $C_{1-6}$ alkyl.

Viewed from another preferred aspect, the complex of the invention is of formula (V):

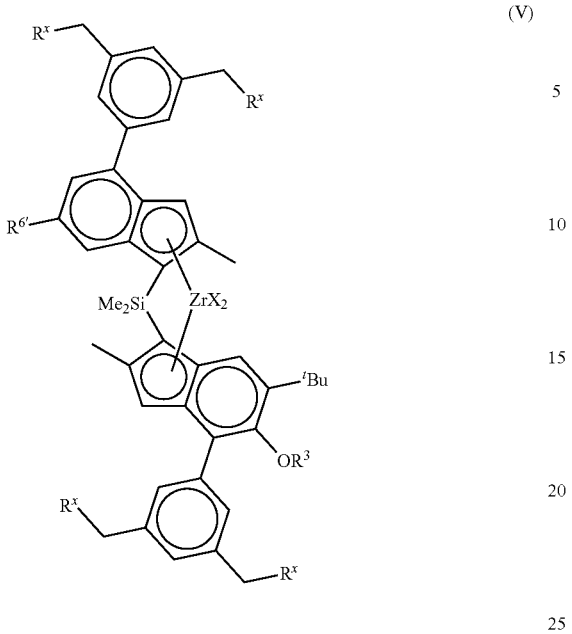

(V)

each X is a sigma ligand, preferably each X is independently a hydrogen atom, a halogen atom, $C_{1-6}$-alkoxy group, $C_{1-6}$-alkyl, phenyl or benzyl group;

$R^x$ is H or methyl;

$R^3$ is a $C_{1-10}$ hydrocarbyl group such as $C_{1-10}$ linear or branched alkyl, $C_{2-10}$ alkenyl, $C_{3-10}$ cycloalkyl or $C_{3-10}$ cycloalkenyl group, or $C_{6-10}$ aryl, $C_{7-10}$ alkylaryl or $C_{7-10}$ arylalkyl group optionally substituted by one or more halo groups;

$R^{6'}$ is a $C_{1-4}$ linear or branched hydrocarbyl such as methyl, ethyl, isopropyl, isobutyl.

In formulae (II) to (V), $R^3$ is preferably a $C_{1-6}$ linear or branched alkyl group, or $C_{6-10}$ aryl, such as a linear $C_{1-4}$ alkyl group.

Particular compounds of the invention include:

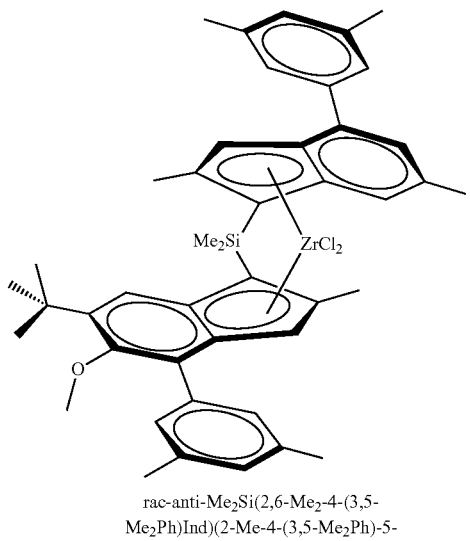

MC-IE2 rac-anti-Me₂Si(2,6-Me₂-4-(3,5-Me₂Ph)Ind)(2-Me-4-(3,5-Me₂Ph)-5-OMe-6-tBu-Ind)ZrCl₂

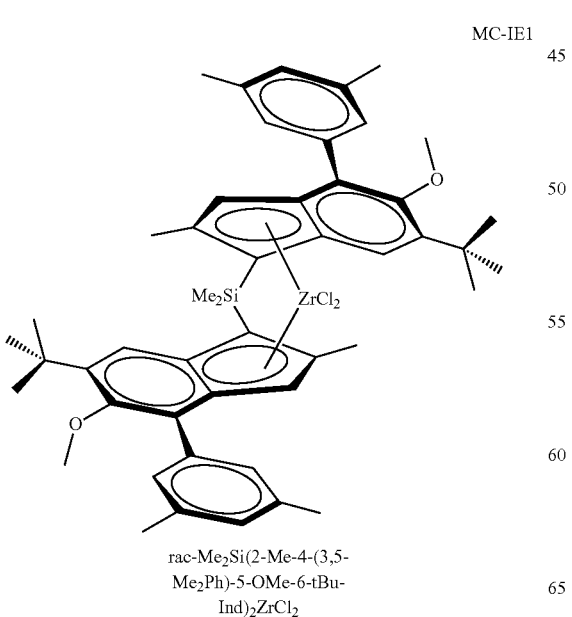

MC-IE1 rac-Me₂Si(2-Me-4-(3,5-Me₂Ph)-5-OMe-6-tBu-Ind)₂ZrCl₂

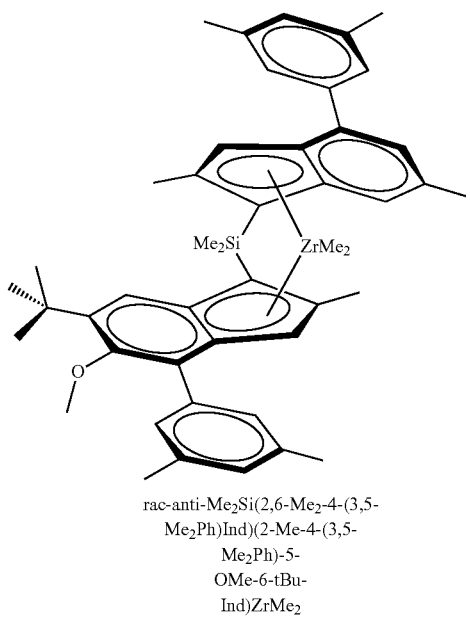

MC-IE3 rac-anti-Me₂Si(2,6-Me₂-4-(3,5-Me₂Ph)Ind)(2-Me-4-(3,5-Me₂Ph)-5-OMe-6-tBu-Ind)ZrMe₂

MC-IE4

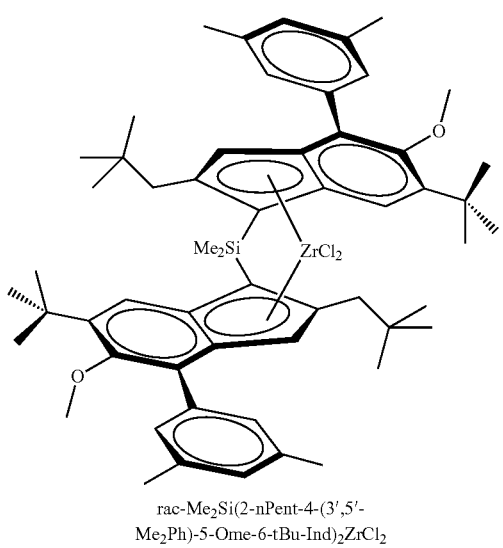

rac-Me$_2$Si(2-nPent-4-(3',5'-Me$_2$Ph)-5-Ome-6-tBu-Ind)$_2$ZrCl$_2$

For the avoidance of doubt, any narrower definition of a substituent offered above can be combined with any other broad or narrowed definition of any other substituent.

Throughout the disclosure above, where a narrower definition of a substituent is presented, that narrower definition is deemed disclosed in conjunction with all broader and narrower definitions of other substituents in the application.

Synthesis

The ligands required to form the complexes and hence catalysts of the invention can be synthesised by any process and the skilled organic chemist would be able to devise various synthetic protocols for the manufacture of the necessary ligand materials.

For example, the following general synthetic scheme can be used:

Scheme 1

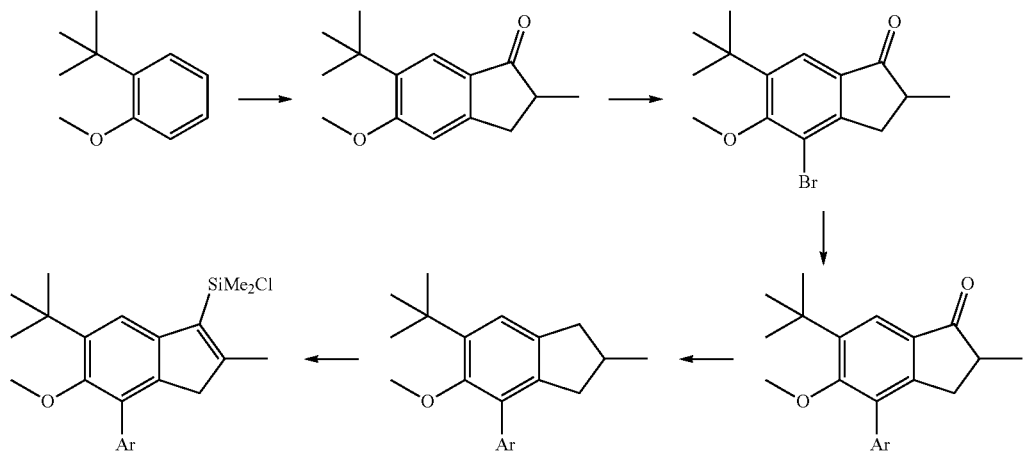

Suitable reagents for this transformation are given in the examples section. Whilst this scheme refers to specific compounds, the general principles displayed here apply to the metallocenes of the invention. If the ligands are asymmetric, a conventional reaction with SiMe$_2$Cl$_2$ cannot be effected to bridge two ligands as that leads to symmetrical products. Instead, each ligand has to be attached to the bridge stepwise with control over the reaction stoichiometry.

In one embodiment, manufacture of the metallocenes of the invention involves a one pot conversion of:

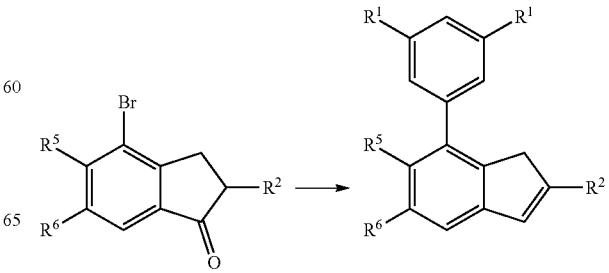

using a boronic acid derivative of the required 3,5-disubstituted phenyl in the presence of a catalyst and 2-methyltetrahydrofuran.

Thus viewed from another aspect the invention provides a one pot process comprising (I) reacting a compound of formula (A):

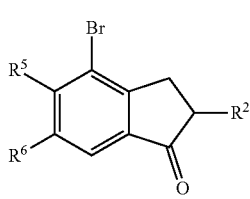

(A)

with a 3,5-di-R¹-phenyl boronic acid in the presence of a catalyst and 2-methyltetrahydrofuran to form compound (B);

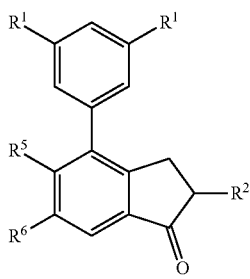

and (II) reducing compound (B) in the presence of 2-methyltetrahydrofuran to form compound (C):

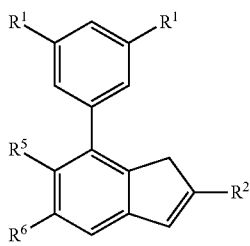

(C)

e.g. using a reducing agent such as sodium borohydride;
wherein R¹, R², R⁵ and R⁶ are as hereinbefore defined.

The catalyst used is typically a transition metal catalyst such as a Pd or Pt catalyst. Ideally a Pd/Pt mixed catalyst is used such as Pd(PtBu₃)₂.

The first step of the reaction may require the presence of a weak base such as a carbonate, e.g. sodium carbonate. Crucially, the presence of the 2-methyltetrahydrofuran is believed to maximise the yield of the products.

The second step of this process is a reduction using a reducing agent, e.g. sodium borohydride. As the reaction is a "one pot" reaction, the compound (B) is not isolated between steps and hence 2-methyltetrahydrofuran is also present in the second step of the process as carry over from step 1. Alcohol may also be added to the second step to enhance the reaction. The term one pot is used therefore to indicate that the compound (B) is not isolated between steps.

It will be appreciated that water may be used as a cosolvent in the first step of the process. Before step (II) of the process, the water phase may be separated from the organic phase and the organic phase dried before use in the second step of the process.

The preferred definitions of R¹, R², R⁵ and R⁶ given above and the preferred R¹, R², R⁵ and R⁶ options covered by formulae (II) to (V) apply to this embodiment.

Whilst the process above is described in relation to a ligand featuring R¹, R², R⁵ and R⁶ it will be appreciated that exactly the same process can be used to prepare a ligand comprising variables R¹', R²', R⁵' and R⁶'. This forms a further aspect of the invention.

Intermediates

Whilst the invention primarily relates to catalysts, it will be appreciated that the complexes of the invention and the ligands used to form those complexes are also new. The invention further relates therefore to complexes of formula (I) and ligands of formula (I') from which the MX₂ coordination has been removed and the proton returned to the indenyl.

Ligands of interest are therefore of formula (I')

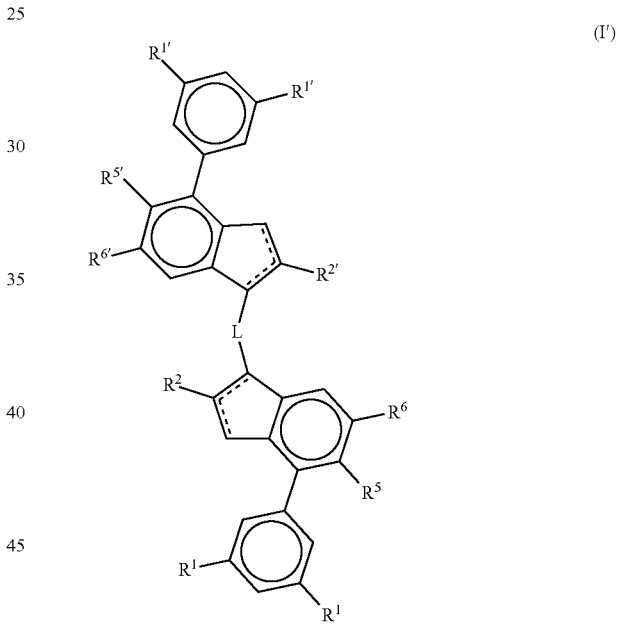

(I')

wherein the substituents are as hereinbefore defined and the dotted lines represent a double bond present in between carbons 1 and 2 or 2 and 3 of the indenyl ring. It will be appreciated therefore that this molecule contains double bond isomers. By double bond isomers is meant the compounds where the double bond is positioned between the 2 and 3 atoms rather than 1 and 2 atoms of the bicyclic ring. It may be that more than one double bond isomer is present in a sample. Preferred ligands are analogues of the complexes described above from which MX₂ coordination has been removed and the proton returned to the indenyl.

Cocatalyst

To form an active catalytic species it is normally necessary to employ a cocatalyst as is well known in the art. Cocatalysts comprising one or more compounds of Group 13 metals, like organoaluminum compounds or borates used to activate metallocene catalysts are suitable for use in this invention.

The olefin polymerisation catalyst system of the invention comprises (i) a complex in which the metal ion is coordinated by a ligand of the invention; and normally (ii) an aluminium alkyl compound (or other appropriate cocatalyst), or the reaction product thereof. Thus the cocatalyst is preferably an alumoxane, like MAO or an alumoxane other than MAO.

Borate cocatalysts can also be employed. It will be appreciated by the skilled man that where boron based cocatalysts are employed, it is normal to preactivate the complex by reaction thereof with an aluminium alkyl compound, such as TIBA. This procedure is well known and any suitable aluminium alkyl, e.g. $Al(C_{1-6}\text{-alkyl})_3$. can be used.

Boron based cocatalysts of interest include those of formula

wherein Y is the same or different and is a hydrogen atom, an alkyl group of from 1 to about 20 carbon atoms, an aryl group of from 6 to about 15 carbon atoms, alkylaryl, arylalkyl, haloalkyl or haloaryl each having from 1 to 10 carbon atoms in the alkyl radical and from 6-20 carbon atoms in the aryl radical or fluorine, chlorine, bromine or iodine. Preferred examples for Y are methyl, propyl, isopropyl, isobutyl or trifluoromethyl, unsaturated groups such as aryl or haloaryl like phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl) phenyl. Preferred options are trifluoroborane, triphenylborane, tris(4-fluorophenyl)borane, tris(3,5-difluorophenyl)borane, tris(4-fluoromethylphenyl)borane, tris(2,4,6-trifluorophenyl)borane, tris(penta-fluorophenyl)borane, tris(tolyl)borane, tris(3,5-dimethyl-phenyl)borane, tris(3,5-difluorophenyl)borane and/or tris (3,4,5-trifluorophenyl)borane.

Particular preference is given to tris(pentafluorophenyl) borane.

It is preferred however is borates are used, i.e. compounds containing a borate 3+ ion. Such ionic cocatalysts preferably contain a non-coordinating anion such as tetrakis(pentafluorophenyl)borate and tetraphenylborate. Suitable counterions are protonated amine or aniline derivatives such as methylammonium, anilinium, dimethylammonium, diethylammonium, N-methylanilinium, diphenylammonium, N,N-dimethylanilinium, trimethylammonium, triethylammonium, tri-n-butylammonium, methyldiphenylammonium, pyridinium, p-bromo-N,N-dimethylanilinium or p-nitro-N,N-dimethylanilinium. Preferred ionic compounds which can be used according to the present invention include: triethylammoniumtetra(phenyl)borate, tributylammoniumtetra(phenyl)borate, trimethylammoniumtetra(tolyl)borate, tributylammoniumtetra(tolyl)borate, tributylammoniumtetra (pentafluorophenyl)borate, tripropylammoniumtetra (dimethylphenyl)borate, tributylammoniumtetra (trifluoromethylphenyl)borate, tributylammoniumtetra(4-fluorophenyl)borate, N,N-dimethylcyclohexylammoniumtetrakis(pentafluorophenyl) borate, N,N-dimethylbenzylammoniumtetrakis (pentafluorophenyl)borate, N,N-dimethylaniliniumtetra (phenyl)borate, N,N-diethylaniliniumtetra(phenyl)borate, N,N-dimethylaniliniumtetrakis(pentafluorophenyl)borate, N,N-di(propyl)ammoniumtetrakis(pentafluorophenyl)borate, di(cyclohexyl)ammoniumtetrakist(pentafluorophenyl) borate, triphenylphosphoniumtetrakis(phenyl)borate, triethylphosphoniumtetrakis(phenyl)borate, diphenylphosphoniumtetrakis(phenyl)borate, tri(methylphenyl)phosphoniumtetrakis(phenyl)borate, tri(dimethylphenyl)phosphoniumtetrakis(phenyl)borate, triphenylcarbeniumtetrakis(pentafluorophenyl)borate, or ferroceniumtetrakis (pentafluorophenyl)borate. Preference is given to triphenylcarbeniumtetrakis(pentafluorophenyl) borate, N,N-dimethylcyclohexylammoniumtetrakis(pentafluorophenyl) borate or N,N-dimethylbenzylammoniumtetrakis(pentafluorophenyl)borate.

The use of $B(C_6F_5)_3$, $C_6H_5N(CH_3)_2H:B(C_6F_5)_4$, $(C_6H_5)_3C:B(C_6F_5)_4$ or $Ni(CN)_4[B(C_6F_5)_3]_4{}^{2-}$ is especially preferred.

Suitable amounts of cocatalyst will be well known to the skilled man.

Catalyst Manufacture

The metallocene complex of the present invention can be used in combination with a suitable cocatalyst as a catalyst for the polymerization of olefins, e.g. in a solvent such as toluene or an aliphatic hydrocarbon, (i.e. for polymerization in solution), as it is well known in the art. Preferably, polymerization of olefins, especially propylene, takes place in the condensed phase or in gas phase.

The catalyst of the invention can be used in supported or unsupported form. The particulate support material used is preferably an organic or inorganic material, such as silica, alumina or zirconia or a mixed oxide such as silica-alumina, in particular silica, alumina or silica-alumina. The use of a silica support is preferred. The skilled man is aware of the procedures required to support a metallocene catalyst.

Especially preferably the support is a porous material so that the complex may be loaded into the pores of the support, e.g. using a process analogous to those described in WO94/14856 (Mobil), WO95/12622 (Borealis) and WO2006/097497. The particle size is not critical but is preferably in the range 5 to 200 µm, more preferably 20 to 80 µm. The use of these supports is routine in the art.

In an alternative embodiment, no support is used at all. Such a catalyst can be prepared in solution, for example in an aromatic solvent like toluene, by contacting the metallocene (as a solid or as a solution) with the cocatalyst, for example methylaluminoxane or a borane or a borate salt previously dissolved in an aromatic solvent, or can be prepared by sequentially adding the dissolved catalyst components to the polymerization medium. In a preferred embodiment, the metallocene (when X differs from alkyl or hydrogen) is preoreacted with an aluminium alkyl, in a ratio metal/aluminium of from 1:1 up to 1:500, preferably from 1:1 up to 1:250, and then combined with a solution of the borane or borate cocatalyst dissolved in an aromatic solvent, either in a separate vessel or directly into the polymerization reactor. Preferred metal/boron ratios are between 1:1 and 1:100, more preferably 1:1 to 1:10.

In one particularly preferred embodiment, no external carrier is used but the catalyst is still presented in solid particulate form. Thus, no external support material, such as inert organic or inorganic carrier, for example silica as described above is employed.

In order to provide the catalyst of the invention in solid form but without using an external carrier, it is preferred if a liquid/liquid emulsion system is used. The process involves forming dispersing catalyst components (i) and (ii) in a solvent, and solidifying said dispersed droplets to form solid particles.

In particular, the method involves preparing a solution of one or more catalyst components; dispersing said solution in an solvent to form an emulsion in which said one or more catalyst components are present in the droplets of the dispersed phase; immobilising the catalyst components in the dispersed droplets, in the absence of an external particulate porous support, to form solid particles comprising the said catalyst, and optionally recovering said particles.

This process enables the manufacture of active catalyst particles with improved morphology, e.g. with a predetermined spherical shape, surface properties and particle size and without using any added external porous support material, such as an inorganic oxide, e.g. silica. By the term "preparing a solution of one or more catalyst components" is meant that the catalyst forming compounds may be combined in one solution which is dispersed to the immiscible solvent, or, alternatively, at least two separate catalyst solutions for each part of the catalyst forming compounds may be prepared, which are then dispersed successively to the solvent.

In a preferred method for forming the catalyst at least two separate solutions for each or part of said catalyst may be prepared, which are then dispersed successively to the immiscible solvent.

More preferably, a solution of the complex comprising the transition metal compound and the cocatalyst is combined with the solvent to form an emulsion wherein that inert solvent forms the continuous liquid phase and the solution comprising the catalyst components forms the dispersed phase (discontinuous phase) in the form of dispersed droplets. The droplets are then solidified to form solid catalyst particles, and the solid particles are separated from the liquid and optionally washed and/or dried. The solvent forming the continuous phase may be immiscible to the catalyst solution at least at the conditions (e. g. temperatures) used during the dispersing step.

The term "immiscible with the catalyst solution" means that the solvent (continuous phase) is fully immiscible or partly immiscible i.e. not fully miscible with the dispersed phase solution.

Preferably said solvent is inert in relation to the compounds of the catalyst system to be produced. Full disclosure of the necessary process can be found in WO03/051934 which is herein incorporated by reference.

The inert solvent must be chemically inert at least at the conditions (e.g. temperature) used during the dispersing step. Preferably, the solvent of said continuous phase does not contain dissolved therein any significant amounts of catalyst forming compounds. Thus, the solid particles of the catalyst are formed in the droplets from the compounds which originate from the dispersed phase (i.e. are provided to the emulsion in a solution dispersed into the continuous phase).

The terms "immobilisation" and "solidification" are used herein interchangeably for the same purpose, i.e. for forming free flowing solid catalyst particles in the absence of an external porous particulate carrier, such as silica. The solidification happens thus within the droplets. Said step can be effected in various ways as disclosed in said WO03/051934 Preferably solidification is caused by an external stimulus to the emulsion system such as a temperature change to cause the solidification. Thus in said step the catalyst component (s) remain "fixed" within the formed solid particles. It is also possible that one or more of the catalyst components may take part in the solidification/immobilisation reaction.

Accordingly, solid, compositionally uniform particles having a predetermined particle size range can be obtained.

Furthermore, the particle size of the catalyst particles of the invention can be controlled by the size of the droplets in the solution, and spherical particles with a uniform particle size distribution can be obtained.

The invention is also industrially advantageous, since it enables the preparation of the solid particles to be carried out as a one-pot procedure. Continuous or semicontinuous processes are also possible for producing the catalyst.

Dispersed Phase

The principles for preparing two phase emulsion systems are known in the chemical field. Thus, in order to form the two phase liquid system, the solution of the catalyst component (s) and the solvent used as the continuous liquid phase have to be essentially immiscible at least during the dispersing step. This can be achieved in a known manner e.g. by choosing said two liquids and/or the temperature of the dispersing step/solidifying step accordingly.

A solvent may be employed to form the solution of the catalyst component (s). Said solvent is chosen so that it dissolves said catalyst component (s). The solvent can be preferably an organic solvent such as used in the field, comprising an optionally substituted hydrocarbon such as linear or branched aliphatic, alicyclic or aromatic hydrocarbon, such as a linear or cyclic alkane, an aromatic hydrocarbon and/or a halogen containing hydrocarbon.

Examples of aromatic hydrocarbons are toluene, benzene, ethylbenzene, propylbenzene, butylbenzene and xylene. Toluene is a preferred solvent. The solution may comprise one or more solvents. Such a solvent can thus be used to facilitate the emulsion formation, and usually does not form part of the solidified particles, but e.g. is removed after the solidification step together with the continuous phase.

Alternatively, a solvent may take part in the solidification, e.g. an inert hydrocarbon having a high melting point (waxes), such as above 40° C., suitably above 70° C., e. g. above 80° C. or 90° C., may be used as solvents of the dispersed phase to immobilise the catalyst compounds within the formed droplets.

In another embodiment, the solvent consists partly or completely of a liquid monomer, e.g. liquid olefin monomer designed to be polymerised in a "prepolymerisation" immobilisation step.

Continuous Phase

The solvent used to form the continuous liquid phase is a single solvent or a mixture of different solvents and may be immiscible with the solution of the catalyst components at least at the conditions (e.g. temperatures) used during the dispersing step. Preferably said solvent is inert in relation to said compounds.

The term "inert in relation to said compounds" means herein that the solvent of the continuous phase is chemically inert, i.e. undergoes no chemical reaction with any catalyst forming component. Thus, the solid particles of the catalyst are formed in the droplets from the compounds which originate from the dispersed phase, i.e. are provided to the emulsion in a solution dispersed into the continuous phase.

It is preferred that the catalyst components used for forming the solid catalyst will not be soluble in the solvent of the continuous liquid phase. Preferably, said catalyst components are essentially insoluble in said continuous phase forming solvent.

Solidification takes place essentially after the droplets are formed, i.e. the solidification is effected within the droplets e.g. by causing a solidifying reaction among the compounds present in the droplets. Furthermore, even if some solidifying agent is added to the system separately, it reacts within the droplet phase and no catalyst forming components go into the continuous phase.

The term "emulsion" used herein covers both bi- and multiphasic systems.

In a preferred embodiment said solvent forming the continuous phase is an inert solvent including a halogenated organic solvent or mixtures thereof, preferably fluorinated organic solvents and particularly semi, highly or perfluorinated organic solvents and functionalised derivatives thereof. Examples of the above-mentioned solvents are semi, highly or perfluorinated hydrocarbons, such as alkanes, alkenes and cycloalkanes, ethers, e.g. perfluorinated ethers and amines, particularly tertiary amines, and functionalised derivatives thereof. Preferred are semi, highly or perfluorinated, particularly perfluorinated hydrocarbons, e.g. perfluorohydrocarbons of e.g. C3-C30, such as C4-C10. Specific examples of suitable perfluoroalkanes and perfluorocycloalkanes include perfluoro-hexane, -heptane, -octane and -(methylcyclohexane). Semi fluorinated hydrocarbons relates particularly to semifluorinated n-alkanes, such as perfluoroalkyl-alkane.

"Semi fluorinated" hydrocarbons also include such hydrocarbons wherein blocks of —C—F and —C—H alternate. "Highly fluorinated" means that the majority of the —C—H units are replaced with —C—F units. "Perfluorinated" means that all —C—H units are replaced with —C—F units. See the articles of A. Enders and G. Maas in "Chemie in unserer Zeit", 34. Jahrg. 2000, Nr.6, and of Pierandrea Lo Nostro in "Advances in Colloid and Interface Science", 56 (1995) 245-287, Elsevier Science.

Dispersing Step

The emulsion can be formed by any means known in the art: by mixing, such as by stirring said solution vigorously to said solvent forming the continuous phase or by means of mixing mills, or by means of ultrasonic wave, or by using a so called phase change method for preparing the emulsion by first forming a homogeneous system which is then transferred by changing the temperature of the system to a biphasic system so that droplets will be formed.

The two phase state is maintained during the emulsion formation step and the solidification step, as, for example, by appropriate stirring.

Additionally, emulsifying agents/emulsion stabilisers can be used, preferably in a manner known in the art, for facilitating the formation and/or stability of the emulsion. For the said purposes e.g. surfactants, e.g. a class based on hydrocarbons (including polymeric hydrocarbons with a molecular weight e.g. up to 10 000 and optionally interrupted with a heteroatom(s)), preferably halogenated hydrocarbons, such as semi- or highly fluorinated hydrocarbons optionally having a functional group selected e.g. from —OH, —SH, $NH_2$, $NR''_2$, —COOH, —$COONH_2$, oxides of alkenes, —CR"=$CH_2$, where R" is hydrogen, or C1-C20 alkyl, C2-20-alkenyl or C2-20-alkynyl group, oxo-groups, cyclic ethers and/or any reactive derivative of these groups, like alkoxy, or carboxylic acid alkyl ester groups, or, preferably semi-, highly- or perfluorinated hydrocarbons having a functionalised terminal, can be used. The surfactants can be added to the catalyst solution, which forms the dispersed phase of the emulsion, to facilitate the forming of the emulsion and to stabilize the emulsion.

Alternatively, an emulsifying and/or emulsion stabilising aid can also be formed by reacting a surfactant precursor bearing at least one functional group with a compound reactive with said functional group and present in the catalyst solution or in the solvent forming the continuous phase. The obtained reaction product acts as the actual emulsifying aid and or stabiliser in the formed emulsion system.

Examples of the surfactant precursors usable for forming said reaction product include e.g. known surfactants which bear at least one functional group selected e.g. from —OH, —SH, $NH_2$, $NR''_2$. —COOH, —$COONH_2$, oxides of alkenes, —CR"=$CH_2$, where R" is hydrogen, or C1-C20 alkyl, C2-20-alkenyl or C2-20-alkynyl group, oxo-groups, cyclic ethers with 3 to 5 ring atoms, and/or any reactive derivative of these groups, like alkoxy or carboxylic acid alkyl ester groups; e.g. semi-, highly or perfluorinated hydrocarbons bearing one or more of said functional groups. Preferably, the surfactant precursor has a terminal functionality as defined above.

The compound reacting with such surfactant precursor is preferably contained in the catalyst solution and may be a further additive or one or more of the catalyst forming compounds. Such compound is e.g. a compound of group 13 (e.g. MAO and/or an aluminium alkyl compound and/or a transition metal compound).

If a surfactant precursor is used, it is preferably first reacted with a compound of the catalyst solution before the addition of the transition metal compound. In one embodiment e.g. a highly fluorinated C1-n (suitably C4-30- or C5-15) alcohol (e.g. highly fluorinated heptanol, octanol or nonanol), oxide (e.g. propenoxide) or acrylate ester is reacted with a cocatalyst to form the "actual" surfactant. Then, an additional amount of cocatalyst and the transition metal compound is added to said solution and the obtained solution is dispersed to the solvent forming the continuous phase. The "actual" surfactant solution may be prepared before the dispersing step or in the dispersed system. If said solution is made before the dispersing step, then the prepared "actual" surfactant solution and the transition metal solution may be dispersed successively (e. g. the surfactant solution first) to the immiscible solvent, or be combined together before the dispersing step.

Solidification

The solidification of the catalyst component(s) in the dispersed droplets can be effected in various ways, e.g. by causing or accelerating the formation of said solid catalyst forming reaction products of the compounds present in the droplets. This can be effected, depending on the used compounds and/or the desired solidification rate, with or without an external stimulus, such as a temperature change of the system.

In a particularly preferred embodiment, the solidification is effected after the emulsion system is formed by subjecting the system to an external stimulus, such as a temperature change. Temperature differences are typically of e.g. 5 to 100° C., such as 10 to 100° C., or 20 to 90° C., such as 50 to 90° C.

The emulsion system may be subjected to a rapid temperature change to cause a fast solidification in the dispersed system. The dispersed phase may e.g. be subjected to an immediate (within milliseconds to few seconds) temperature change in order to achieve an instant solidification of the component (s) within the droplets. The appropriate temperature change, i. e. an increase or a decrease in the temperature of an emulsion system, required for the desired solidification rate of the components cannot be limited to any specific range, but naturally depends on the emulsion system, i. a. on the used compounds and the concentrations/ratios thereof, as well as on the used solvents, and is chosen accordingly. It is also evident that any techniques may be used to provide sufficient heating or cooling effect to the dispersed system to cause the desired solidification.

In one embodiment the heating or cooling effect is obtained by bringing the emulsion system with a certain temperature to an inert receiving medium with significantly different temperature, e. g. as stated above, whereby said temperature change of the emulsion system is sufficient to cause the rapid solidification of the droplets. The receiving medium can be gaseous, e. g. air, or a liquid, preferably a solvent, or a mixture of two or more solvents, wherein the catalyst component (s) is (are) immiscible and which is inert in relation to the catalyst component (s). For instance, the receiving medium comprises the same immiscible solvent used as the continuous phase in the first emulsion formation step.

Said solvents can be used alone or as a mixture with other solvents, such as aliphatic or aromatic hydrocarbons, such as alkanes. Preferably a fluorinated solvent as the receiving medium is used, which may be the same as the continuous phase in the emulsion formation, e. g. perfluorinated hydrocarbon.

Alternatively, the temperature difference may be effected by gradual heating of the emulsion system, e. g. up to 10° C. per minute, preferably 0.5 to 6° C. per minute and more preferably in 1 to 5° C. per minute.

In case a melt of e. g. a hydrocarbon solvent is used for forming the dispersed phase, the solidification of the droplets may be effected by cooling the system using the temperature difference stated above.

Preferably, the "one phase" change as usable for forming an emulsion can also be utilised for solidifying the catalytically active contents within the droplets of an emulsion system by, again, effecting a temperature change in the dispersed system, whereby the solvent used in the droplets becomes miscible with the continuous phase, preferably a fluorous continuous phase as defined above, so that the droplets become impoverished of the solvent and the solidifying components remaining in the "droplets" start to solidify. Thus the immiscibility can be adjusted with respect to the solvents and conditions (temperature) to control the solidification step.

The miscibility of e.g. organic solvents with fluorous solvents can be found from the literature and be chosen accordingly by a skilled person. Also the critical temperatures needed for the phase change are available from the literature or can be determined using methods known in the art, e. g. the Hildebrand-Scatchard-Theorie. Reference is also made to the articles of A. Enders and G. and of Pierandrea Lo Nostro cited above.

Thus according to the invention, the entire or only part of the droplet may be converted to a solid form. The size of the "solidified" droplet may be smaller or greater than that of the original droplet, e. g. if the amount of the monomer used for the prepolymerisation is relatively large.

The solid catalyst particles recovered can be used, after an optional washing step, in a polymerisation process of an olefin. Alternatively, the separated and optionally washed solid particles can be dried to remove any solvent present in the particles before use in the polymerisation step. The separation and optional washing steps can be effected in a known manner, e. g. by filtration and subsequent washing of the solids with a suitable solvent.

The droplet shape of the particles may be substantially maintained. The formed particles may have an average size range of 1 to 500 µm, e.g. 5 to 500 µm, advantageously 5 to 200 µm or 10 to 150 µm. Even an average size range of 5 to 60 µm is possible. The size may be chosen depending on the polymerisation the catalyst is used for. Advantageously, the particles are essentially spherical in shape, they have a low porosity and a low surface area.

The formation of solution can be effected at a temperature of 0-100° C., e.g. at 20-80° C. The dispersion step may be effected at −20° C.-100° C., e.g. at about −10-70° C., such as at −5 to 30° C., e.g. around 0° C.

To the obtained dispersion an emulsifying agent as defined above, may be added to improve/stabilise the droplet formation. The solidification of the catalyst component in the droplets is preferably effected by raising the temperature of the mixture, e.g. from 0° C. temperature up to 100° C., e.g. up to 60-90° C., gradually. E.g. in 1 to 180 minutes, e.g. 1-90 or 5-30 minutes, or as a rapid heat change. Heating time is dependent on the size of the reactor.

During the solidification step, which is preferably carried out at about 60 to 100° C., preferably at about 75 to 95° C., (below the boiling point of the solvents) the solvents may preferably be removed and optionally the solids are washed with a wash solution, which can be any solvent or mixture of solvents such as those defined above and/or used in the art, preferably a hydrocarbon, such as pentane, hexane or heptane, suitably heptane. The washed catalyst can be dried or it can be slurried into an oil and used as a catalyst-oil slurry in polymerisation process.

All or part of the preparation steps can be done in a continuous manner. Reference is made to WO2006/069733 describing principles of such a continuous or semicontinuous preparation methods of the solid catalyst types, prepared via emulsion/solidification method.

Catalyst Off-Line Prepolymerisation

The use of the heterogeneous catalysts, where no external support material is used (also called "self-supported" catalysts) might have, as a drawback, a tendency to dissolve to some extent in the polymerisation media, i.e. some active catalyst components might leach out of the catalyst particles during slurry polymerisation, whereby the original good morphology of the catalyst might be lost. These leached catalyst components are very active possibly causing problems during polymerisation. Therefore, the amount of leached components should be minimized, i.e. all catalyst components should be kept in heterogeneous form.

Furthermore, the self-supported catalysts generate, due to the high amount of catalytically active species in the catalyst system, high temperatures at the beginning of the polymerisation which may cause melting of the product material. Both effects, i.e. the partial dissolving of the catalyst system and the heat generation, might cause fouling, sheeting and deterioration of the polymer material morphology.

In order to minimise the possible problems associated with high activity or leaching, it is preferred to "off line prepolymerise" the catalyst before using it in polymerisation process.

It has to be noted that off line prepolymerisation in this regard is part of the catalyst preparation process, being a step carried out after a solid catalyst is formed. The catalyst off line prepolymerisation step is not part of the actual polymerisation process configuration comprising a prepolymerisation step. After the catalyst off line prepolymerisation step, the solid catalyst can be used in polymerisation.

Catalyst "off line prepolymerisation" takes place following the solidification step of the liquid-liquid emulsion process. Pre-polymerisation may take place by known methods described in the art, such as that described in WO 2010/052263, WO 2010/052260 or WO 2010/052264. Preferable embodiments of this aspect of the invention are described herein.

As monomers in the catalyst off-line prepolymerisation step preferably alpha-olefins are used. Preferable $C_2$-$C_{10}$ olefins, such as ethylene, propylene, 1-butene, 1-pentene, 1-hexene, 4-methyl-1-pentene, 1-heptene, 1-octene, 1-nonene 1-decene, styrene and vinylcyclohexene are used. Most preferred alpha-olefins are ethylene and propylene, especially propylene.

The catalyst off-line prepolymerisation may be carried out in gas phase or in an inert diluent, typically oil or fluorinated hydrocarbon, preferably in fluorinated hydrocarbons or mixture of fluorinated hydrocarbons. Preferably perfluorinated hydrocarbons are used. The melting point of such (per) fluorinated hydrocarbons is typically in the range of 0 to 140° C., preferably 30 to 120° C., like 50 to 110° C.

Where the catalyst off line prepolymerisation is done in fluorinated hydrocarbons, the temperature for the pre-polymerisation step is below 70° C., e.g. in the range of −30 to 70° C., preferably 0-65° C. and more preferably in the range 20 to 55° C. Pressure within the reaction vessel is preferably higher than atmospheric pressure to minimize the eventual leaching of air and/or moisture into the catalyst vessel. Preferably the pressure is in the range of at least 1 to 15 bar, preferably 2 to 10 bar. The reaction vessel is preferably kept in an inert atmosphere, such as under nitrogen or argon or similar atmosphere.

Off line prepolymerisation is continued until the desired pre-polymerisation degree, defined as weight of polymer matrix/weight of solid catalyst before pre-polymerisation step, is reached. The degree is below 25, preferably 0.5 to 10.0, more preferably 1.0 to 8.0, most preferably 2.0 to 6.0.

Use of the off-line catalyst prepolymerisation step offers the advantage of minimising leaching of catalyst components and thus local overheating.

After off line prepolymerisation, the catalyst can be isolated and stored.

Polymerisation

The olefin polymerized using the catalyst of the invention is preferably propylene. The catalysts of the present invention are particularly suited for use in the manufacture of polypropylene polymers, either copolymers or homopolymers thereof.

As comonomers to propylene are preferably used ethylene or higher olefins, e.g. C4-C12 olefins, like 1-butene, 1-hexene, 1-octene or any mixtures thereof, more preferably ethylene or hexene. It is especially preferred if the copolymer is a propylene ethylene copolymer. The ethylene content in such a polymer may vary depending on the desired properties of the polymer. Especially, the catalysts of the present invention are used to manufacture propylene homopolymers or propylene random copolymers with ethylene as comonomer or propylene-hexene copolymers.

Polymerization in the method of the invention may be effected in one or more, e.g. 1, 2 or 3, polymerization reactors, using conventional polymerization techniques, e.g. gas phase, solution phase, slurry or bulk polymerization or combinations thereof, like a combination of a slurry and at least one gas phase reactor.

In case of propylene polymerisation for slurry reactors, the reaction temperature will generally be in the range 60 to 110° C. (e.g. 60-90° C.), the reactor pressure will generally be in the range 5 to 80 bar (e.g. 20-60 bar), and the residence time will generally be in the range 0.1 to 5 hours (e.g. 0.3 to 2 hours). The monomer is usually used as reaction medium.

For gas phase reactors, the reaction temperature used will generally be in the range 60 to 115° C. (e.g. 70 to 110° C.), the reactor pressure will generally be in the range 10 to 25 bar, and the residence time will generally be 0.5 to 8 hours (e.g. 0.5 to 4 hours). The gas used will be the monomer optionally as mixture with a non-reactive gas such as nitrogen or propane. In addition to actual polymerisation steps and reactors, the process can contain any additional polymerisation steps, like prepolymerisation step, and any further after reactor handling steps as known in the art.

For solution polymerization, an aliphatic or aromatic solvent can be used to dissolve the monomer and the polymer, and the polymerization temperature will generally be in the range 80 to 200° C. (e.g. 90 to 150° C.)

Generally the quantity of catalyst used will depend upon the nature of the catalyst, the reactor types and conditions and the properties desired for the polymer product. As is well known in the art hydrogen can be used for controlling the molecular weight of the polymer.

The metallocene catalysts of the invention possess excellent catalyst activity and good comonomer response. The catalysts are also able to provide polymers of high weight average molecular weight Mw.

Moreover, the random copolymerisation behaviour of metallocene catalysts of the invention shows a reduced tendency of chain transfer to ethylene. Polymers obtained with the metallocenes of the invention have normal particle morphologies.

In general therefore the invention catalysts can provide:
high activity in bulk propylene polymerisation;
very high molecular weight capability;
improved comonomer incorporation in propylene copolymers;
good polymer morphology.

It is a feature of the invention that the claimed catalysts enable the formation of polymers with high molecular weight. These features can be achieved at commercially interesting polymerisation temperatures, e.g. 60° C. or more. It is a preferred feature of the invention that the catalysts of the invention are used to polymerise propylene at a temperature of at least 60° C., preferably at least 65° C., such as at least 70° C.

The Mw of the polymers made using the catalysts of the invention may exceed 200,000, preferably at least 250,000, e.g. at least 350,000. Values of more than 500,000 have also been achieved. Mw/Mn values are generally low, e.g. less than 4, such as less than 3.5 or even less than 3.

Polypropylenes made by the metallocenes of the invention can be made with $MFR_{21}$ values in the range of 0.1 to 100 g/10 min depending on the amount of comonomer content and/or use and amount of hydrogen used as MFR regulating agent. ($MFR_{21}$ measured according to ISO1133, 230° C./21.6 kg load).

In other embodiments, polypropylenes made by the metallocenes of the invention can be made with $MFR_2$ values in the range of 0.1 to 50 g/10 min depending on the amount of comonomer content and/or use and amount of hydrogen used as MFR regulating agent. ($MFR_2$ measured according to ISO1133, 230° C./2.16 kg load)

The catalysts of the invention enable the formation of polypropylene homopolymers with low melting points, such as melting points less than 151.5° C., especially less than 151.0° C.

The polymers made by the catalysts of the invention are useful in all kinds of end articles such as pipes, films (cast, blown or BOPP films, such as for example BOPP for capacitor film), fibers, moulded articles (e.g. injection moulded, blow moulded, rotomoulded articles), extrusion coatings and so on.

The invention will now be illustrated by reference to the following non-limiting examples.

Analytical Tests

Measurement Methods:

Al and Zr Determination (ICP-Method)

The elementary analysis of a catalyst was performed by taking a solid sample of mass, M, cooling over dry ice. Samples were diluted up to a known volume, V, by dissolving in nitric acid ($HNO_3$, 65%, 5% of V) and freshly deionised (DI) water (5% of V). The solution was then added to hydrofluoric acid (HF, 40%, 3% of V), diluted with DI water up to the final volume, V, and left to stabilise for two hours.

The analysis was run at room temperature using a Thermo Elemental iCAP 6300 Inductively Coupled Plasma—Optical Emmision Spectrometer (ICP-OES) which was calibrated using a blank (a solution of 5% $HNO_3$, 3% HF in DI water), and 6 standards of 0.5 ppm, 1 ppm, 10 ppm, 50 ppm, 100 ppm and 300 ppm of Al, with 0.5 ppm, 1 ppm, 5 ppm, 20 ppm, 50 ppm and 100 ppm of Hf and Zr in solutions of 5% HNO3, 3% HF in DI water.

Immediately before analysis the calibration is 'resloped' using the blank and 100 ppm Al, 50 ppm Hf, Zr standard, a quality control sample (20 ppm Al, 5 ppm Hf, Zr in a solution of 5% HNO3, 3% HF in DI water) is run to confirm the reslope. The QC sample is also run after every 5th sample and at the end of a scheduled analysis set.

The content of hafnium was monitored using the 282.022 nm and 339.980 nm lines and the content for zirconium using 339.198 nm line. The content of aluminium was monitored via the 167.079 nm line, when Al concentration in ICP sample was between 0-10 ppm (calibrated only to 100 ppm) and via the 396.152 nm line for Al concentrations above 10 ppm.

The reported values are an average of three successive aliquots taken from the same sample and are related back to the original catalyst by inputting the original mass of sample and the dilution volume into the software.

DSC Analysis

Melting temperature $T_m$ was measured on approx. 5 mg samples with a Mettler-Toledo 822e differential scanning calorimeter (DSC), according to ISO11357-3 in a heat/cool/heat cycle with a scan rate of 10° C./min in the temperature range of +23 to +225° C. under a nitrogen flow rate of 50 ml $min^{-1}$. Melting temperature was taken as the endotherm peak, respectively in the second heating step. Calibration of the instrument was performed with $H_2O$, Lead, Tin, Indium, according to ISO 11357-1.

Melt Flow Rate

The melt flow rate (MFR) is determined according to ISO 1133 and is indicated in g/10 min. The MFR is an indication of the flowability, and hence the processability, of the polymer. The higher the melt flow rate, the lower the viscosity of the polymer. The MFR is determined at 230° C. and may be determined at different loadings such as 2.16 kg ($MFR_2$) or 21.6 kg ($MFR_{21}$).

GPC: Molecular weight averages, molecular weight distribution, and polydispersity index ($M_n$, $M_w$, $M_w/M_n$)

Molecular weight averages (Mw, Mn), Molecular weight distribution (MWD) and its broadness, described by polydispersity index, PDI=Mw/Mn (wherein Mn is the number average molecular weight and Mw is the weight average molecular weight) were determined by Gel Permeation Chromatography (GPC) according to ISO 16014-4:2003 and ASTM D 6474-99. A Waters GPCV2000 instrument, equipped with differential refractive index detector and online viscosimeter was used with 2× GMHXL-HT and 1× G7000HXL-HT TSK-gel columns from Tosoh Bioscience and 1,2,4-trichlorobenzene (TCB, stabilized with 250 mg/L 2,6-Di tert butyl-4-methyl-phenol) as solvent at 140° C. and at a constant flow rate of 1 mL/min. 209.5 µL of sample solution were injected per analysis. The column set was calibrated using universal calibration (according to ISO 16014-2:2003) with at least 15 narrow MWD polystyrene (PS) standards in the range of 1 kg/mol to 12 000 kg/mol. Mark Houwink constants for PS, PE and PP used are as per ASTM D 6474-99. All samples were prepared by dissolving 0.5-4.0 mg of polymer in 4 mL (at 140° C.) of stabilized TCB (same as mobile phase) and keeping for max. 3 hours at max. 160° C. with continuous gentle shaking prior sampling into the GPC instrument.

Quantification of Polypropylene Homopolymer Microstructure by NMR Spectroscopy

Quantitative nuclear-magnetic resonance (NMR) spectroscopy was used to quantify the isotacticity and content of regio-defects of the polypropylene homopolymers. Quantitative $^{13}C$ $\{^1H\}$ NMR spectra recorded in the solution-state using a Bruker Avance III 400 NMR spectrometer operating at 400.15 and 100.62 MHz for $^1H$ and $^{13}C$ respectively. All spectra were recorded using a $^{13}C$ optimised 10 mm selective excitation probehead at 125° C. using nitrogen gas for all pneumatics. Approximately 200 mg of material was dissolved in 1,1,2,2-tetrachloroethane-$d_2$ (TCE-$d_2$) inside a 10 mm NMR tube. This setup was chosen primarily for the high resolution needed for tacticity distribution quantification (Busico, V., Cipullo, R., Prog. Polym. Sci. 26 (2001) 443; Busico, V.; Cipullo, R., Monaco, G., Vacatello, M., Segre, A. L., Macromolecules 30 (1997) 6251). Standard single-pulse excitation was employed utilising the NOE and bi-level WALTZ16 decoupling scheme (Zhou, Z., Kuemmerle, R., Qiu, X., Redwine, D., Cong, R., Taha, A., Baugh, D. Winniford, B., J. Mag. Reson. 187 (2007) 225; Busico, V., Carbonniere, P., Cipullo, R., Pellecchia, R., Severn, J., Talarico, G., Macromol. Rapid Commun. 2007, 28, 11289). A total of 6144 (6k) transients were acquired per spectra using a 3 s recycle delay. Quantitative $^{13}C$ $\{^1H\}$ NMR spectra were processed, integrated and relevant quantitative properties determined from the integrals. All chemical shifts are internally referenced to the methyl signal of the isotactic pentad mmmm at 21.85 ppm.

The tacticity distribution was quantified through integration of the methyl region between 23.6 and 19.7 ppm correcting for any sites not related to the stereo sequences of interest (Busico, V., Cipullo, R., Prog. Polym. Sci. 26 (2001) 443; Busico, V., Cipullo, R., Monaco, G., Vacatello, M., Segre, A. L., Macromolecules 30 (1997) 6251). The pentad isotacticity was determined through direct integration of the methyl region and reported as either the mole fraction or percentage of isotactic pentad mmmm with respect to all steric pentads i.e. [mmmm]=mmmm/sum of all steric pentads. When appropriate integrals were corrected for the presence of sites not directly associated with steric pentads.

Characteristic signals corresponding to regio irregular propene insertion were observed (Resconi, L., Cavallo, L., Fait, A., Piemontesi, F., Chem. Rev. 2000, 100, 1253). The presence of secondary inserted propene in the form of 2.1 erythro regio defects was indicated by the presence of the two methyl signals at 17.7 and 17.2 ppm and confirmed by the presence of other characteristic signals. The amount of 2.1 erythro regio defects was quantified using the average integral (e) of the e6 and e8 sites observed at 17.7 and 17.2 ppm respectively, i.e. e=0.5*(e6+e8). Characteristic signals corresponding to other types of regio irregularity were not observed (Resconi, L., Cavallo, L., Fait, A., Piemontesi, F., Chem. Rev. 2000, 100, 1253). The amount of primary inserted propene (p) was quantified based on the integral of all signals in the methyl region (CH3) from 23.6 to 19.7 ppm paying attention to correct for other species included in the integral not related to primary insertion and for primary insertion signals excluded from this region such that p=CH3+2*e. The relative content of a specific type of regio defect was reported as the mole fraction or percentage of said regio defect with respect all observed forms of propene insertion i.e. sum of all primary (1,2), secondary (2,1) and tertiary (3,1) inserted propene units, e.g. [21e]=e/(p+e+t+i). The total amount of secondary inserted propene in the form of 2,1-erythro or 2,1-threo regio defects was quantified as sum of all said regio irregular units, i.e. [21]=[21e]+[21t].

Quantification of Copolymer Microstructure by NMR Spectroscopy

Quantitative nuclear-magnetic resonance (NMR) spectroscopy was used to quantify the comonomer content and comonomer distribution of the copolymers, specifically propene-co-ethylene copolymers. Quantitative $^{13}C$ $\{^1H\}$ NMR spectra recorded in the solution-state using a Bruker Advance III 400 NMR spectrometer operating at 400.15 and 100.62 MHz for $^1H$ and $^{13}C$ respectively. All spectra were recorded using a $^{13}C$ optimised 10 mm selective excitation probehead at 125° C. using nitrogen gas for all pneumatics. Approximately 200 mg of material was dissolved in 1,2-tetrachloroethane-$d_2$ (TCE-$d_2$) with chromium-(III)-acetylacetonate (Cr(acac)$_3$) resulting in a 65 mM solution of relaxation agent in solvent (Singh, G., Kothari, A., Gupta, V., Polymer Testing 28 5 (2009), 475). This setup was chosen primarily for the high resolution and quantitative spectra needed for accurate ethylene content determination. Standard single-pulse excitation was employed without NOE, using an optimised tip angle, 1 s recycle delay and bi-level WALTZ16 decoupling scheme (Zhou, Z., Kuemmerle, R., Qiu, X., Redwine, D., Cong, R., Taha, A., Baugh, D. Winniford, B., J. Mag. Reson. 187 (2007) 225; Busico, V., Carbonniere, P., Cipullo, R., Pellecchia, R., Severn, J., Talarico, G., Macromol. Rapid Commun. 2007, 28, 11289). A total of 6144 (6k) transients were acquired per spectra. Quantitative $^{13}C\{^1H\}$ NMR spectra were processed, integrated and relevant quantitative properties determined from the integrals using proprietary computer programs. All chemical shifts were indirectly referenced to the central methylene group of the ethylene block (EEE) at 30.00 ppm using the chemical shift of the solvent. This approach allowed comparable referencing even when this structural unit was not present.

Characteristic signals corresponding to regio irregular propene insertion were observed (Resconi, L., Cavallo, L., Fait, A., Piemontesi, F., Chem. Rev. 2000, 100, 1253.)].

Characteristic signals corresponding to the incorporation of ethylene were observed (Cheng, H. N., Macromolecules 17, 1984, 1950). The comonomer content was calculated as the mole fraction or percent of incorporated ethylene with respect to all monomer in the copolymer using the method of Wang et. al. (Wang, W.-J., Zhu, S., Macromolecules 33, 2000, 1157) through integration of multiple signals spanning the whole spectral $^{13}C$ spectra. This analyse method was chosen for its robust nature and ability to account for the presence of regio irregular propene insertion when needed. Integral regions were slightly adjusted to increase applicability across the whole range of encountered comonomer contents.

For systems where only isolated ethylene incorporation (PPEPP) was observed the method of Wang et. al. was modified to reduce the influence of non-zero integrals used to quantify higher order comonomer sequences. In such cases the term for the absolute ethylene content was determined based upon only $E=0.5(S\beta\beta+S\beta\gamma+S\beta\delta+0.5(S\alpha\beta+S\alpha\gamma))$ or $E=0.5(I_H+I_G+0.5(I_C+I_D))$ using the same notation as Wang et. al. (Wang, W.-J., Zhu, S., Macromolecules 33, 2000, 1157). The term used for absolute propylene content (P) was not modified and the mole fraction of ethylene calculated as $[E]=E/(E+P)$. The comonomer content in weight percent was calculated from the mole fraction in the usual way i.e. $[E \text{ wt \%}]=100*([E]*28.06)/(([E]*28.06)+((1-[E])*42.08))$.

1-Hexene Content (FT-IR)

The content of 1-hexene has been measured by FT-IR spectroscopy, by pressing a sample of the stabilized powder of the polymer to be analysed in an automated IR press as follows:

press temperature: 210° C.
melting time: 45 sec
press pressure: 3 steps (10/30/90 bar)
cooling rate: 12° C./min
de-moulding temperature: between 35 and 45° C.

| step | 1 | 2 | 3 | 4 | 5 (cooling) |
|---|---|---|---|---|---|
| duration (sec.) | 45 | 15 | 15 | 15 | 900 |
| Temperature (° C.) | 210 | 210 | 210 | 210 | 30 |
| pressure (bar) | 0 | 10 | 30 | 90 | 90 |

The films had a thickness of between 260 and 300 µm. Spectra were recorded in transmission mode with a spectral window of 5000 to 400 wavenumbers ($cm^{-1}$), a resolution of 2 $cm^{-1}$ and 16 scans. The C6 content of the C3C6 copolymers was determined using a thickness normalised method using the baseline corrected peak height of a quantitative band at 727 $cm^{-1}$, with the baseline defined from 758 to 705 $cm^{-1}$. The comonomer content was then predicted in wt % using previously determined linear calibration coefficients relating the absorption of the quantitative band ($I_{727}$) and the thickness (T) in cm of the pressed film. The prediction relation is:

$$\text{wt \% C6}=(I_{727}/T-0.035)/1.2071 \quad \text{(Equation 1)}$$

The result was reported as an average of two measurements.

EXAMPLES

Metallocene Synthesis

Reagents 2,6-Dimethylaniline (Acros), 1-bromo-3,5-dimethylbenzene (Acros), bis(2,6-diisopropylphenyl)imidazolium chloride (Aldrich), triphenylphosphine (Acros), Diethyl malonate (Acros), pivaldehyde (Acros), diethylamine (Acros), paraform (Acros), methanesulfonic acid (Aldrich), $Et_4NI$ (Acros), di-tert-butyl(2'-methyl-2-biphenyl)phosphine (Aldrich), acetic anhydride (Acros), $NiCl_2$ (DME) (Aldrich), dichlorodimethylsilane (Merck), $ZrCl_4$ (Merck), $ZrCl_4(THF)_2$ (Aldrich), trimethylborate (Acros), $Pd(OAc)_2$ (Aldrich), $NaBH_4$ (Acros), 2.5 M nBuLi in hexanes (Chemetal), KOH (Merck), $ZnCl_2$ (Merck), hydrogen gas (Linde), CuCN (Merck), 10% Pd/C (Merck), magnesium turnings (Acros), silica gel 60, 40-63 µm (Merck), bromine (Merck), 96% sulfuric acid (Reachim), sodium nitrite (Merck), copper powder (Alfa), potassium hydroxide (Merck), $K_2CO_3$ (Merck), 12 M HCl (Reachim), TsOH (Aldrich), $MgSO_4$ (Merck), $Na_2CO_3$ (Merck), $Na_2SO_3$ (Merck), $Na_2SO_4$ (Akzo Nobel), methanol (Merck), diethyl ether (Merck), 1,2-dimethoxyethane (DME, Aldrich), 95% ethanol (Merck), dichloromethane (Merck), hexane (Merck), THF (Merck), ethyl acetate (Merck), toluene (Merck) and diethyl ether (Merck) for extractions were used as received. DMF (Merck) was dried and distilled over $CaH_2$. Hexane, toluene and dichloromethane for organometallic synthesis were dried over molecular sieves 4A (Merck). Diethyl ether, THF, and 1,2-dimethoxyethane (Aldrich) for organometallic synthesis were distilled over sodium benzophenone ketyl. Toluene (Merck) and n-octane (Merck) for organometallic synthesis were kept and distilled over Na/K alloy. $CDCl_3$ (Deutero GmbH) and $CD_2Cl_2$ (Deutero GmbH) for NMR experiments were dried over $CaH_2$ and kept over 4A molecular sieves. 1-tert-Butyl-2-methoxybenzene was obtained from 2-tert-butylphenol (Merck) and dimethylsulfate (Merck) in the presence of 40% NaOH (Reachim) and "$Bu_4NBr$ (Acros) in dichloromethane as described in [Int. Pat. WO 2007116034, 2007, to Basell Polyolefine GmbH]. 4-Bromo-6-tert-butyl-5-methoxy-2-methylindan-1-one was obtained as described in WO2013/007650. 2-Methyltetrahydrofuran, 99%+ (Acros) was distilled over sodium benzophenone ketyl under argon atmosphere.

Synthesis of Comparative Metallocene MC-CE4

(3,5-Di-tert-butylphenyl)boronic acid

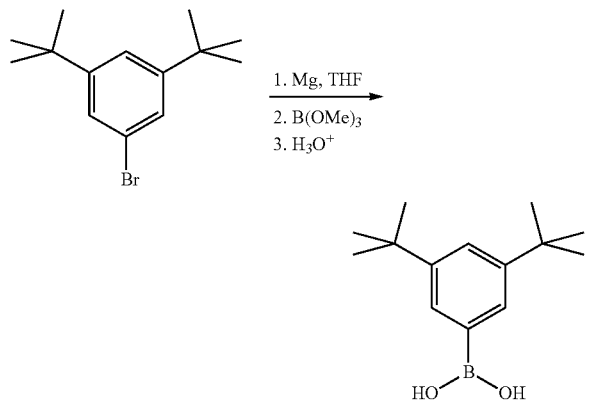

61 g (587 mmol, 1.22 eq.) of trimethylborate was added in one portion to a solution cooled to −78° C. of 3,5-di-tert-butylphenylmagnesium bromide obtained from a solution of 130.0 g (483 mmol) of 1-bromo-3,5-di-tert-butylbenzene in 900 ml of THF and 16.5 g (679 mmol, 1.41 eq.) of magnesium turnings. The resulting heterogeneous mixture was stirred for 2 h at room temperature and additionally refluxed for 2 h. The boronic ester was hydrolyzed by careful addition of a solution of 75 ml of conc. $H_2SO_4$ in 600 ml of water followed by 1 h of stirring at room temperature. The organic layer was separated, the aqueous layer was additionally extracted with 2×300 ml of diethyl ether. The combined organic extract was evaporated to dryness, and a solution of the residue in 1500 ml of diethyl ether was washed with 500 ml of water. The organic layer was separated, the aqueous layer was additionally extracted with 2×100 ml of diethyl ether. The combined organic extract was dried over $MgSO_4$ and then evaporated to dryness to give a white mass. The latter was triturated with 600 ml of n-hexane, the obtained suspension was filtered through a glass frit (G3), and the precipitate was dried in vacuo. This procedure gave 92.8 g of (3,5-di-tert-butylphenyl)boronic acid. The mother liquor was evaporated to dryness, and the residue was triturated with 100 ml of n-hexane. The following work-up procedure gave additional portion (6.8 g) of this boronic acid. Thus, the total yield of the title product was 99.5 g (88%).

$^1$NMR (CDCl$_3$): δ 7.92 (very br.s, 2H), 7.65 (br.s, 2H), 7.40 (br.s, 1H), 1.28 (s, 18H). $^{13}$C{$^1$H} NMR (CDCl$_3$): δ 148.8, 133 (m), 128.1, 123.5, 34.4, 31.4.

6-tert-Butyl-4-(3,5-di-tert-butylphenyl)-5-methoxy-2-methylindan-1-one

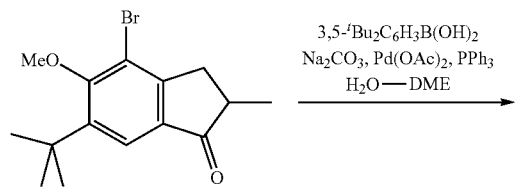

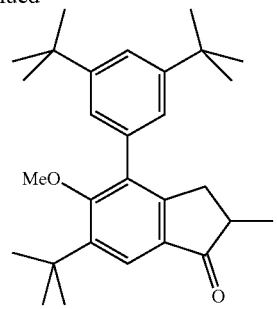

A mixture of 71.8 g (231 mmol) of 4-bromo-6-tert-butyl-5-methoxy-2-methylindan-1-one, 67.3 g (287 mmol, 1.25 eq.) of (3,5-di-tert-butylphenyl)boronic acid, 65.3 g (616 mmol) of Na$_2$CO$_3$, 2.70 g (12 mmol, 5 mol. %) of Pd(OAc)$_2$, 6.30 g (24 mmol, 10 mol. %) of PPh$_3$, 290 ml of water and 700 ml of 1,2-dimethoxyethane was refluxed for 6 h. The formed mixture was kept overnight at 0° C. The formed dark precipitate was filtered off, then 1 liter of dichloromethane and 1 liter of water were added to the precipitate. The organic layer was separated, the aqueous layer was additionally extracted with 2×200 ml of dichloromethane. The combined organic extract was dried over K$_2$CO$_3$ and then evaporated to dryness to give 108 g of black solid mass. This crude product was purified by flash chromatography on silica gel 60 (40-63 μm, hexanes-dichloromethane=1:1, vol., then, 1:2) to give 80.8 g (83%) of a slightly yellowish solid.

Anal. calc. for C$_{29}$H$_{40}$O$_2$: C, 82.81; H, 9.59. Found: C, 83.04; H, 9.75.

$^1$H NMR (CDCl$_3$): δ 7.74 (s, 1H), 7.41 (t, J=1.6 Hz, 1H), 7.24 (d, J=1.6 Hz 2H), 3.24 (s, 3H), 3.17 (dd, J=17.3 Hz, J=8.0 Hz, 1H), 2.64 (m, 1H), 2.47 (dd, J=17.3 Hz, J=3.7 Hz, 1H), 1.43 (s, 9H), 1.36 (s, 18H), 1.25 (d, J=7.3 Hz 3H).

5-tert-Butyl-7-(3,5-di-tert-butylphenyl)-6-methoxy-2-methyl-1H-indene

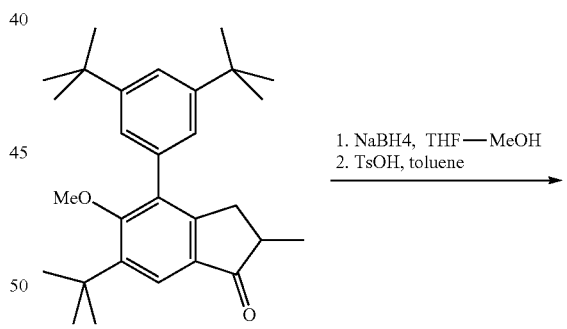

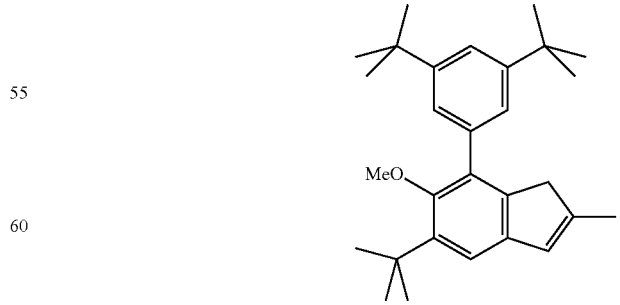

1.47 g (38.9 mmol) of NaBH$_4$ was added to a solution of 16.3 g (38.8 mmol) of 6-tert-butyl-4-(3,5-di-tert-butylphenyl)-5-methoxy-2-methylindan-1-one in 200 ml of THF cooled to 5° C. Then, 80 ml of methanol was added dropwise to this mixture by vigorous stirring for ca. 7 h at 5° C. The resulting mixture was evaporated to dryness, and the residue was treated by 300 ml of dichloromethane and 300 ml of 2 M HCl. The organic layer was separated, the aqueous layer was additionally extracted with 100 ml of dichloromethane. The combined organic extract was evaporated to dryness to give a colorless oil. To a solution of this oil in 250 ml of toluene 0.1 g of TsOH was added, this mixture was refluxed with Dean-Stark head for 15 min and then cooled to room temperature using water bath. The resulting solution was washed by 10% aqueous $Na_2CO_3$. The organic layer was separated, the aqueous layer was extracted with 2×50 ml of dichloromethane. The combined organic extract was dried over $K_2CO_3$ and then passed through a short layer of silica gel 60 (40-63 μm). The silica gel layer was additionally washed by 100 ml of dichloromethane. The combined organic elute was evaporated to dryness to give 15.7 g (99%) of a white crystalline product which was further used without additional purification.

Anal. calc. for $C_{29}H_{40}O$: C, 86.08; H, 9.96. Found: C, 86.26; H, 10.21.

$^1$H NMR ($CDCl_3$): δ 7.36 (t, J=1.8 Hz, 1H), 7.33 (d, J=1.8 Hz, 2H), 7.21 (s, 1H), 6.44 (m, 1H), 3.17 (s, 3H), 3.14 (s, 2H), 2.06 (s, 3H), 1.44 (s, 9H), 1.35 (s, 18H). $^{13}C\{^1H\}$ NMR ($CDCl_3$): δ 150.4, 145.2 (two resonances), 141.7, 140.9, 140.6, 137.3, 132.5, 126.9, 124.0, 120.1, 116.9, 60.2, 43.0, 35.2, 34.9, 31.5, 31.0, 16.7.

Bis[6-tert-butyl-4-(3,5-di-tert-butylphenyl)-5-methoxy-2-methyl-1H-inden-1-yl]dimethylsilane 10.0 ml (25.0 mmol) of 2.5 M $^n$BuLi in hexanes was added in one portion to a solution of 10.12 g (25.01 mmol) of 5-tert-butyl-7-(3,5-di-tert-butylphenyl)-6-methoxy-2-methyl-1H-indene in 200 ml of ether at −50° C. This mixture was stirred at room temperature for 4 h, then the resulting slightly yellowish suspension with a lot of precipitate was cooled to −50° C., and 200 mg of CuCN was added. The resulting mixture was stirred for 30 min at −25° C., and 1.61 g (12.48 mmol) of dichlorodimethylsilane was added in one portion. Then, this mixture was stirred overnight at ambient temperature. This solution was filtered through a pad of silica gel 60 (40-63 μm) which was additionally washed by 2×50 ml of dichloromethane. The combined filtrate was evaporated under a reduced pressure, and the residue was dried in vacuum at elevated temperature. This procedure gave 10.9 g (~100%) of bis[6-tert-butyl-4-(3,5-di-tert-butylphenyl)-5-methoxy-2-methyl-1H-inden-1-yl]dimethylsilane as a slightly yellowish glassy solid (>90% purity on the evidence of NMR spectroscopy, a ca. 7:3 mixture of the stereoisomers) which was further used without additional purification.

$^1$H NMR ($CDCl_3$): δ 7.57 (s), 7.40-7.45 (m) and 7.40 (s) {sum 8H}, 6.56 (s, 2H), 3.73 and 3.68 (2s, sum 2H), 3.25 (s, 6H), 2.23 and 2.22 (2s, sum 6H), 1.50, 1.49 and 1.43 (3s, sum 54H), −0.09, −0.10 and −0.17 (3s, sum 6H).

Rac-dimethylsilanediyl-bis[2-methyl-4-(3,5-di-tert-butylphenyl)-5-methoxy-6-tert-butyl-inden-1-yl] zirconium dichloride (MC-CE4)

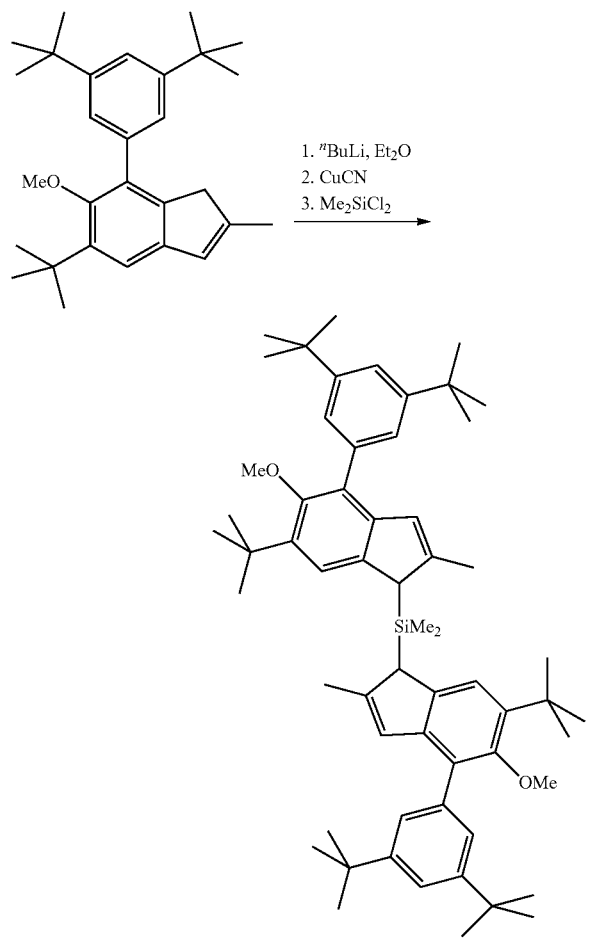

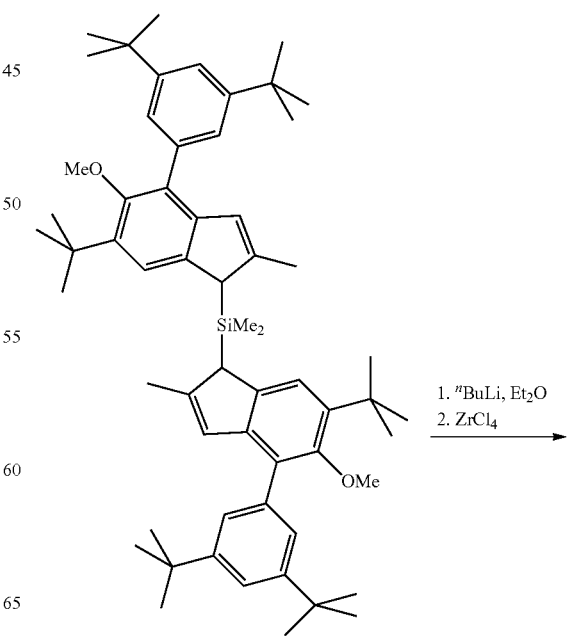

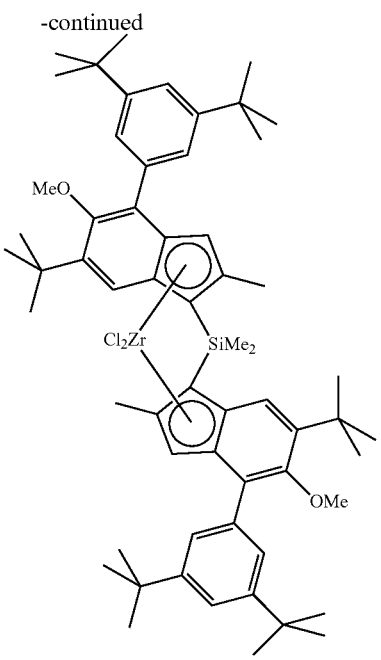

10.0 ml (25.0 mmol) of 2.5 M "BuLi in hexanes was added in one portion to a solution of 10.9 g (~12.5 mmol) of bis[6-tert-butyl-4-(3,5-di-tert-butylphenyl)-5-methoxy-2-methyl-1H-inden-1-yl]dimethylsilane (as prepared above) in 200 ml of ether cooled to −50° C. This mixture was stirred overnight at room temperature, then it was cooled again to −50° C., and 2.91 g (12.49 mmol) of ZrCl$_4$ was added. The reaction mixture was stirred for 24 h resulting in a reddish-orange solution with orange-yellow precipitate. The resulting mixture was evaporated to dryness, and the residue was heated with 150 ml of toluene. This hot mixture was filtered through glass frit (G4) to give a filtrate including on the evidence of NMR spectroscopy a ca. 65 to 35 mixture of rac- and meso-zirconocenes. This filtrate was evaporated to 50 ml and heated to dissolve the formed precipitate. Crystals precipitated at room temperature overnight were collected, washed with 25 ml of a ca. 1 to 1 mixture of toluene and n-hexane, 2×10 ml of n-hexane, and then dried in vacuo. This procedure gave 1.49 g of pure rac-zirconocene. The mother liquor was evaporated to ca. 50 ml, and 10 ml of n-hexane was added. Crystals precipitated at room temperature overnight were collected and dried in vacuo. This procedure gave 260 mg of rac-zirconocene. Again the mother liquor was evaporated to ca. 30 ml, heated to the boiling point, and 30 ml of n-hexane was added. Orange crystals precipitated at room temperature overnight were collected and dried in vacuo. This procedure gave one more portion of 3.17 g of rac-zirconocene. Thus, the total yield of rac-zirconocene isolated in this synthesis was 4.92 g (38%). The mother liquor was evaporated to ca. 10 ml, heated to the boiling point, and 10 ml of n-hexane was added. Red crystals precipitated at room temperature for 3 h were collected and dried in vacuum. This procedure gave 1.63 g (13%) of meso-zirconocene contaminated with ca. 2% of rac-form. Crystals precipitated from the mother liquor at room temperature overnight were collected and dried in vacuum. This procedure gave 2.46 g of a ca. 65:35 mixture of rac- and meso-zirconocenes. Thus, the total yield of rac- and meso-zirconocenes isolated in this synthesis was 9.01 g (70%).

Rac-MC-CE4.

Anal. calc. for $C_{60}H_{82}Cl_2O_2SiZr$: C, 70.27; H, 8.06. Found: C, 70.42; H, 8.25.

$^1$H NMR (CD$_2$Cl$_2$, −20° C.): δ 7.60 (br.s, 2H), 7.51 (br.s, 2H), 7.36 (t, J=1.6 Hz, 2H), 7.34 (br.s, 2H), 6.49 (s, 2H), 3.28 (s, 6H), 2.12 (s, 6H), 1.37 (s, 18H), 1.33 (s, 18H), 1.29 (s, 18H), 1.29 (s, 6H). $^{13}$C{$^1$H} NMR (CD$_2$Cl$_2$, −20° C.): δ 160.18, 151.29, 150.70, 144.06, 136.19, 135.21, 133.87, 127.60, 124.97, 124.34, 123.45, 121.16, 120.92, 120.79, 82.22, 62.63, 35.99, 35.30, 35.11, 31.56, 30.38, 18.67, 2.53.[1]

[1] In $^{13}$C NMR spectrum pairs of the resonances (151.29 and 150.70), (124.97 and 124.34) and (35.11 and 35.30) merge into the broad singlets.

Meso-MC-CE4.

Anal. calc. for $C_{60}H_{82}Cl_2O_2SiZr$: C, 70.27; H, 8.06. Found: C, 70.14; H, 8.11.

$^1$H NMR (CD$_2$Cl$_2$, −20° C.): δ 7.71 (br.s, 2H), 7.42 (br.s, 2H), 7.37 (br.t, 2H), 7.34 (br.s, 2H), 6.49 (s, 2H), 3.12 (s, 6H), 2.37 (s, 6H), 1.41 (s, 3H), 1.35 (s, 18H), 1.35 (s, 18H), 1.31 (s, 18H), 1.20 (s, 3H). $^{13}$C{$^1$H} NMR (CD$_2$Cl$_2$, −20° C.): δ 158.99, 151.19, 150.62, 143.84, 136.44, 135.93, 135.01, 127.28, 125.33, 124.73, 124.56, 122.70, 120.86, 120.49, 84.15, 62.14, 35.91, 35.38, 35.09, 31.66, 31.54, 30.59, 18.82, 3.01, 2.53.

Synthesis of Comparative Metallocene MC-CE5

4-Bromo-2,6-dimethylaniline

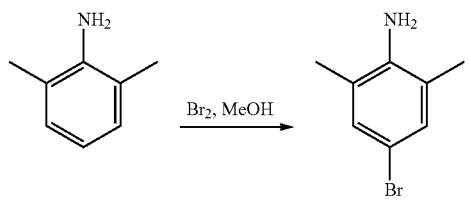

159.8 g (1.0 mol) of bromine was slowly (over 2 h) added to a stirred solution of 121.2 g (1.0 mol) of 2,6-dimethylaniline in 500 ml of methanol. The resulting dark-red solution was stirred overnight at room temperature, then poured into a cold solution of 140 g (2.5 mol) of potassium hydroxide in 1100 ml of water. The organic layer was separated, and the aqueous one was extracted with 500 ml of diethyl ether. The combined organic extract was washed with 1000 ml of water, dried over K$_2$CO$_3$, and evaporated in vacuum to give 202.1 g of 4-bromo-2,6-dimethylaniline (purity ca. 90%) as dark-red oil which crystallized upon standing at room temperature. This material was further used without additional purification.

$^1$H NMR (CDCl$_3$): δ 7.04 (s, 2H), 3.53 (br.s, 2H), 2.13 (s, 6H).

1-Bromo-3,5-dimethylbenzene

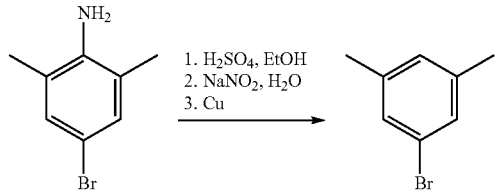

97 ml (1.82 mol) of 96% sulfuric acid was added dropwise to a solution of 134.7 g (ca. 673 mmol) of 4-bromo-2,6-dimethylaniline (prepared above, purity ca. 90%) in 1400 ml of 95% ethanol cooled to −10° C., at a such a rate to maintain the reaction temperature below 7° C. After the addition was complete, the solution was stirred at room temperature for 1 h. Then, the reaction mixture was cooled in an ice-bath, and a solution of 72.5 g (1.05 mol) of sodium nitrite in 150 ml of water was added dropwise over ca. 1 h. The formed solution was stirred at the same temperature for 30 min. Then the cooling bath was removed, and 18 g of copper powder was added. Upon completion of the rapid evolution of nitrogen additional portions (ca. 5 g each, ca. 50 g in total) of copper powder were added with 10 min intervals until gas evolution ceased completely. The reaction mixture was stirred at room temperature overnight, then filtered through a glass frit (G3), diluted with two-fold volume of water, and the crude product was extracted with 4×150 ml of dichloromethane. The combined extract was dried over $K_2CO_3$, evaporated to dryness, and then distilled in vacuum (b.p. 60-63° C./5 mm Hg) to give a yellowish liquid. This product was additionally purified by flash-chromatography on silica gel 60 (40-63 µm; eluent: hexane) and distilled once again (b.p. 51-52° C./3 mm Hg) to give 63.5 g (51%) of 1-bromo-3,5-dimethylbenzene as a colorless liquid.

$^1$H NMR (CDCl$_3$): δ 7.12 (s, 2H), 6.89 (s, 1H), 2.27 (s, 6H). $^{13}$C {$^1$H} NMR (CDCl$_3$): δ 139.81, 129.03, 128.61, 122.04, 20.99.

4-(3,5-Dimethylphenyl)-1-methoxy-2-methylindane romethane and 1000 ml of 1 M HCl were added to the residue. The organic layer was separated, and the aqueous layer was extracted with 150 ml of dichloromethane. The combined organic extract was evaporated to dryness to give a slightly greenish oil. The product was isolated by flash-chromatography on silica gel 60 (40-63 µm; eluent: hexane-dichloromethane=2:1, vol., then 1:2, vol.). This procedure gave 73.2 g (92%) of 4-(3,5-dimethylphenyl)-1-methoxy-2-methylindane as a colorless oil consisting of a mixture of diastereomers.

Anal. calc. for $C_{19}H_{22}O$: C, 85.67; H, 8.32. Found: C, 85.80; H, 8.26.

$^1$H NMR (CDCl$_3$), Syn-isomer: δ 7.35-7.22 (m, 3H), 7.05 (br.s, 2H), 6.97 (br.s, 1H), 4.52 (d, J=5.7 Hz, 1H), 3.44 (s, 3H), 2.92 (dd, J=15.7 Hz, J=7.1 Hz, 1H), 2.81 (dd, J=15.7 Hz, J=6.9 Hz, 1H), 2.60-2.48 (m, 1H), 2.35 (s, 6H), 1.08 (d, J=6.9 Hz, 3H); Anti-isomer: δ 7.37-7.31 (m, 1H), 7.30-7.25 (m, 2H), 7.04 (br.s, 2H), 6.97 (br.s, 1H), 4.43 (d, J=4.1 Hz, 1H), 3.49 (s, 3H), 3.29 (dd, J=17.3 Hz, J=8.9 Hz, 1H), 2.54-2.42 (m, 2H), 2.35 (s, 6H), 1.12 (d, J=6.7 Hz, 3H). $^{13}$C{$^1$H} NMR (CDCl$_3$), Syn-isomer: δ 143.29, 141.24, 140.75, 138.87, 137.65, 128.53, 128.39, 126.40 (two resonances), 123.95, 86.15, 56.69, 39.02, 38.25, 21.35, 13.50; Anti-isomer: δ 142.76, 140.76, 140.63, 138.97, 137.67, 128.61, 128.56, 126.75, 126.38, 124.04, 91.34, 56.52, 39.98, 38.33, 21.35, 19.04.

7-(3,5-Dimethylphenyl)-2-methyl-1H-indene

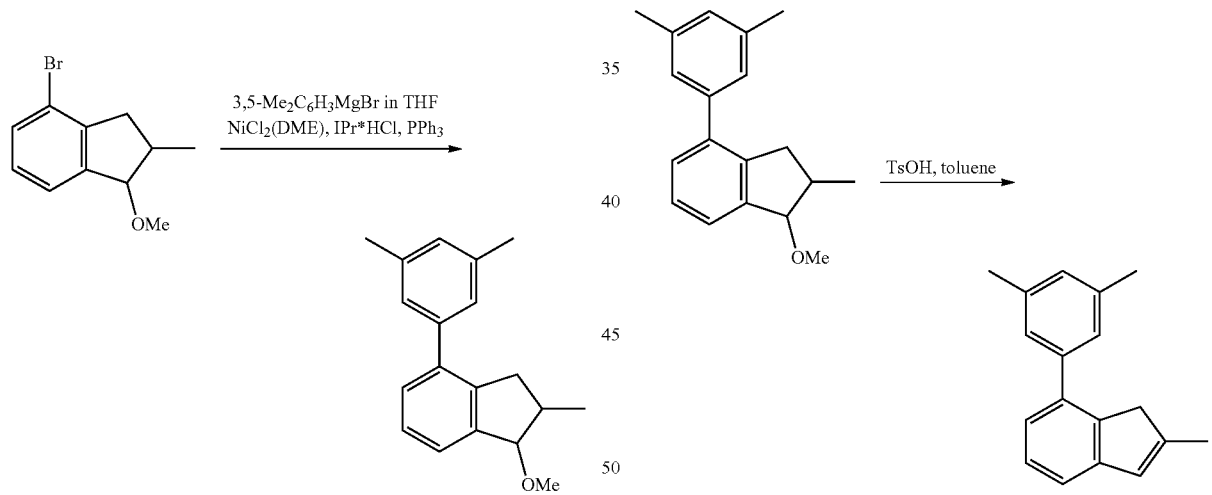

8.0 ml (8.0 mmol) of 1 M 3,5-dimethylphenylmagnesium bromide in THF (prepared from 1-bromo-3,5-dimethylbenzene and magnesium turnings in THF) was added to 2.55 g (6.0 mmol) of bis(2,6-diisopropylphenyl)imidazolium chloride, and the resulting mixture was stirred at room temperature for 10 min. Then, 1.57 g (6.0 mmol) of triphenylphosphine and 1.32 g (6.0 mmol) of NiCl$_2$(DME) were added successively. After stirring for 10 min, 72.3 g (300 mmol) of 4-bromo-1-methoxy-2-methylindane was added followed by 400 ml (400 mmol) of 1 M 3,5-dimethylphenylmagnesium bromide in THF. The latter was added at a such rate to maintain a gentle reflux. The resulting solution was additionally refluxed for 2 h, then cooled to room temperature, and 200 ml of water was added. The main part of THF was distilled off using rotary evaporator, then 500 ml of dichlo- 370 mg of TsOH was added to a solution of 73.2 g (275 mmol) of 4-(3,5-dimethylphenyl)-1-methoxy-2-methylindane in 700 ml of toluene, and the resulting mixture was refluxed using Dean-Stark head for 15 min. Then, one more portion of 370 mg of TsOH was added, and again the formed solution was refluxed using Dean-Stark head for an additional 15 min. After cooling to room temperature the reaction mixture was washed with 200 ml of 10% $K_2CO_3$. The organic layer was separated, and the aqueous layer was additionally extracted with 2×100 ml of dichloromethane. The combined organic extract was dried over anhydrous $K_2CO_3$, passed through a short pad of silica gel 60 (40-63 µm), and then evaporated to dryness to give a yellow oil. This oil was distilled in vacuum to give 62.0 g (96%) of 7-(3,5-dimethylphenyl)-2-methyl-1H-indene as yellowish oil (b.p. 166-175° C./5 mm Hg) which completely crystallized upon standing at room temperature.

Anal. calc. for $C_{18}H_{18}$: C, 92.26; H, 7.74. Found: C, 92.04; H, 7.72.

$^1$H NMR (CDCl$_3$): δ 7.27 (t, J=7.5 Hz, 1H), 7.21 (dd, J=7.5 Hz, J=1.0 Hz, 1H), 7.13 (br.s, 2H), 7.09 (dd, J=7.5 Hz, J=1.2 Hz, 1H), 6.98 (br.s, 1H), 6.51 (m, 1H), 3.36 (s, 2H), 2.36 (s, 6H), 2.12 (s, 3H). $^{13}$C{$^1$H} NMR (CDCl$_3$): δ 146.32, 146.20, 141.31, 140.73, 137.78, 137.55, 128.61, 127.14, 126.84, 126.27, 124.23, 118.72, 42.75, 21.39, 16.68.

Bis[4-(3,5-dimethylphenyl)-2-methyl-1H-inden-1-yl]dimethylsilane

6H), −0.18, −0.21, −0.24 (3s, sum 6H). $^{13}$C{$^1$H} NMR (CDCl$_3$): δ 147.48, 147.37, 145.42, 145.38, 142.91, 142.88, 141.30, 137.80, 134.38, 134.32, 128.41, 126.77, 126.15, 126.09, 125.55, 123.03, 122.94, 122.03, 121.97, 47.57, 47.51, 21.43, 18.00, −5.62, −6.00.

Rac-dimethylsilanediyl-bis[2-methyl-4-(3,5-dimethylphenyl)-inden-1-yl]zirconium dichloride (MC-CE5)

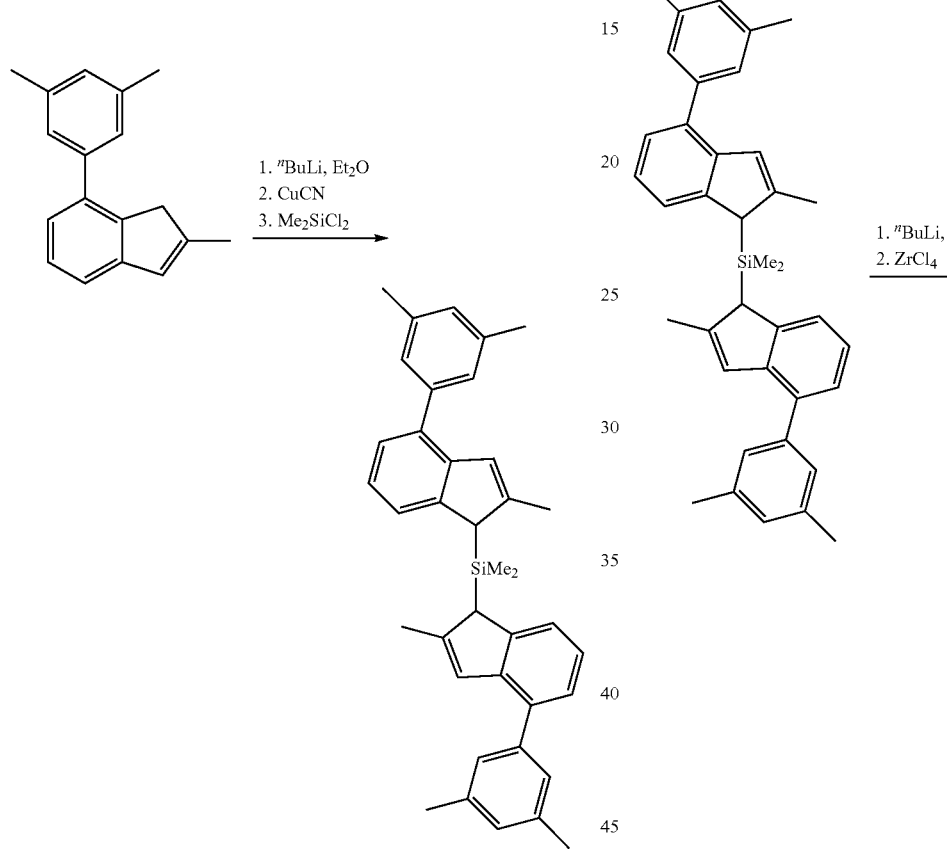

26.6 ml (66.5 mmol) of 2.5 M $^n$BuLi in hexanes was added in one portion to a solution of 15.53 g (66.3 mmol) of 7-(3,5-dimethylphenyl)-2-methyl-1H-indene in 300 ml of ether at −50° C. This mixture was stirred overnight at room temperature, then cooled to −40° C., and 300 mg of CuCN was added. The resulting mixture was stirred for 30 min at −25° C., and then 4.28 g (33.16 mmol) of dichlorodimethylsilane was added in one portion. This mixture was stirred overnight at ambient temperature, then filtered through a pad of silica gel 60 (40-63 μm) which was additionally washed with 2×50 ml of dichloromethane. The combined filtrate was evaporated under reduced pressure, and the residue was dried in vacuum at elevated temperature. This procedure gave 17.75 g (~100%) of bis[4-(3,5-dimethylphenyl)-2-methyl-1H-inden-1-yl]dimethylsilane (>90% purity by NMR, approx. 1:1 mixture of isomers) as slightly orange glassy solid which was further used without additional purification.

$^1$H NMR (CDCl$_3$): δ 7.50-6.76 (set of signals, sum 14H), 3.83, 3.79 (2s, sum 2H), 2.40 (s, 12H), 2.24, 2.21 (2s, sum 26.6 ml (66.5 mmol) of 2.5 M $^n$BuLi in hexanes was added in one portion to a solution of 17.75 g (~33.8 mmol) of bis[4-(3,5-dimethylphenyl)-2-methyl-1H-inden-1-yl]dimethylsilane (prepared above) in 350 ml of ether cooled to −50° C. This mixture was stirred overnight at room temperature. The resulting yellow solution with a lot of precipitate was cooled to −50° C., and 7.88 g (33.8 mmol) of ZrCl$_4$ was added. The reaction mixture was stirred for 24 h, then evaporated to dryness, and the residue was heated with 700 ml of toluene. This mixture was filtered while hot through a glass frit (G4). The precipitate on the glass frit was extracted with hot toluene (3×400 ml) in the following manner: toluene was heated with the precipitate, the formed suspension was filtered while hot, the filtrate was allowed to stand overnight at room temperature, then the formed precipitate was separated by decantation, and the decanted solution was then used for one more extraction. The combined orange precipitate was washed by 10 ml of toluene, then 2×10 ml of n-hexane, and dried in vacuum. This procedure gave 2.25 g of pure rac-dimethylsilanediylbis[$\eta^5$-4-(3,5-dimethylphenyl)-2-methyl-1H-inden-1-yl]zirconium dichloride. Additionally, 13.24 g of the a ca. 1:2 mixture of rac-/meso-complexes was obtained from 700 ml of the mother liquor originated from the first extraction. Thus, the total yield of rac- and meso-dimethylsilanediylbis[$\eta^5$-4-(3,5-dimethylphenyl)-2-methyl-1H-inden-1-yl]zirconium dichlorides isolated in this synthesis was 15.49 g (67%).

Rac-dimethylsilanediyl-bis[$\eta^5$-4-(3,5-dimethylphenyl)-2-methyl-1H-inden-1-yl]zirconium dichloride Anal. calc. for $C_{38}H_{38}Cl_2SiZr$: C, 66.64; H, 5.59. Found: C, 66.83; H, 5.70.

$^1$H NMR (CDCl$_3$): δ 7.63 (d, J=8.7 Hz, 1H), 7.37 (d, J=7.1 Hz, 1H), 7.28 (br.s, 2H), 7.09 (dd, J=8.7 Hz, J=7.1 Hz, 1H), 6.98, 6.97 (2s, sum 2H), 2.33 (s, 6H), 2.27 (s, 3H), 1.33 (s, 3H).

Synthesis of Comparative Metallocene MC-CE6

4-Bromo-2,6-diisopropylaniline

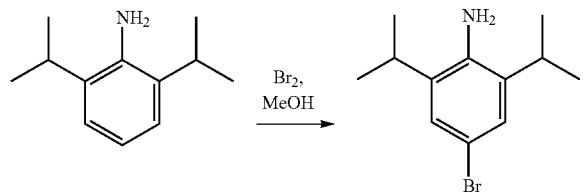

49 ml (152 g, 954 mmol) of bromine was slowly (for 2 h) added to a stirred solution of 169.7 g (957 mmol) of 2,6-diisopropylaniline in 1500 ml of methanol. The resulting dark-red solution was stirred overnight at room temperature, then most of methanol was removed under reduced pressure, and 1000 ml of dichloromethane was added to the residue. This solution was shaken with a cold solution of 140 g (2.5 mol) of potassium hydroxide in 1100 ml of water. The organic layer was separated, and the aqueous one was extracted with 200 ml of dichloromethane. The combined organic extract was dried over K$_2$CO$_3$, passed through a short layer of silica gel 60 (40-63 μm), and evaporated in vacuum to give crude 4-bromo-2,6-diisopropylaniline (purity ca. 90%) as dark-red oil which was further used without an additional purification.

$^1$H NMR (CDCl$_3$): δ 7.15 (s, 2H), 3.82 (br.s, 2H), 2.90 (sept, J=6.9 Hz, 2H), 1.28 (d, J=6.9 Hz, 12H). $^{13}$C{$^1$H} NMR (CDCl$_3$): δ 139.15, 134.55, 125.65, 111.08, 27.92, 22.16.

1-Bromo-3,5-diisopropylbenzene

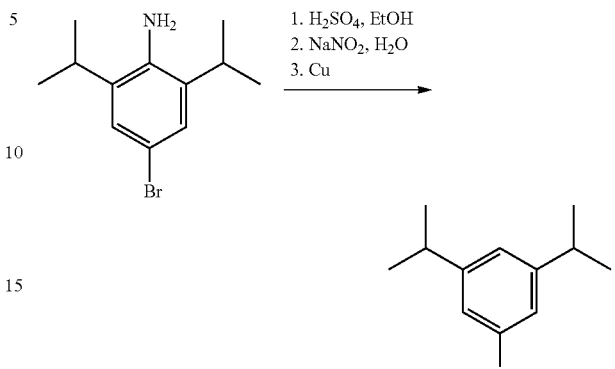

138 ml (2.59 mol) of 96% sulfuric acid was added dropwise to a solution of 4-bromo-2,6-diisopropylaniline (as prepared above, purity ca. 90%) in 2000 ml of 95% ethanol cooled to −10° C. at such a rate to keep the reaction temperature below 7° C. After the addition was complete, the formed solution was stirred at room temperature for 1 h. Then, the reaction mixture was cooled in an ice-bath, and a solution of 103.1 g (1.49 mol) of sodium nitrite in 215 ml of water was added dropwise over ca. 1 h. The formed solution was stirred at the same temperature for 30 min. Further on, the cooling bath was removed, and 18 g of copper powder was added. Upon completion of the rapid evolution of nitrogen additional portions (ca. 5 g each, ca. 70 g in total) of copper powder were added with 10 min intervals until gas evolution ceased completely. The reaction mixture was stirred at room temperature overnight, then filtered through glass frit (G3), diluted with two-fold volume of water, and crude product was extracted with 4×200 ml of dichloromethane. The combined extract was dried over K$_2$CO$_3$, evaporated to dryness, and then distilled in vacuum (b.p. up to 120° C./5 mm Hg) to give a yellowish liquid. This product was additionally purified by flash-chromatography on silica gel 60 (40-63 μm; eluent: hexane) and distilled once again (b.p. 85-99° C./5 mm Hg) to give 120.0 g (52%) of 1-bromo-3,5-diisopropylbenzene as a colorless liquid.

$^1$H NMR (CDCl$_3$): δ 7.19 (d, J=1.2 Hz, 2H), 6.99 (br.t, 1H), 2.86 (sept, J=6.9 Hz, 2H), 1.24 (d, J=6.9 Hz, 12H). $^{13}$C{$^1$H} NMR (CDCl$_3$): δ 151.04, 126.85, 123.70, 122.34, 34.06, 23.87.

(3,5-Diisopropylphenyl)boronic acid

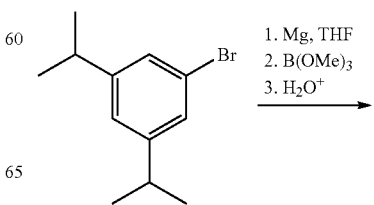

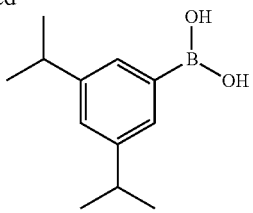

A solution of 3,5-diisopropylphenylmagnesium bromide obtained from a solution of 60.3 g (250 mmol) of 1-bromo-3,5-diisopropylbenzene in 400 ml of THF and 7.9 g (325 mmol, 30% excess) of magnesium turnings was cooled to −50° C. (some white solid was precipitated), and 39 g (375.3 mmol, 1.5 eq.) of trimethylborate was added in one portion. The resulting heterogeneous mixture was stirred overnight at room temperature. The boronic ester was hydrolyzed by careful addition of a mixture of 50 ml of 12 M HCl with 900 ml of water. The resulting mixture was stirred over 0.5 h. Then, it was filtered through a glass frit (G3) and extracted with 800 ml of diethyl ether. The organic layer was separated, and the aqueous layer was additionally extracted with 400 ml of diethyl ether. The combined organic extract was dried over $Na_2SO_4$ and then evaporated to dryness to give white mass. The latter was triturated with 300 ml of hexane, filtered through glass frit (G3) and dried in vacuo. This procedure gave 40.0 g (78%) of (3,5-diisopropylphenyl)boronic acid.

Anal. calc. for $C_{12}H_{19}BO_2$: C, 69.94; H, 9.29. Found: C, 69.41; H, 9.70.

$^1$H NMR (DMSO-$d_6$): δ 7.88 (s, 2H), 7.47 (d, J=1.8 Hz, 2H), 7.09 (t, J=1.8 Hz, 1H), 2.83 (sept, J=6.9 Hz, 2H), 1.19 (d, J=6.9 Hz, 12H). $^{13}$C {$^1$H} NMR (CDCl$_3$): δ 147.01, 129.52, 126.28, 33.55, 24.06.[2]

[2] Signal of the ipso-carbon atom was not detected because of the line broadening 6-tert-Butyl-4-(3,5-diisopropylphenyl)-5-methoxy-2-methylindan-1-one

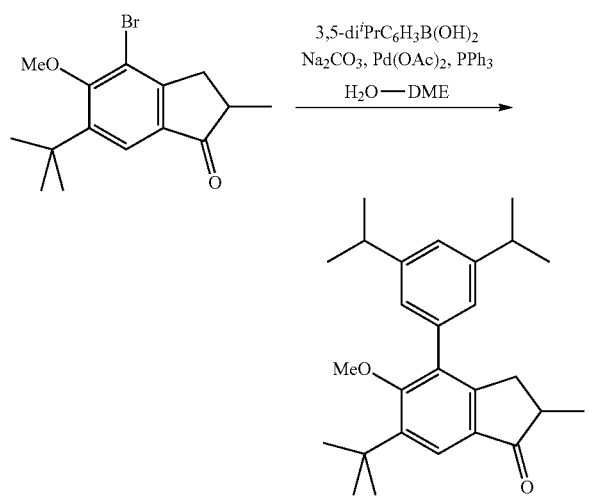

A mixture of 48.45 g (155.7 mmol) of 4-bromo-6-tert-butyl-5-methoxy-2-methylindan-1-one, 40.0 g (193.9 mmol, 1.24 eq.) of (3,5-diisopropylphenyl)boronic acid, 43.9 g (414 mmol) of $Na_2CO_3$, 1.82 g (8.11 mmol, 5 mol. %) of Pd(OAc)$_2$, 4.24 g (16.2 mmol, 10 mol. %) of PPh$_3$, 200 ml of water, and 470 ml of DME was refluxed for 8 h. DME was evaporated on a rotary evaporator, 600 ml of water and 700 ml of dichloromethane were added to the residue. The organic layer was separated, and the aqueous one was additionally extracted with 200 ml of dichloromethane. The combined extract was dried over $K_2CO_3$ and then evaporated to dryness to give a black solid. Crude product was purified by flash chromatography on silica gel 60 (40-63 μm, hexane-dichloromethane=1:1, vol., then, 1:3, vol.) to give 54.9 g (90%) of 6-tert-butyl-4-(3,5-diisopropylphenyl)-5-methoxy-2-methylindan-1-one as a grey solid.

Anal. calc. for $C_{27}H_{36}O_2$: C, 82.61; H, 9.24. Found: C, 82.99; H, 9.45.

$^1$H NMR (CDCl$_3$): δ 7.74 (s, 1H), 7.08 (s, 3H), 3.28 (s, 3H), 3.16 (dd, J=17.4 Hz, J=7.9 Hz, 1H), 2.95 (sept, J=6.9 Hz, 2H), 2.69-2.58 (m, 1H), 2.46 (dd, J=17.4 Hz, J=3.8 Hz, 1H), 1.43 (s, 9H), 1.29 (d, J=6.9 Hz, 12H), 1.25 (d, J=7.5 Hz, 3H). $^{13}$C{$^1$H} NMR (CDCl$_3$): δ 208.91, 163.58, 152.91, 149.19, 143.37, 136.12, 132.93, 130.87, 125.06, 123.76, 121.24, 60.24, 42.22, 35.41, 34.46, 34.15, 30.55, 24.14, 16.41.

5-tert-Butyl-7-(3,5-diisopropylphenyl)-6-methoxy-2-methyl-1H-indene

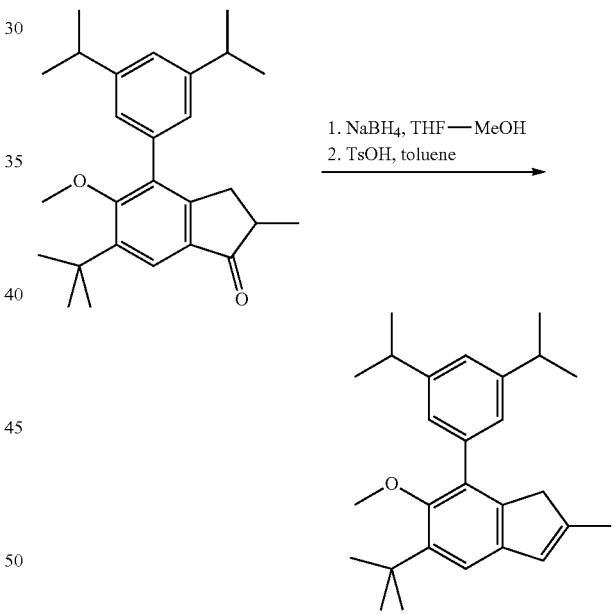

8.0 g (212 mmol) of NaBH$_4$ was added to a solution of 54.9 g (140.0 mmol) of 6-tert-butyl-4-(3,5-diisopropylphenyl)-5-methoxy-2-methylindan-1-one in 300 ml of THF cooled to 5° C. Then, 150 ml of methanol was added dropwise to this mixture by vigorous stirring for ca. 7 h at 5° C. The resulting mixture was evaporated to dryness, and the residue was partitioned between 500 ml of dichloromethane and 500 ml of 2 M HCl. The organic layer was separated, the aqueous layer was additionally extracted with 100 ml of dichloromethane. The combined organic extract was evaporated to dryness to give a white solid. To a solution of this solid in 700 ml of toluene 250 mg of TsOH was added, this mixture was refluxed with Dean-Stark head for 10 min and then cooled to room temperature using a water bath. The formed solution was washed with 10% K$_2$CO$_3$, the organic layer was separated, the aqueous layer was extracted with 150 ml of dichloromethane. The combined organic extract was dried over K$_2$CO$_3$ and then passed through a short layer of silica gel 60 (40-63 μm). The silica gel layer was additionally washed by 100 ml of dichloromethane. The combined organic elute was evaporated to dryness, and the resulting oil was dried in vacuum at elevated temperature. This procedure gave 53.18 g (~100%) of 5-tert-butyl-7-(3,5-diisopropylphenyl)-6-methoxy-2-methyl-1H-indene as a slightly yellowish oil which completely solidified in several hours.

Anal. calc. for C27H36O: C, 86.12; H, 9.64. Found: C, 86.42; H, 9.97.

$^1$H NMR (CDCl$_3$): δ 7.26 (s, 1H), 7.23 (d, J=1.6 Hz, 2H), 7.09 (br.t, J=1.6 Hz, 1H), 6.49 (br.s, 1H), 3.27 (s, 3H), 3.19 (s, 2H), 2.99 (sept, J=6.9 Hz, 2H), 2.12 (s, 3H), 1.50 (s, 9H), 1.34 (d, J=6.9 Hz, 12H). $^{13}$C{$^1$H} NMR (CDCl$_3$): δ 154.32, 148.66, 145.12, 141.74, 140.86, 140.63, 138.10, 132.11, 126.92, 125.04, 123.07, 116.93, 60.33, 42.91, 35.14, 34.14, 31.00, 24.17, 16.67.

Rac-dimethylsilanediyl-bis[2-methyl-4-(3,5-diisopropylphenyl)-5-methoxy-6-tert-butyl-inden-1-yl] zirconium dichloride (MC-CE6)

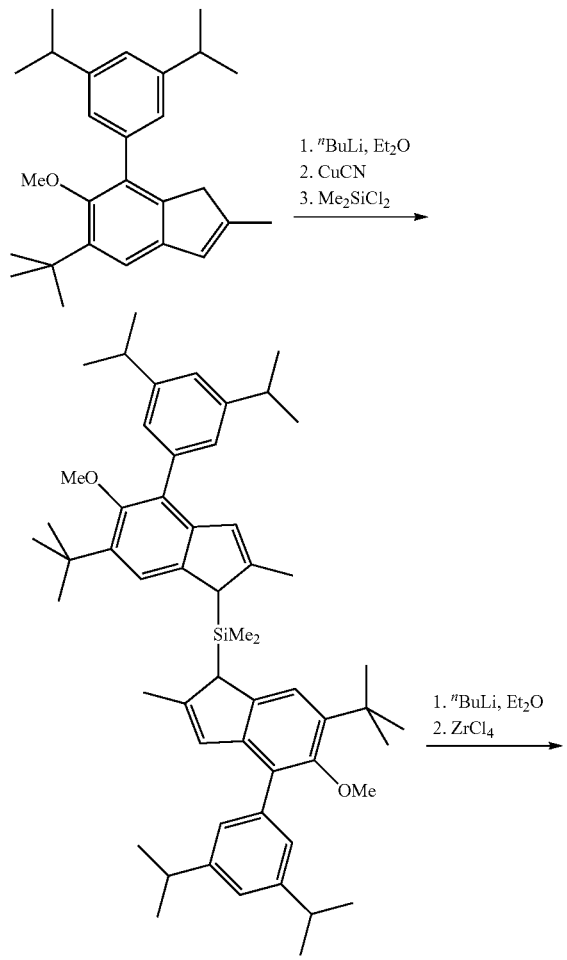

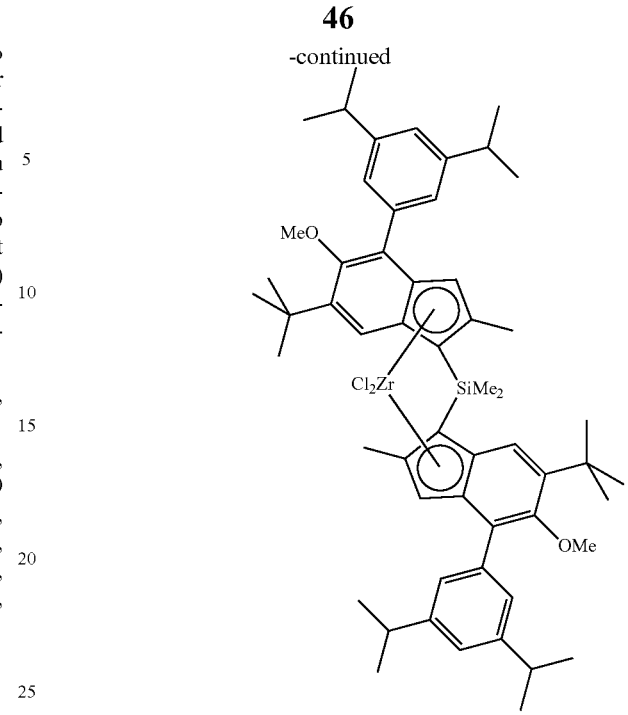

10.5 ml (25.52 mmol) of 2.43 M $^n$BuLi in hexanes was added in one portion to a solution of 9.58 g (25.44 mmol) of 5-tert-butyl-7-(3,5-diisopropylphenyl)-6-methoxy-2-methyl-1H-indene in 200 ml of diethyl ether at −50° C. This mixture was stirred overnight at room temperature, then the resulting light-yellow solution was cooled to −50° C., and 130 mg of CuCN was added. The resulting mixture was stirred for 30 min at −25° C., and then 1.64 g (12.71 mmol) of dichlorodimethylsilane was added in one portion. This mixture was stirred overnight at ambient temperature, then it was filtered through a glass frit (G4), and the obtained slightly yellowish solution was further used without additional purification. To thus obtained solution containing 12.72 mmol (assuming almost quantitative yield on the previous step) of bis[6-tert-butyl-4-(3,5-diisopropylphenyl)-5-methoxy-2-methyl-1H-inden-1-yl]dimethylsilane cooled to −50° C., 10.5 ml (25.52.0 mmol) of 2.43 M $^n$BuLi in hexanes was added in one portion. This mixture was stirred overnight at room temperature. The resulting light orange-yellow solution was cooled to −50° C., and 2.97 g (12.75 mmol) of ZrCl$_4$ was added. The reaction mixture was stirred for 24 h at room temperature resulting in a red suspension with an orange precipitate. This mixture was evaporated to dryness, and the residue was treated with 100 ml of hot toluene. This mixture was filtered while hot through glass frit (G4), and the filtrate was evaporated to ca. 40 ml. Orange powder precipitated from this solution over 2 h at room temperature was collected and dried in vacuum. This procedure gave 4.17 g of rac-complex. The mother liquor was evaporated to ca. 20 ml, and the precipitated light-orange solid was filtered off (G3) to give another 1.3 g portion of rac-isomer. The mother liquor was evaporated to dryness, and the residue was treated with 25 ml of hot hexane. Crystalline solid precipitated overnight at −30° C. was collected and dried in vacuum. This procedure gave 2.9 g of meso-complex. Thus, the total yield of rac- and meso-complexes isolated in this synthesis was 8.37 g (68%).

Rac-MC-CE6.

Anal. calc. for C$_{56}$H$_{74}$Cl$_2$O$_2$SiZr: C, 67.26; H, 6.82. Found: C, 67.45; H, 7.01.

$^{1}$H NMR (CDCl$_3$): δ 7.50 (s, 2H), 7.61-7.34 (very br.s, 2H), 7.34-7.06 (very br.s, 2H), 7.01 (s, 2H), 6.56 (s, 2H), 3.35 (s, 6H), 2.90 (sept, J=6.8 Hz, 4H), 2.14 (s, 6H), 1.39 (s, 18H), 1.27 (s, 6H), 1.26 (d, J=6.8 Hz, 12H), 1.24 (br.d, J=6.8 Hz, 12H). $^{13}$C{$^{1}$H} NMR (CDCl$_3$): δ 159.73, 148.81 (br.s), 144.03, 136.64, 134.60, 133.75, 127.37, 125.31, 123.70, 123.11, 121.40, 120.62, 81.64, 62.39, 35.77, 34.20, 30.43, 24.35, 23.84 (br.s), 18.38, 2.46.

Meso-MC-CE6.

Anal. calc. for C$_{56}$H$_{74}$Cl$_2$O$_2$SiZr: C, 67.26; H, 6.82. Found: C, 67.38; H, 7.07.

$^{1}$H NMR (CDCl$_3$): δ 7.78-7.44 (very br.s, 2H), 7.41 (s, 2H), 7.35-7.05 (very br.s, 2H), 7.02 (s, 2H), 6.55 (s, 2H), 3.20 (s, 6H), 2.91 (sept, J=6.9 Hz, 4H), 2.38 (s, 6H), 1.40 (s, 3H), 1.37 (s, 18H), 1.29 (br.m, 12H), 1.26 (d, J=6.9 Hz, 12H), 1.19 (s, 3H). $^{13}$C{$^{1}$H} NMR (CDCl$_3$): δ 158.63, 148.82 (br.s), 143.91, 136.43, 135.41, 134.82, 127.06, 125.24, 125.17, 123.91, 123.27, 120.00, 83.54, 61.95, 35.68, 34.26, 30.55, 24.27, 23.95 (br.s), 18.45, 3.02, 2.34.

Synthesis of Comparative Metallocene MC-CE7

Chloro[4-(3,5-di-tert-butylphenyl)-2,6-dimethyl-1H-inden-1-yl]dimethylsilane

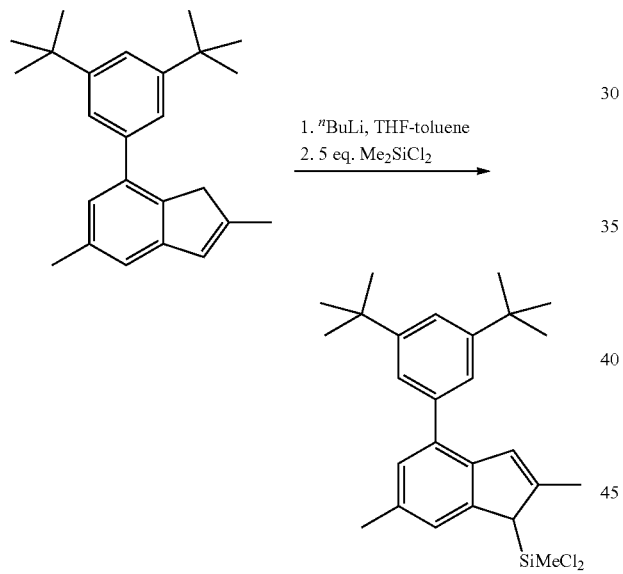

10 ml (25.0 mmol) of 2.5 M $^n$BuLi in hexanes was added at room temperature to a solution of 8.31 g (25.0 mmol) of 7-(3,5-di-tert-butylphenyl)-2,5-dimethyl-1H-indene in a mixture of 200 ml of toluene and 7.5 ml of THF. The resulting yellowish solution was stirred for 2 h at 60° C., then cooled to −50° C., and 16.1 g (125 mmol, 5 eq.) of dichlorodimethylsilane was added in one portion. The formed solution was warmed to room temperature and then refluxed for 2 h. The resulting mixture was filtered through a glass frit (G3). The precipitate was additionally washed with 2×10 ml of toluene. The combined filtrate was evaporated to dryness to give the title material as a slightly yellowish glassy mass which was further used without additional purification.

$^{1}$H NMR (CDCl$_3$): δ 7.41 (m, 1H), 7.34 (m, 2H), 7.25 (m, 1H), 7.12 (m, 1H), 6.76 (m, 1H), 3.60 (s, 1H), 2.44 (s, 3H), 2.25 (s, 3H), 1.38 (s, 18H), 0.44 (s, 3H), 0.19 (s, 3H). $^{13}$C{$^{1}$H} NMR (CDCl$_3$): δ 150.57, 144.87, 143.48, 140.51, 140.26, 134.93, 132.83, 127.16, 126.59, 123.22, 123.15, 120.70, 50.05, 34.93, 31.56, 21.60, 17.72, 1.14, −0.57.

[6-tert-Butyl-4-(3,5-di-tert-butylphenyl)-5-methoxy-2-methyl-1H-inden-1-yl][4-(3,5-di-tert-butylphenyl)-2,6-dimethyl-1H-inden-1-yl]dimethylsilane

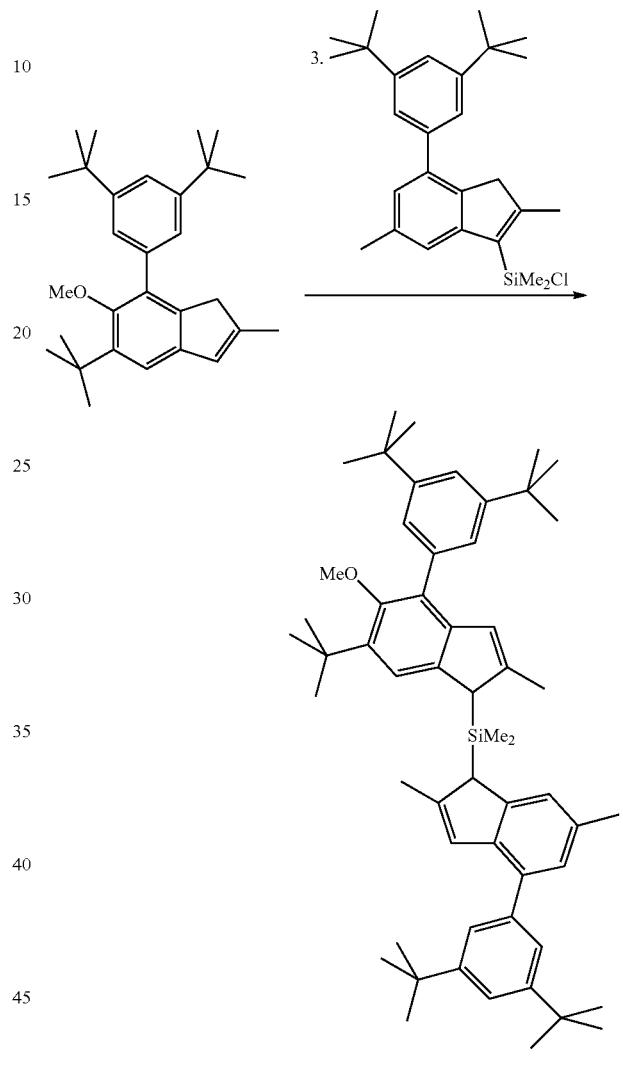

10.0 ml (25.0 mmol) of 2.5 M $^n$BuLi in hexanes was added in one portion to a solution of 10.1 g (25.0 mmol) of 5-tert-butyl-7-(3,5-di-tert-butylphenyl)-6-methoxy-2-methyl-1H-indene in 150 ml of ether at −50° C. This mixture was stirred at room temperature for 4 h, then the formed yellowish suspension was cooled to −50° C., and 200 mg of CuCN was added. The obtained mixture was stirred for 30 min at −25° C., then a solution of chloro[4-(3,5-di-tert-butylphenyl)-2,6-dimethyl-1H-inden-1-yl]dimethylsilane (as prepared above, ~25.0 mmol) in 150 ml of ether was added in one portion. The resulting mixture was stirred overnight at ambient temperature and then filtered through a pad of silica gel 60 (40-63 μm) which was additionally washed with 2×70 ml of dichloromethane. The combined filtrate was evaporated to dryness under vacuum, and the residue was dried in vacuo at elevated temperature. This procedure gave 20.2 g (~100%) of a yellowish glass of the title product of >95% purity. On the evidence of NMR spectroscopy this product is a ca. 1:1 mixture of the stereoisomers. This material was further used without additional purification.

¹H NMR (CDCl₃): δ 7.55 (m), 7.33-7.49 (m), 7.26 (m), 7.22 (m), 7.15 (m), 6.80 (m), 6.57 (m), 6.55 (m), 3.75 (s), 3.24 (s), 3.22 (s), 2.46 (s), 2.25 (s), 2.24 (s), 2.22 (s), 1.48 (s), 1.46 (s), 1.42 (s), 1.41 (s), −0.13 (s), −0.15 (s), −0.21 (s).

Dimethylsilanediyl[2-methyl-4-(3,5-di-tert-butylphenyl)-5-methoxy-6-tert-butyl-inden-1-yl][2,6-dimethyl-4-(3,5-di-tert-butylphenyl)-inden-1-yl]zirconium dichloride (MC-CE7)

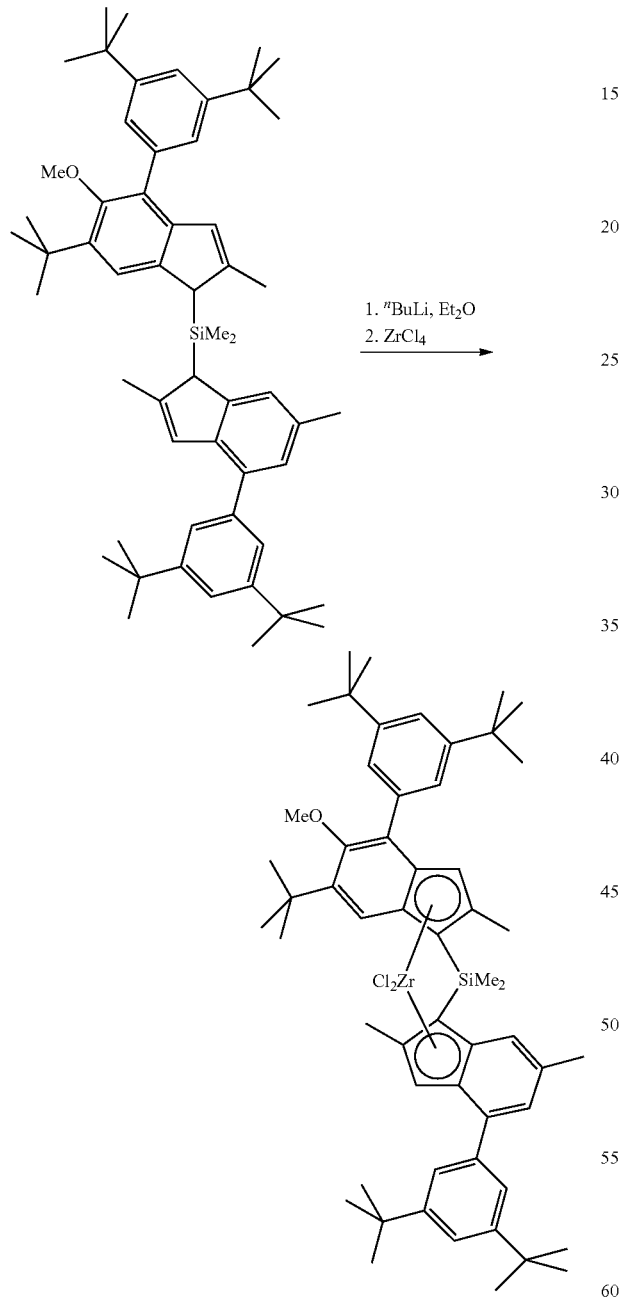

20.0 ml (50.0 mmol) of 2.5 M ⁿBuLi in hexanes was added in one portion to a solution of 20.2 g (ca. 25 mmol) of [6-tert-butyl-4-(3,5-di-tert-butylphenyl)-5-methoxy-2-methyl-1H-inden-1-yl][4-(3,5-di-tert-butylphenyl)-2,6-dimethyl-1H-inden-1-yl]dimethylsilane in 300 ml of ether cooled to −50° C. This mixture was stirred at room temperature for 5 h. The resulting light red solution was cooled to −50° C., and 5.83 g (25.02 mmol) of ZrCl₄ was added. The reaction mixture was stirred for 24 h and then evaporated to dryness. 200 ml of hot toluene was added to the residue, and the formed hot suspension was filtered through a glass frit (G4). On the evidence of NMR spectroscopy the obtained filtrate included a ca. 55 to 45 mixture of anti- and syn-zirconocenes. This filtrate was evaporated to ca. 50 ml. The orange crystalline material precipitated from this mixture overnight at room temperature was collected and dried in vacuum. This procedure gave 7.10 g of anti-zirconocene. The mother liquor was evaporated to dryness, and the residue was dissolved in 50 ml of warm n-hexane. The orange material precipitated from this solution overnight at room temperature was collected and then dried in vacuum. This procedure gave 9.50 g of a ca. 35 to 65 mixture of anti- and syn-zirconocenes. Again, the mother liquor was evaporated to dryness, and the residue was dissolved in 20 ml of warm n-hexane. Crystals precipitated from this solution overnight at room temperature and were collected and dried in vacuum. This procedure gave 0.40 g of anti-zirconocene. Thus, the total yield of syn- and anti-zirconocenes isolated in this synthesis was 17.0 g (71%).

Anti-zirconocene.

Anal. calc. for $C_{56}H_{74}Cl_2OSiZr$: C, 70.55; H, 7.82 Found: C, 70.70; H, 8.05.

¹H NMR (CDCl₃): δ 7.60 (very br.s, 1H), 7.47-7.56 (m, 3H), 7.37-7.43 (m, 2H), 7.33 (m, 1H), 7.29-7.44 (very br.s, 1H), 7.21 (m, 1H), 6.89 (s, 1H), 6.58 (s, 1H), 3.32 (s, 3H), 2.35 (s, 3H), 2.20 (s, 3H), 2.18 (s, 3H), 1.40 (s, 9H), 1.20-1.37 (m, 42H). ¹³C{¹H} NMR (CDCl₃): δ 159.91, 150.87, 144.24, 139.29, 138.71, 135.85, 135.54, 135.20, 134.05, 133.79, 130.68, 128.87, 128.17, 127.72, 124.7 (br.), 124.1 (br.), 123.56, 123.29, 122.49, 122.00, 121.84, 121.44, 120.58, 120.30, 81.94, 81.85, 62.29, 35.80, 35.05, 35.0 (br.), 31.56, 31.49, 30.44, 22.16, 18.38 (two resonances), 2.75, 2.58.

MC-CE8

Rac-methyl(cyclohexyl)silanediylbis[2-methyl-4-(4-tert-butylphenyl)indenyl]zirconium dichloride (MC-8)

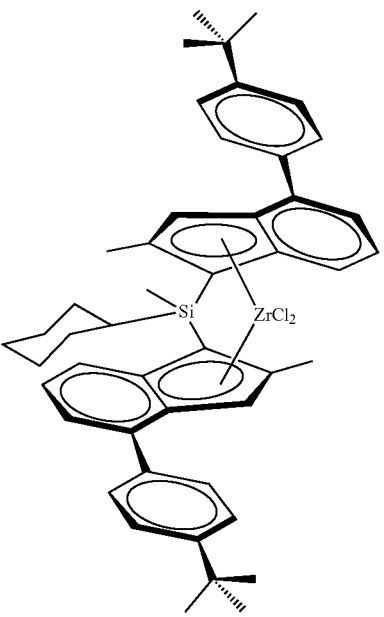

is described in WO2005105863 A2 (example 18) and was purchased from a commercial source. CAS no 888227-55-2.

MC-CE9

Rac-anti-dimethylsilanediyl (2-methyl-4-(4'-tert-butylphenyl)inden-1-yl)(2-methyl-4-phenyl-5-methoxy-6-tert-butyl inden-1-yl) zirconium dichloride

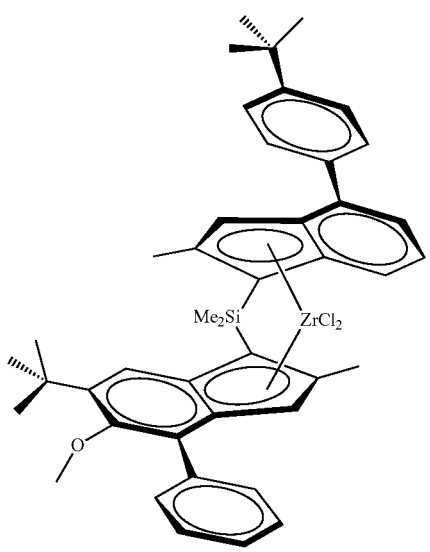

was prepared as described in WO2013/007650, metallocene E2

MC-CE10 rac-anti-dimethylsilanediyl (2-methyl-4-(4-tert-butylphenyl)inden-1-yl)(2-methyl-4-(4'-tert-butylphenyl)-5-methoxy-6-tert-butyl inden-1-yl) zirconium dichloride

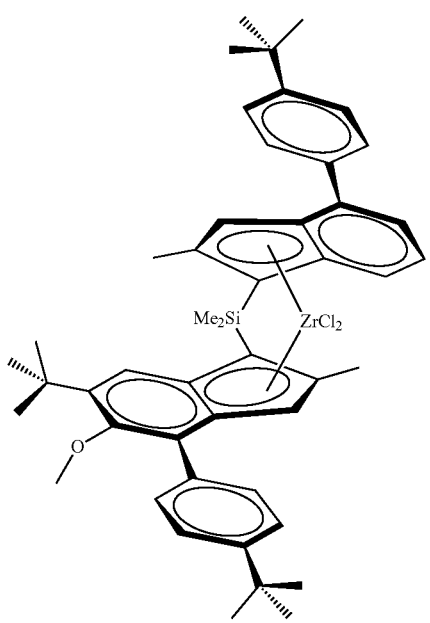

was prepared as described in WO2013/007650, metallocene E7

Synthesis of Inventive Metallocene MC-IE1

(3,5-Dimethylphenyl)boronic acid

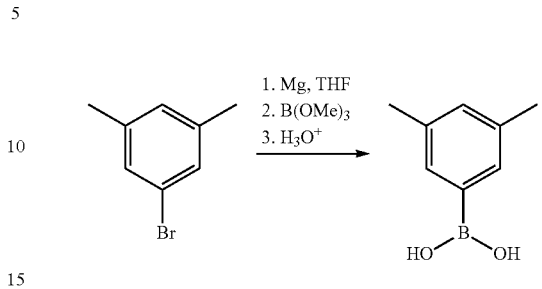

A solution of 3,5-dimethylphenylmagnesium bromide obtained from a solution of 190.3 g (1.03 mol) of 1-bromo-3,5-dimethylbenzene in 1000 ml of THF and 32 g (1.32 mol, 28% excess) of magnesium turnings was cooled to −78° C., and 104 g (1.0 mol) of trimethylborate was added in one portion. The resulting heterogeneous mixture was stirred overnight at room temperature. The boronic ester was hydrolyzed by careful addition of 1200 ml of 2 M HCl. 500 ml of diethyl ether was added, the organic layer was separated, and the aqueous layer was additionally extracted with 2×500 ml of diethyl ether. The combined organic extract was dried over Na2SO4 and then evaporated to dryness to give white mass. The latter was triturated with 200 ml of hexane, filtered through glass frit (G3), and the precipitate was dried in vacuo. This procedure gave 114.6 g (74%) of (3,5-dimethylphenyl)boronic acid.

Anal. calc. for C8H11BO2: C, 64.06; H, 7.39. Found: C, 64.38; H, 7.72.

1H NMR (DMSO-d6): δ 7.38 (s, 2H), 7.00 (s, 1H), 3.44 (very br.s, 2H), 2.24 (s, 6H).

2-methyl-4-(3,5-dimethylphenyl)-5-methoxy-6-tert-butyl-indan-1-one

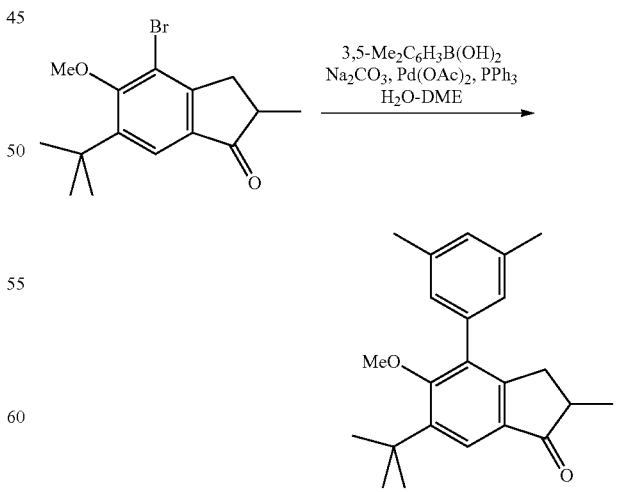

A mixture of 49.14 g (157.9 mmol) of 2-methyl-4-bromo-5-methoxy-6-tert-butyl-indan-1-one, 29.6 g (197.4 mmol, 1.25 eq.) of (3,5-dimethylphenyl)boronic acid, 45.2 g (427 mmol) of Na$_2$CO$_3$, 1.87 g (8.3 mmol, 5 mol. %) of Pd(OAc)$_2$, 4.36 g (16.6 mmol, 10 mol. %) of PPh$_3$, 200 ml of water, and 500 ml of 1,2-dimethoxyethane was refluxed for 6.5 h. DME was evaporated on a rotary evaporator, 600 ml of water and 700 ml of dichloromethane were added to the residue. The organic layer was separated, and the aqueous one was additionally extracted with 200 ml of dichloromethane. The combined extract was dried over K$_2$CO$_3$ and then evaporated to dryness to give black oil. Crude product was purified by flash chromatography on silica gel 60 (40-63 μm, hexane-dichloromethane=1:1, vol., then, 1:3, vol.) to give 48.43 g (91%) of 2-methyl-4-(3,5-dimethylphenyl)-5-methoxy-6-tert-butyl-indan-1-one as a brownish oil.

Anal. calc. for C$_{23}$H$_{28}$O$_2$: C, 82.10; H, 8.39. Found: C, 82.39; H, 8.52.

$^1$H NMR (CDCl$_3$): δ 7.73 (s, 1H), 7.02 (s, 3H), 7.01 (s, 3H), 3.32 (s, 3H), 3.13 (dd, =17.5 Hz, J=7.8 Hz, 1H), 2.68-2.57 (m, 1H), 2.44 (dd, J=17.5 Hz, J=3.9 Hz), 2.36 (s, 6H), 1.42 (s, 9H), 1.25 (d, J=7.5 Hz, 3H). $^{13}$C {$^1$H} NMR (CDCl$_3$): 208.90, 163.50, 152.90, 143.32, 138.08, 136.26, 132.68, 130.84, 129.08, 127.18, 121.30, 60.52, 42.17, 35.37, 34.34, 30.52, 21.38, 16.40.

2-methyl-5-tert-butyl-6-methoxy-7-(3,5-dimethylphenyl)-1H-indene

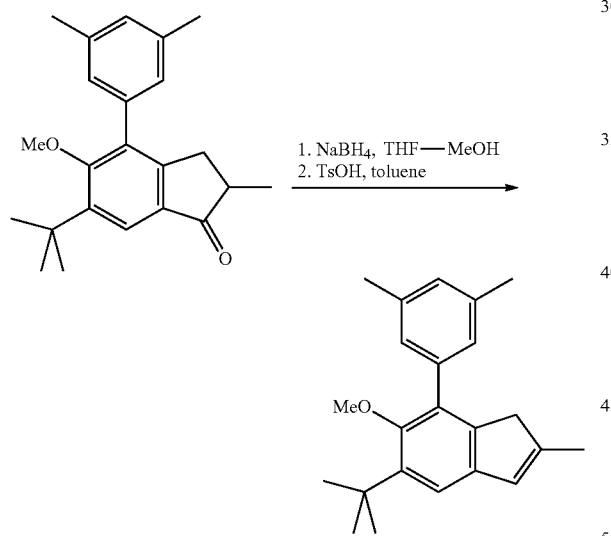

NaBH$_4$ (8.2 g, 217 mmol) was added to a solution of 48.43 g (143.9 mmol) of 2-methyl-4-(3,5-dimethylphenyl)-5-methoxy-6-tert-butyl-indan-1-one in 300 ml of THF cooled to 5° C. Further on, 150 ml of methanol was added dropwise to this mixture by vigorous stirring for ca. 7 h at 5° C. The resulting mixture was evaporated to dryness, and the residue wad partitioned between 500 ml of dichloromethane and 500 ml of 2 M HCl. The organic layer was separated; the aqueous layer was additionally extracted with 100 ml of dichloromethane. The combined organic extract was evaporated to dryness to give slightly yellowish oil. To a solution of this oil in 600 ml of toluene 400 mg of TsOH was added, this mixture was refluxed with Dean-Stark head for 10 min and then cooled to room temperature using water bath. The formed solution was washed by 10% Na$_2$CO$_3$, the organic layer was separated, the aqueous layer was extracted with 150 ml of dichloromethane. The combined organic extract was dried over K$_2$CO$_3$ and then passed through a short layer of silica gel 60 (40-63 μm). The silica gel layer was additionally washed by 100 ml of dichloromethane. The combined organic elute was evaporated to dryness, and the resulting oil was dried in vacuum at elevated temperature. This procedure gave 45.34 g (98%) of 2-methyl-5-tert-butyl-6-methoxy-7-(3,5-dimethylphenyl)-1H-indene which was further used without an additional purification.

Anal. calc. for C23H280: C, 86.20; H, 8.81. Found: C, 86.29; H, 9.07.

$^1$H NMR (CDCl$_3$): δ 7.20 (s, 1H), 7.08 (br.s, 1H), 6.98 (br.s, 1H), 6.42 (m, 1H), 3.25 (s, 3H), 3.11 (s, 2H), 2.36 (s, 6H), 2.06 (s, 3H), 1.43 (s, 9H). $^{13}$C {$^1$H} NMR (CDCl$_3$): δ 154.20, 145.22, 141.78, 140.82, 140.64, 138.30, 137.64, 131.80, 128.44, 127.18, 126.85, 116.98, 60.65, 42.80, 35.12, 31.01, 21.41, 16.65.

One-pot synthesis of 2-methyl-5-tert-butyl-6-methoxy-7-(3,5-dimethylphenyl)-1H-indene from 2-methyl-4-bromo-5-methoxy-6-tert-butyl-indan-1-one

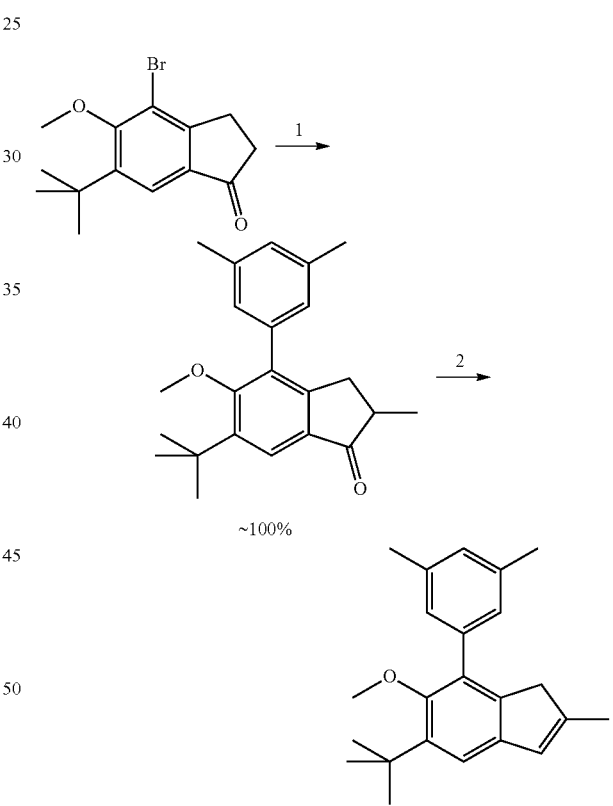

Step 1: 2 Mol. % Pd(PtBu$_3$)$_2$, 2-MeTHF, 7 h at Reflux

A mixture of 2-methyl-4-bromo-5-methoxy-6-tert-butyl-indan-1-one (15.75 g, 50.61 mmol), (3,5-dimethylphenyl) boronic acid (9.5 g, 63.34 mmol, 1.25 equiv.), Na$_2$CO$_3$ (14.5 g, 137 mmol), Pd(PtBu$_3$)2 (0.51 g, 1 mmol), 66 ml of water and 165 ml of 2-methyltetrahydrofuran was refluxed for 7 h. After cooling to room temperature, the organic layer was separated, dried over K2CO3, and the resulting solution was used in the following step without additional purification.

1H NMR (CDCl$_3$): δ 7.73 (s, 1H), 7.02 (s, 3H), 7.01 (s, 3H), 3.32 (s, 3H), 3.13 (dd, J=17.5 Hz, J=7.8 Hz, 1H), 2.68-2.57 (m, 1H), 2.44 (dd, J=17.5 Hz, J=3.9 Hz), 2.36 (s, 6H), 1.42 (s, 9H), 1.25 (d, J=7.5 Hz, 3H). 13C{1H} NMR (CDCl3): δ 208.90, 163.50, 152.90, 143.32, 138.08, 136.26, 132.68, 130.84, 129.08, 127.18, 121.30, 60.52, 42.17, 35.37, 34.34, 30.52, 21.38, 16.40

Step 2: A) NaBH$_4$/2-MeTHF/MeOH; b) TsOH/Toluene at Reflux

NaBH4 (5.2 g, 138 mmol) was added to the above solution of 2-methyl-4-(3,5-dimethylphenyl)-5-methoxy-6-tert-butyl-indan-1-one in 165 ml of 2-methyltetrahydrofuran cooled to 5° C. Further on, 80 ml of methanol was added dropwise to this mixture for ca. 7 h at 5° C. The resulting mixture was evaporated to dryness, 300 ml of dichloromethane and 300 ml water were added to the residue, and thus obtained mixture was acidified with 2 M HCl to pH-6.5. The organic layer was separated; the aqueous layer was additionally extracted with 100 ml of dichloromethane. The combined organic extract was passed through a pad (~200 ml) of silica gel 60 (40-63 µm; eluent: dichloromethane). The obtained elute was evaporated to dryness to give a slightly brownish oil. 200 mg of TsOH was added to a solution of this oil in 200 ml of toluene. This mixture was refluxed with Dean-Stark head for 10 min and then cooled to room temperature using a water bath. The formed solution was washed with 10% Na2CO3, the organic layer was separated, and the aqueous layer was extracted with 50 ml of dichloromethane. The combined organic extract was dried over K2CO3 and then evaporated to dryness. The residue was dissolved in 100 ml of n-hexane, and the obtained solution was passed through a short pad (~20 ml) of silica gel 60 (40-63 µm; eluent: n-hexane). The silica gel layer was additionally washed by 40 ml of n-hexane. The combined organic elute was evaporated to dryness, and the resulting oil was dried in vacuum at elevated temperature to give 15.35 g (95%) of 2-methyl-5-tert-butyl-6-methoxy-7-(3,5-dimethylphenyl)-1H-indene which was used in the following step without additional purification.

1H NMR (CDCl3): δ 7.20 (s, 1H), 7.08 (br.s, 1H), 6.98 (br.s, 1H), 6.42 (m, 1H), 3.25 (s, 3H), 3.11 (s, 2H), 2.36 (s, 6H), 2.06 (s, 3H), 1.43 (s, 9H). 13C{1H} NMR (CDCl3): δ 154.20, 145.22, 141.78, 140.82, 140.64, 138.30, 137.64, 131.80, 128.44, 127.18, 126.85, 116.98, 60.65, 42.80, 35.12, 31.01, 21.41, 16.65.

Bis[2-methyl-4-(3,5-dimethylphenyl)-5-methoxy-6-tert-butyl-1H-inden-1-yl]dimethylsilane

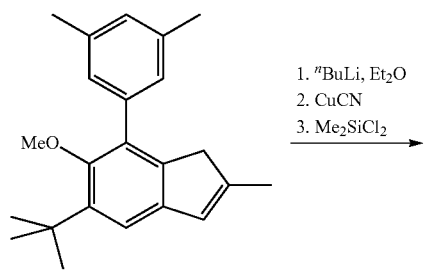

1. $^n$BuLi, Et$_2$O
2. CuCN
3. Me$_2$SiCl$_2$

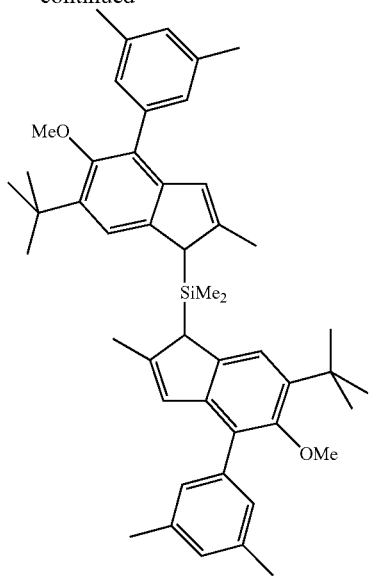

nBuLi in hexanes (2.5 M, 28.0 ml, 70 mmol) was added in one portion to a solution of 22.36 g (69.77 mmol) of 2-methyl-5-tert-butyl-6-methoxy-7-(3,5-dimethylphenyl)-1H-indene in 350 ml of ether at −50° C. This mixture was stirred overnight at room temperature, then the resulting orange solution with a large amount of yellow precipitate was cooled to −60° C. (at this temperature the precipitate almost completely disappeared), and 400 mg of CuCN was added. The resulting mixture was stirred for 30 min at −25° C., and then 4.51 g (34.95 mmol) of dichlorodimethylsilane was added in one portion. This mixture was stirred overnight at room temperature, then filtered through a pad of silica gel 60 (40-63 µm) which was additionally washed by 2×50 ml of dichloromethane. The combined filtrate was evaporated under reduced pressure, and the residue was dried in vacuum at elevated temperature. This procedure gave 24.1 g (99%) of bis[2-methyl-4-(3,5-dimethylphenyl)-5-methoxy-6-tert-butyl-1H-inden-1-yl]dimethylsilane (>90% purity by NMR, approx. 3:1 mixture of stereoisomers) as yellowish glass which was further used without additional purification.

1H NMR (CDCl3): δ 7.49, 7.32, 7.23, 7.11, 6.99 (5s, sum 8H), 6.44 and 6.43 (2s, sum 2H), 3.67, 3.55 (2s, sum 2H), 3.27, 3.26 (2s, sum 6H), 2.38 (s, 12H), 2.13 (s, 6H), 1.43 (s, 18H), −0.13, −0.18, −0.24 (3s, sum 6H). 13C{1H} NMR (CDCl3): δ 155.29, 147.57, 147.23, 143.63, 139.37, 139.26, 138.19, 137.51, 137.03, 128.24, 127.90, 127.47, 126.01, 125.89, 120.53, 120.34, 60.51, 47.35, 47.16, 35.14, 31.28, 31.20, 21.44, 17.94, 17.79, −4.84, −4.89, −5.84.

Rac-dimethylsilanediyl-bis[2-methyl-4-(3,5-dimethylphenyl)-5-methoxy-6-tert-butyl-inden-1-yl]zirconium dichloride (MC-IE1)

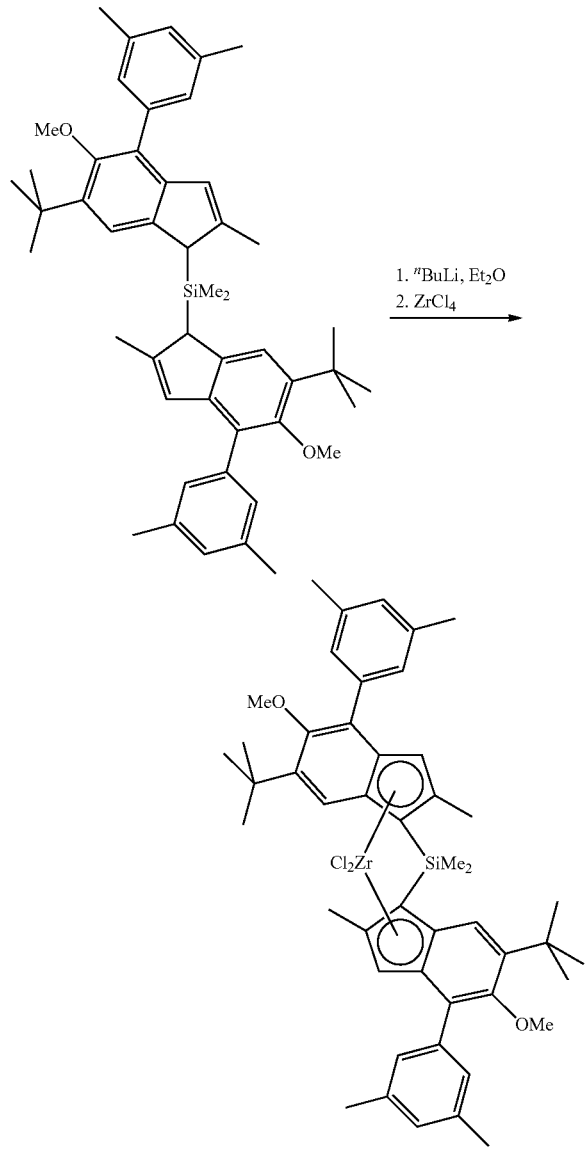

"BuLi in hexanes (2.5 M, 27.7 ml, 69.3 mmol) was added in one portion to a solution of 24.1 g (34.53 mmol) of bis[2-methyl-4-(3,5-dimethylphenyl)-5-methoxy-6-tert-butyl-1H-inden-1-yl]dimethylsilane (prepared above) in 350 ml of diethyl ether cooled to −50° C. This mixture was stirred overnight at room temperature, then the resulting yellow solution with a large amount of yellow precipitate was cooled to −50° C., and 8.05 g (34.54 mmol) of ZrCl$_4$ was added. The reaction mixture was stirred for 24 h at room temperature to give reddish-orange solution containing some precipitate. This mixture was evaporated to dryness. The residue was heated with 200 ml of toluene, and the formed suspension was filtered while hot through glass frit (G4). The filtrate was evaporated to 70 ml, and then 50 ml of hexane was added. Crystals precipitated from this solution overnight at room temperature were collected, washed with 25 ml of hexane, and dried in vacuum. This procedure gave 4.01 g of pure rac-zirconocene. The mother liquor was evaporated to ca. 50 ml, and 50 ml of hexane was added. Orange crystals precipitated from this solution overnight at room temperature were collected and then dried in vacuum. This procedure gave 2.98 g of rac-zirconocene. Again, the mother liquor was evaporated almost to dryness, and 50 ml of hexane was added. Orange crystals precipitated from this solution overnight at −30° C. were collected and dried under vacuum. This procedure gave 3.14 g of rac-zirconocene. Thus, the total yield of rac-zirconocene isolated in this synthesis was 10.13 g (34%).

Anal. calc. for $C_{48}H_{58}Cl_2O_2SiZr$: C, 67.26; H, 6.82. Found: C, 67.42; H, 6.99.

$^1$H NMR (Rac-B6, CDCl$_3$): δ 7.49 (s, 1H), 7.23 (very br.s, 2H), 6.96 (s, 1H), 6.57 (s, 1H), 3.44 (s, 3H), 2.35 (s, 6H), 2.15 (s, 3H), 1.38 (s, 9H), 1.27 (s, 3H). $^{13}$C {$^1$H} NMR (CDCl$_3$): δ 159.78, 144.04, 137.87, 136.85, 134.89, 133.86, 128.85, 127.39, 127.05, 122.91, 121.18, 120.80, 81.85, 62.66, 35.76, 30.38, 21.48, 18.35, 2.41.

Synthesis of Inventive Metallocene MC-IE2

2-Chloro-4-methylbenzaldehyde

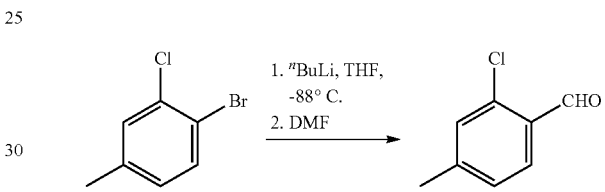

165 ml (413 mmol) of 2.5 M "BuLi in hexanes was added dropwise over 1 h to a solution of 82.2 g (400 mmol) of 3-chloro-4-bromo-toluene in 400 ml of THF cooled to −88° C. The resulting mixture was stirred for 30 min at this temperature, and then 44.0 g (602 mmol) of DMF was added dropwise over 10 min by vigorous stirring. The reaction mixture was stirred overnight at room temperature, then cooled to 0° C. in an ice bath and then 100 ml of water and 400 ml of 3N HCl were added. The organic layer was separated and the aqueous layer was extracted with 2×125 ml of dichloromethane. The combined organic extract was dried over K$_2$CO$_3$ and then passed through a short layer of silica gel 60 (40-63 μm). The silica gel layer was additionally washed with 50 ml of dichloromethane. The combined organic elute was evaporated to dryness to give a slightly orange liquid which was then distilled in vacuum to give 58.0 g (94%) of the title product (b.p. 99-102° C./11 mm Hg) as a colorless liquid that crystallized overnight at room temperature.

Anal. calc. for C$_8$H$_7$ClO: C, 62.15; H, 4.56. Found: C, 62.24; H, 4.45.

$^1$H NMR (CDCl$_3$): δ 10.4 (s, 1H, CHO), 7.80 (d, J=7.8 Hz, 1H, 6-H), 7.25 (s, 1H, 3-H), 7.17 (d, J=7.8 Hz, 1H, 5-H), 2.40 (s, 3H, 4-Me).

(2-Chloro-4-methylphenyl)methanol

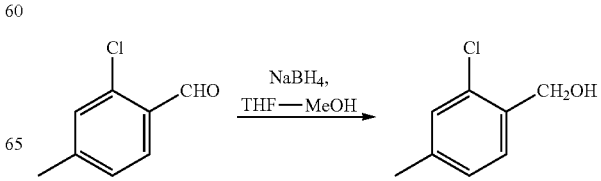

375 ml of methanol was added dropwise by vigorous stirring over 5 h to a mixture of 116 g (0.75 mol) of 2-chloro-4-methylbenzaldehyde and 43.0 g (1.14 mol) of NaBH4 in 750 ml of THF at 0-5° C. This mixture was stirred overnight at room temperature, and then evaporated to dryness. The resulting oily mass was acidified with 1200 ml of 2 M HCl to pH-1, and the formed product was extracted consequently with 3×400 ml of dichloromethane. The combined organic extract was dried over $Na_2SO_4$ and evaporated to dryness. This product was used without additional purification.

$^1$H NMR (CDCl$_3$): δ 7.29 (d, J=7.8 Hz, 1H, 5-H), 7.15 (s, 1H, 3-H), 7.04 (d, J=7.8 Hz, 1H, 6-H), 4.67 (s, 2H, CH$_2$OH), 2.59 (br.s, 1H, CH$_2$OH), 2.30 (s, 3H, 4-Me). $^{13}$C{$^1$H} NMR (CDCl$_3$): δ 138.9, 135.0, 132.4, 129.7, 128.6, 127.6, 62.5, 20.7.

2-Chloro-1-(chloromethyl)-4-methylbenzene

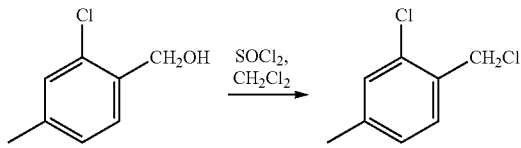

The above-obtained 2-chloro-4-methylbenzyl alcohol dissolved in 750 ml of dichloromethane was added dropwise to 55 ml (754 mmol) of thionyl chloride at +5° C. The resulting solution was stirred overnight at room temperature and then evaporated to dryness. The residue was dissolved in 500 ml dichloromethane, and the formed solution was washed by 250 ml of water. The organic layer was separated; the aqueous layer was extracted with 2×150 ml of dichloromethane. The combined organic extract was dried over Na$_2$SO$_4$, passed through a short pad of silica gel 60 (40-63 μm) and then evaporated to dryness. The crude product was distilled in vacuum to give 114 g (87%) of the title product as a colorless liquid, b.p. 92-95° C./5 mm Hg.

Anal. calc. for C$_8$H$_8$Cl$_2$: C, 54.89; H, 4.61. Found: C, 54.80; H, 4.65.

$^1$H NMR (CDCl$_3$): δ 7.30 (d, J=7.8 Hz, 1H, 5-H), 7.19 (s, 1H, 3-H), 7.04 (d, J=7.8 Hz, 1H, 6-H), 4.64 (s, 2H, CH$_2$Cl), 2.30 (s, 3H, Me). $^{13}$C{$^1$H} NMR (CDCl$_3$): δ 140.3, 133.7, 131.9, 130.6, 130.2, 127.9, 43.5, 20.8.

3-(2-Chloro-4-methylphenyl)-2-methylpropanoyl chloride

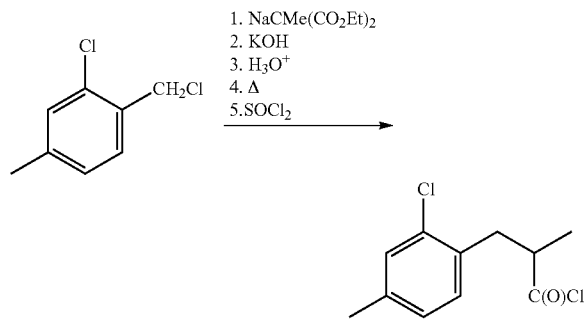

119 g (0.68 mol) of diethyl methylmalonate was added to a solution of sodium ethoxide obtained from 17.0 g (0.74 mol) of sodium metal and 600 ml of dry ethanol. The formed mixture was stirred for 15 min, and then 114 g (0.651 mol) of 2-chloro-1-(chloromethyl)-4-methylbenzene was added by vigorous stirring at such a rate to maintain a gentle reflux. The resulting mixture was refluxed for 2 h and then cooled to room temperature. A solution of 135 g of KOH in 550 ml of water was added. This mixture was refluxed for 4 h to saponificate the ester formed. Ethanol and water were distilled off until vapor temperature reached 95° C., then 3000 ml of water and then 12 M HCl (to pH~1) were added to the residue. The precipitated substituted methylmalonic acid was filtered off and washed with water. This diacid was decarboxylated at 160-180° C. to form a slightly orange oil that crystallized at room temperature. A mixture of the formed acid and 166 ml of thionyl chloride was stirred for 24 h at room temperature. After evaporation of the excess of thionyl chloride, the residue was distilled in vacuum to give 123 g (82%) of the title product, b.p. 105-117° C./5 mm Hg.

Anal. calc. for C$_{11}$H$_{12}$Cl$_2$O: C, 57.16; H, 5.23. Found: C, 57.36; H, 5.38.

$^1$H NMR (CDCl$_3$): δ 7.19 (s, 1H, 3-H), 7.10 (d, J=7.7 Hz, 1H, 5-H), 7.00 (d, J=7.7 Hz, 1H, 6-H), 3.20-3.32 (m, 2H, CHH' and CHMe), 2.82 (dd, J=12.8 Hz, J=6.4 Hz, 1H, CHH'), 2.30 (s, 3H, 4-Me), 1.30 (d, J=6.8 Hz, 3H, CHMe). $^{13}$C{$^1$H} NMR (CDCl$_3$): δ 177.1, 138.6, 133.8, 132.1, 131.2, 130.2, 127.7, 51.4, 36.5, 20.7, 16.7.

4-Chloro-2,6-dimethylindan-1-one

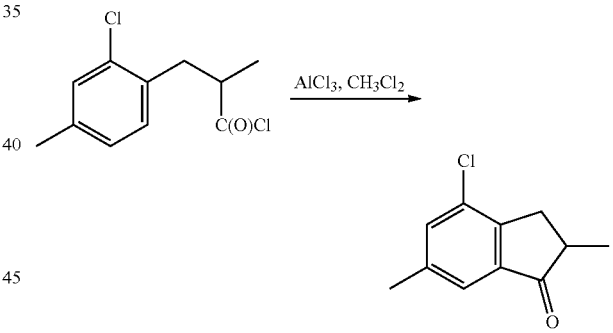

A solution of 123 g (531 mmol) of 3-(2-chloro-4-methylphenyl)-2-methylpropanoyl chloride in 100 ml of dichloromethane was added dropwise to a stirred suspension of 85.0 g (638 mmol) of AlCl$_3$ in 500 ml of dichloromethane at 5° C. This mixture was stirred overnight at room temperature and then poured onto 500 g of crushed ice. The organic layer was separated, and the aqueous layer was extracted with 3×100 ml of dichloromethane. The combined organic extract was washed by aqueous K$_2$CO$_3$, dried over K$_2$CO$_3$, passed through a short pad of silica gel 60 (40-63 μm), and then evaporated to dryness. Crude product was distilled in vacuum to give 98.4 g (95%) of a colorless liquid, b.p. 131-132° C./8 mm Hg.

Anal. calc. for C$_{11}$H$_{11}$ClO: C, 67.87; H, 5.70. Found: C, 68.01; H, 5.69.

$^1$H NMR (CDCl$_3$): δ 7.42 (s, 1H, 7-H), 7.38 (s, 1H, 5-H), 3.32 (dd, J=17.3 Hz, J=7.8 Hz, 1H, 3-CHH'), 2.68-2.76 (m, 1H, 2-H), 2.62 (dd, 1H, J=17.3 Hz, J=3.6 Hz, 3-CHH'), 2.38

(s, 3H, 6-Me), 1.31 (d, J=7.5 Hz, 3H, 2-Me). $^{13}$C{$^1$H} NMR (CDCl$_3$): δ 208.2, 148.0, 139.3, 138.1, 135.0, 132.1, 122.2, 42.0, 33.3, 20.7, 16.1.

4-Chloro-1-methoxy-2,6-dimethylindane

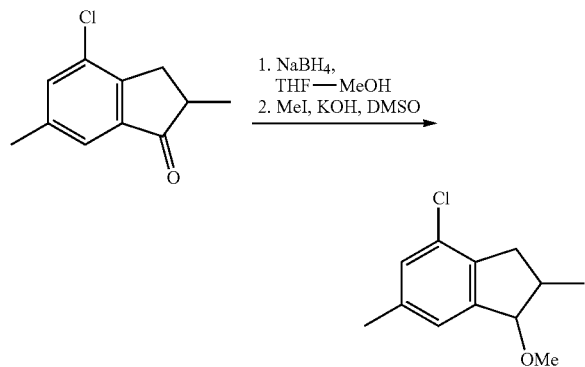

205 ml of methanol was added dropwise by vigorous stirring over 5 h to a mixture of 98.4 g (0.505 mol) of 4-chloro-2,6-dimethylindan-1-one and 29.0 g (0.767 mol) of NaBH4 in 510 ml of THF at 0-5° C. This mixture was stirred overnight at room temperature and then evaporated to dryness. The residue was acidified by 2 M HCl to pH 5-6, and the formed 4-chloro-2,6-dimethylindan-1-ol was extracted with 3×300 ml of dichloromethane. The combined organic extract was dried over Na$_2$SO$_4$ and evaporated to dryness, yielding a white solid. 132 g (2.35 mol) of KOH and 163 g (1.15 mol) of MeI were added to a solution of the so obtained white solid in 800 ml of DMSO. This mixture was stirred for 5 h at ambient temperature. The solution was decanted from the excess of KOH, and the latter was additionally washed with 3×350 ml of dichloromethane. The combined organic extract was washed with 3000 ml of water. The organic layer was separated, and the aqueous layer was extracted with 3×300 ml of dichloromethane. The combined organic extract was washed with 7×1500 ml of water, dried over Na$_2$SO$_4$, and then evaporated to dryness. The residue was distilled in vacuum to give 99.9 g (94%) of the title product consisting of two pairs of enantiomers, b.p. 104-105° C./8 mm Hg.

Anal. calc. for C$_{12}$H$_{15}$ClO: C, 68.40; H, 7.18. Found: C, 68.58; H, 7.25.

Syn-isomers. $^1$H NMR (CDCl$_3$): δ 7.05 (s, 2H, 5-H and 7-H), 4.51 (d, J=5.7 Hz, 1H, 1-H), 3.41 (s, 3H, OMe), 2.92 (dd, J=15.3 Hz, J=6.4 Hz, 1H, 3-CHH'), 2.68-2.59 (m, 2H, 3-CHH' and 2-H), 2.32 (s, 3H, 6-Me), 1.07 (d, J=6.8 Hz, 3H, 2-Me). $^{13}$C{$^1$H} NMR (CDCl$_3$): δ 144.6, 138.3, 137.8, 130.7, 128.7, 124.1, 86.4, 57.0, 38.2, 36.9, 21.0, 13.5.

Anti-isomers. $^1$H NMR (CDCl$_3$): δ 7.05 (s, 1H, 7-H), 7.07 (s, 1H, 5-H), 4.37 (d, J=3.9 Hz, 1H, 1-H), 3.45 (s, 3H, OMe), 3.19 (dd, J=16.2 Hz, J=7.6 Hz, 1H, 3-CHH'), 2.50 (m, 1H, 2-H), 2.42 (dd, J=16.2 Hz, J=5.0 Hz, 1H, 3-CHH'), 2.32 (s, 3H, 6-Me), 1.16 (d, J=6.8 Hz, 3H, 2-Me). $^{13}$C{$^1$H} NMR (CDCl$_3$): δ 144.2, 138.1 (two resonances), 130.7, 128.9, 124.2, 91.8, 56.6, 39.4, 37.2, 21.0, 19.3.

4-(3,5-Dimethylphenyl)-1-methoxy-2,6-dimethylindane

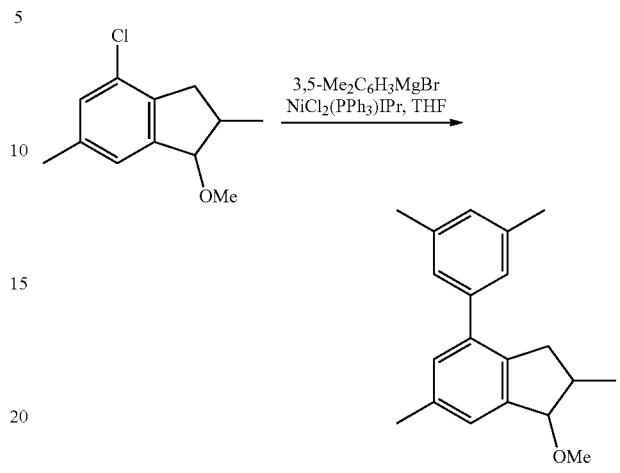

200 ml (200 mmol) of 1.0 M 3,5-di-methylphenylmagnesium bromide in THF was added at room temperature to a mixture of 2.10 g (2.69 mmol, 2.0 mol. %) of NiCl$_2$(PPh$_3$)IPr and 28.4 g (134.7 mmol) of 4-chloro-1-methoxy-2,6-dimethylindane. The resulting mixture was refluxed for 1.5 h, then cooled to room temperature, and 100 ml of water was added. The main part of THF was distilled off on a rotary evaporator. 500 ml of dichloromethane and 1000 ml of 1 M HCl were added to the residue. The organic layer was separated, then the aqueous layer was extracted with 2×100 ml of dichloromethane. The combined organic extract was evaporated to dryness to give a yellow oil. The product was isolated by flash-chromatography on silica gel 60 (40-63 μm; eluent: hexanes-dichloromethane=2:1, vol., then 1:1, vol.). This procedure gave 33.8 g (90%) of 4-(3,5-dimethylphenyl)-1-methoxy-2,6-dimethylindane a colorless thick oil including two diastereomers.

Anal. calc. for C$_{20}$H$_{24}$O: C, 85.67; H, 8.63. Found: C, 86.03; H, 8.80.

$^1$H NMR (CDCl$_3$), mixture of isomers: δ 7.20-6.93 (set of signals, sum 5H); 4.51 (d, J-=5.7 Hz) and 4.39 (d, J-=3.9 Hz) {sum 1H}; 3.49 (s) and 3.45 (s) {sum 3H}; 3.29-3.17 (m), 2.94-2.84 (m), 2.80-2.70 (m) and 2.60-2.37 (m) {sum 3H}; 2.38 (s) and 2.35 (s) {sum 9H}; 1.12 (d, J=6.9 Hz) and 1.06 (d, J=7.1 Hz) {sum 3H}. $^{13}$C{$^1$H} NMR (CDCl$_3$), mixture of isomers: δ 143.50, 143.00, 140.91, 138.68, 138.58, 138.09, 137.64, 136.40, 136.03, 129.51, 129.17, 128.48, 126.35, 124.66, 91.42, 86.23, 56.82, 56.62, 40.12, 39.06, 38.00, 37.85, 21.36, 21.25, 19.17, 13.53.

4/7-(3,5-Dimethylphenyl)-2,5-dimethyl-1H-indene

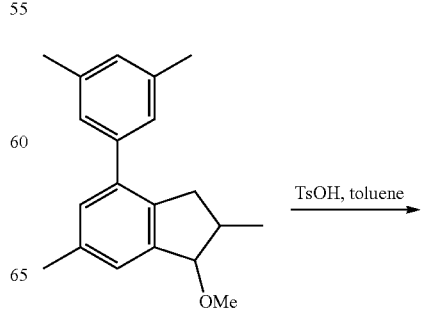

-continued

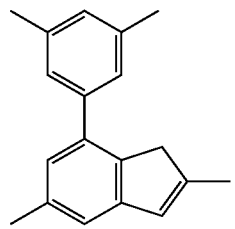

300 mg of TsOH was added to a solution of 33.8 g (120.6 mmol) of 4-(3,5-dimethylphenyl)-1-methoxy-2,6-dimethylindane in 300 ml of toluene and the resulting mixture was refluxed using Dean-Stark head for 10 min. Subsequently one more portion of 150 mg of TsOH was added, and again the formed solution was refluxed using Dean-Stark head for an additional 10 min. After cooling to room temperature the reaction mixture was washed by 200 ml of 10% $K_2CO_3$. The organic layer was separated, and the aqueous layer was additionally extracted with 2×100 ml of dichloromethane. The combined organic extract was dried over anhydrous $K_2CO_3$ and evaporated. The resulting yellow oil was dissolved in hexane. The formed solution was passed through a short pad of silica gel 60 (40-63 μm) and the elute was evaporated to dryness to give 29.1 g (97%) of 7-(3,5-dimethylphenyl)-2,5-dimethyl-1H-indene as a slightly yellowish oil.

Anal. calc. for $C_{19}H_{20}$: C, 91.88; H, 8.12. Found: C, 92.11; H, 8.34.

$^1$H NMR (CDCl$_3$): δ 7.13 (s, 2H), 7.05 (s, 1H), 6.98 (s, 1H), 6.93 (s, 1H), 6.47 (m, 1H), 3.33 (s, 2H), 2.40 (s, 3H), 2.37 (s, 6H), 2.12 (s, 3H). $^{13}$C{$^1$H} NMR (CDCl$_3$): δ 146.65, 146.45, 141.43, 137.84, 137.75, 137.21, 136.41, 128.55, 127.04, 126.23, 125.04, 119.58, 42.41, 21.40, 16.74[3].

[3] two signals in the aliphatic region were merged together

[6-tert-Butyl-4-(3,5-dimethylphenyl)-5-methoxy-2-methyl-1H-inden-1-yl](chloro)dimethylsilane

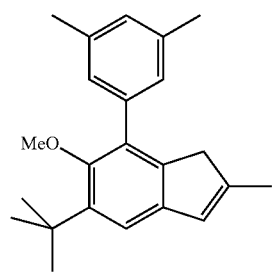

14.6 ml (35.5 mmol) of 2.43 M $^n$BuLi in hexanes was added in one portion to a solution of 11.3 g (35.3 mmol) of 5-tert-butyl-7-(3,5-dimethylphenyl)-6-methoxy-2-methyl-1H-indene in 200 ml of ether cooled to −50° C. The resulting orange solution was stirred overnight at room temperature, then the obtained orange solution containing a yellowish precipitate was cooled to −78° C. (the precipitate almost completely disappeared), and 22.8 g (177 mmol, 5 equiv) of dichlorodimethylsilane was added in one portion. The formed solution was warmed to room temperature and stirred overnight at room temperature. The resulting mixture was filtered through glass frit (G4). The precipitate was additionally washed by 2×10 ml of ether. The combined filtrate was evaporated to dryness to give the title material as slightly orange oil which was used without additional purification.

$^1$H NMR (CDCl$_3$): δ 7.38 (s, 1H), 7.08 (s, 2H), 6.98 (s, 1H), 6.43 (s, 1H), 3.53 (s, 1H), 3.25 (s, 3H), 2.37 (s, 6H), 2.19 (s, 3H), 1.43 (s, 9H), 0.43 (s, 3H), 0.17 (s, 3H). $^{13}$C{$^1$H} NMR (CDCl$_3$): δ 155.79, 145.87, 143.74, 137.99, 137.55, 137.49, 136.75, 128.32, 127.87, 127.55, 126.65, 120.86, 60.46, 49.99, 35.15, 31.17, 21.42, 17.56, 1.11, −0.58.

[2-methyl-4-(3,5-dimethylphenyl)-5-methoxy-6-tert-butyl-1H-inden-1-yl][2,6-dimethyl-4-(3,5-dimethylphenyl)-1H-inden-1-yl]dimethylsilane

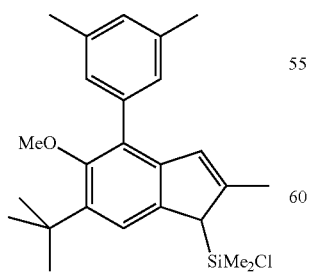

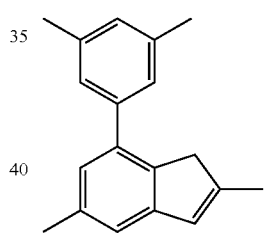

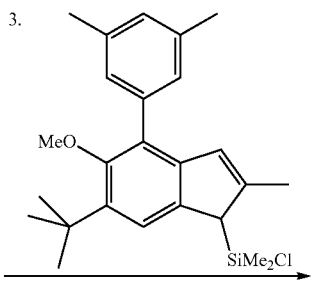

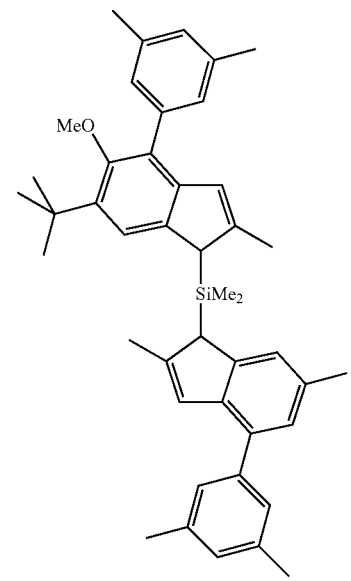

14.6 ml (35.5 mmol) of 2.43 M $^n$BuLi in hexanes was added in one portion to a solution of 8.78 g (35.35 mmol) of 7-(3,5-dimethylphenyl)-2,5-dimethyl-1H-indene in 200 ml of ether at −50° C. This mixture was stirred overnight at room temperature, then the resulting yellowish solution containing a large amount of yellow precipitate was cooled to −50° C., then 40 ml of THF and 200 mg of CuCN were added in sequence. The resulting mixture was stirred for 0.5 h at −25° C., then a solution of [6-tert-butyl-4-(3,5-dimethylphenyl)-5-methoxy-2-methyl-1H-inden-1-yl](chloro)dimethylsilane (35.32 mmol) in 200 ml of ether was added in one portion. This mixture was stirred overnight at ambient temperature, then it was filtered through a glass frit (G4) and the obtained yellow solution was evaporated to dryness. The title product was isolated by flash-chromatography on silica gel 60 (40-63 μm; eluent: hexanes-dichloromethane=10:1, vol., then 3:1, vol.). This procedure gave 17.5 g (79%) of [2-methyl-4-(3,5-dimethylphenyl)-5-methoxy-6-tert-butyl-1H-inden-1-yl][2,6-dimethyl-4-(3,5-dimethylphenyl)-1H-inden-1-yl]dimethylsilane.

Anal. calc. for $C_{44}H_{52}OSi$: C, 84.56; H, 8.39. Found: C, 84.85; H, 8.78.

$^1$H NMR (CDCl$_3$): δ 7.51-7.02 (set of signals, sum 7H), 6.99 (s, 2H), 6.79 (s, 1H), 6.45 (s, 1H), 3.68 and 3.66 (2m, sum 2H), 3.28 and 3.26 (2s, sum 3H), 2.44-2.32 (set of signals, 15H), 2.18 and 2.15 (2s, sum 6H), 1.43 and 1.42 (2s, sum 9H), −0.16, −0.18, −0.19 and −0.25 (4s, sum 6H). $^{13}$C{$^1$H} NMR (CDCl$_3$): δ 155.36, 147.36, 147.28, 146.50, 146.25, 146.00, 143.75, 143.70, 141.41, 140.42, 139.21, 138.24, 137.76, 137.53, 137.16, 137.09, 133.94, 132.44, 132.32, 128.34, 128.24, 127.94, 127.53, 127.15, 126.74, 126.41, 126.10, 126.05, 125.84, 125.75, 123.04, 122.84, 120.56, 120.50, 60.51, 47.37, 47.30, 47.23, 47.15, 35.16, 31.27, 31.23, 21.68, 21.59, 21.43, 17.95, 17.85, −5.27, −5.28, −5.37, −5.85 rac-anti-Me$_2$Si(2,6-Me$_2$-4-(3,5-Me$_2$Ph)Ind)(2-Me-4-(3,5-Me$_2$Ph)-5-OMe-6-tBu-Ind)ZrCl$_2$-MC-IE2

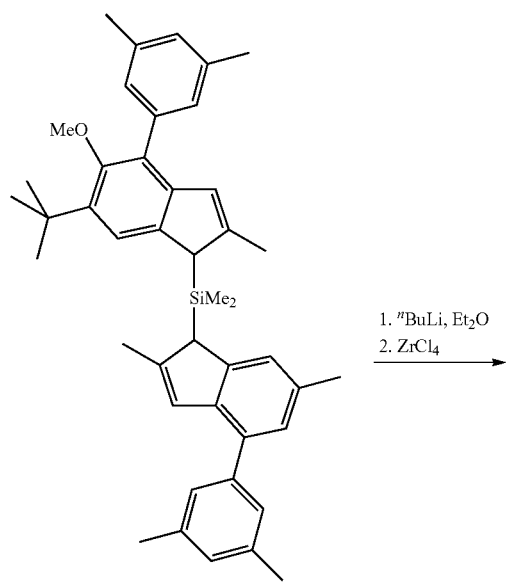

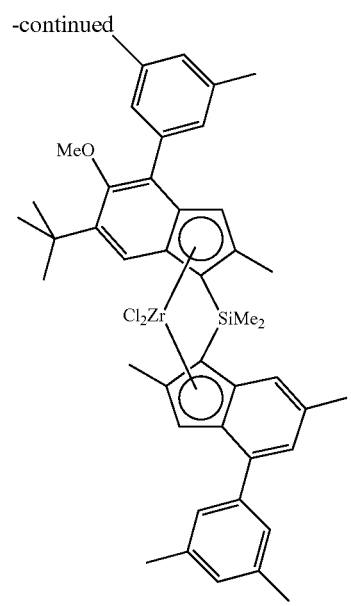

23.1 ml (56.1 mmol) of 2.43 M $^n$BuLi in hexanes was added in one portion to a solution of 17.53 g (28.05 mmol) of [2-methyl-4-(3,5-dimethylphenyl)-5-methoxy-6-tert-butyl-1H-inden-1-yl][2,6-dimethyl-4-(3,5-dimethylphenyl)-1H-inden-1-yl]dimethylsilane in 200 ml of ether cooled to −50° C. This mixture was stirred overnight at room temperature. The resulting reddish solution containing a yellowish precipitate was cooled to −50° C., and 6.54 g (28.06 mmol) of ZrCl$_4$ was added. The reaction mixture was stirred for 24 h at room temperature giving a light red suspension with orange precipitate. This mixture was evaporated to dryness, and the residue was treated with 200 ml of hot toluene. This mixture was filtered while hot through glass frit (G4), and the filtrate was evaporated to ca. 60 ml. The orange crystalline powder precipitated from this solution in 3 h at room temperature was collected and dried in vacuum. This procedure gave 3.60 g of pure anti-dimethylsilanediyl[2-methyl-4-(3,5-dimethylphenyl)-5-methoxy-6-tert-butyl-inden-1-yl][2,6-dimethyl-4-(3,5-dimethylphenyl)-inden-1-yl]zirconium dichloride. The mother liquor was evaporated almost to dryness, and the residue was triturated with 50 ml of ether. The insoluble orange precipitate was filtered off (G3) to give 5.01 g of a ca. 93:7 mixture of anti-/syn-complexes. Reddish crystalline powder precipitated overnight at −30° C. from the filtrate was collected and dried in vacuum. This procedure gave 1.98 g of pure syn-dimethylsilanediyl[2-methyl-4-(3,5-dimethylphenyl)-5-methoxy-6-tert-butyl-inden-1-yl][2,6-dimethyl-4-(3,5-dimethylphenyl)-inden-1-yl]zirconium dichloride. After standing for several days at room temperature, an additional portion of red crystalline powder precipitated from the mother liquor. This precipitate was filtered off to give 4.91 g of a ca. 96:4 mixture of syn-/anti-complexes. Thus, the total yield of syn- and anti-complexes isolated in this synthesis was 15.5 g (70%).

Anti-dimethylsilanediyl[2-methyl-4-(3,5-dimethylphenyl)-5-methoxy-6-tert-butyl-inden-1-yl] [2,6-dimethyl-4-(3,5-dimethylphenyl)-inden-1-yl]zirconium dichloride Anal. calc. for $C_{44}H_{50}Cl_2OSiZr$: C): δ 7.31; H, 6.42. Found: C, 67.58; H, 6.59.

$^1$H NMR (CDCl$_3$, 400 MHz, 27° C.): δ 7.49 (s, 1H), 7.36 (s, 1H), 7.28 (s, 2H), 7.22 (s, 1H), 7.32-7.12 (two very br.s, 2H), 6.98 (s, 1H), 6.95 (2s, sum 2H) 6.57 (s, 1H), 3.43 (s, 3H), 2.35 (2s, sum 9H), 2.32 (s, 6H), 2.23 (s, 3H), 2.17 (s, 3H), 1.39 (s, 9H), 1.30 (s, 3H), 1.29 (s, 3H). $^{13}$C{$^1$H} NMR (CDCl$_3$): δ 159.81, 144.25, 139.44, 138.46, 138.02, 137.90, 136.75, 135.59, 135.44, 134.26, 133.57, 130.51, 129.36, 129.03, 128.86, 128.73, 128.22, 127.77, 127.39, 127.08, 126.41, 123.16, 122.59, 122.03, 121.72, 120.81, 81.98, 81.95, 62.61, 35.77, 30.40, 22.11, 21.45, 21.35, 18.40, 18.25, 2.68, 2.52.

Syn-dimethylsilanediyl[2-methyl-4-(3,5-dimethylphenyl)-5-methoxy-6-tert-butyl-inden-1-yl] [2,6-dimethyl-4-(3,5-dimethylphenyl)-inden-1-yl]zirconium dichloride Anal. calc. for C$_{44}$H$_{50}$Cl$_2$OSiZr: C, δ 7.31; H, 6.42. Found: C, 67.56; H, 6.60.

$^1$H NMR (CDCl$_3$, 400 MHz, 27° C.): δ 7.50 (s, 1H), 7.35 (s, 1H), 7.25 (s, 2H), 7.31-7.08 (two very br.s, 2H), 7.01 (s, 1H), 6.96 (s, 1H), 6.95 (s, 1H) 6.84 (s, 1H), 6.48 (s, 1H), 3.26 (s, 3H), 2.42 (s, 3H), 2.36, 2.35 and 2.34 (3s, sum 15H), 2.30 (s, 3H), 1.43 (s, 3H), 1.35 (s, 9H), 1.20 (s, 3H). $^{13}$C{$^1$H} NMR (CDCl$_3$): δ 158.95, 143.13, 139.34, 137.91, 137.78, 137.59, 136.81, 136.15, 135.78, 135.11, 134.48, 132.32, 129.25, 129.21, 128.80, 128.35, 127.33, 126.32, 124.00, 122.89, 121.45, 121.24, 121.00, 83.74, 83.67, 62.36, 35.55, 30.31, 22.72, 21.44, 18.53, 18.45, 2.92, 2.65.

Synthesis of Inventive Metallocene MC-IE3 rac-anti-Me$_2$Si(2,6-Me$_2$-4-(3,5-Me$_2$Ph)Ind)(2-Me-4-(3,5-Me$_2$Ph)-5-OMe-6-tBu-Ind)ZrMe$_2$

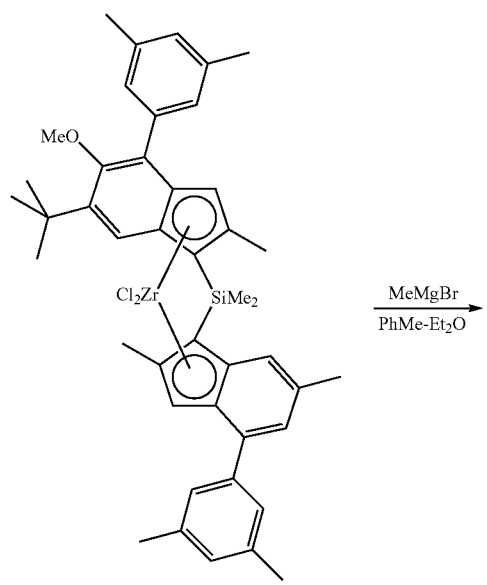

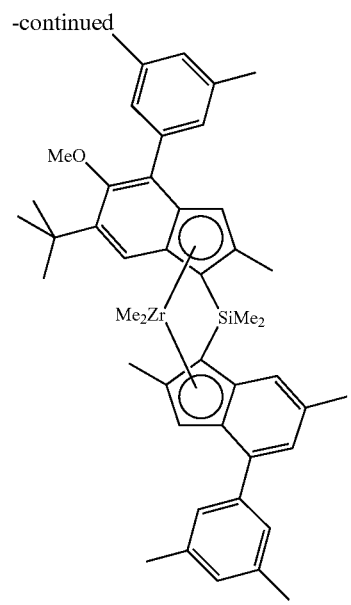

7.0 ml (18.9 mmol) of 2.7 M MeMgBr in ether was added to a solution of 3.53 g (4.5 mmol) of anti-dimethylsilanediyl [2-methyl-4-(3,5-dimethylphenyl)5-methoxy-6-tert-butylinden-1-yl][2,6-dimethyl-4-(3,5-dimethylphenyl)inden-1-yl] zirconium dichloride (contaminated with 7% of syn-isomer) in a mixture of 100 ml of toluene and 50 ml of ether. The resulting mixture was stirred at room temperature for 2 days (during which time color was changed from red to yellow). The resulting suspension was evaporated to ca. 50 ml, filtered through glass frit (G4), and the filter cake was additionally washed with 10 ml of warm toluene. The combined filtrate was evaporated to ca. 30 ml, filtered through glass frit (G4), and the filter cake was washed by 10 ml of warm toluene. Then the mother liquor was evaporated to ca. 10 ml, and 20 ml of n-hexane was added. Yellow powder precipitated from this mixture overnight at room temperature was collected and dried in vacuum. This procedure gave 2.2 g (66%) of pure anti-complex.

Anti-dimethylsilanediyl[2-methyl-4-(3,5-dimethylphenyl)5-methoxy-6-tert-butylinden-1-yl][2,6-dimethyl-4-(3,5-dimethylphenyl)inden-1-yl]zirconium dimethyl Anal. calc. for C$_{46}$H$_{56}$OSiZr: C, 74.24; H, 7.58. Found: C, 74.35; H, 7.85.

$^1$H NMR (CDCl$_3$, 400 MHz, 27° C.): δ 7.41 (s, 1H), 7.27 (s, 2H), 7.24 (d, J=1.0 Hz, 1H), 7.18 (s, 2H), 7.15 (d, J=1.0 Hz, 1H), 6.99 (s, 1H), 6.97 (s, 1H), 6.95 (s, 1H), 6.58 (s, 1H), 3.33 (s, 3H), 2.36 (s, 6H), 2.33 (s, 6H), 2.31 (s, 3H), 2.10 (s, 3H), 2.02 (s, 3H), 1.38 (s, 9H), 1.09 (s, 6H), −1.04 (s, 3H), −1.16 (s, 3H).

Synthesis of Inventive Metallocene MC-IE4

Diethyl (2,2-dimethylpropylidene)malonate

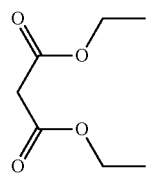 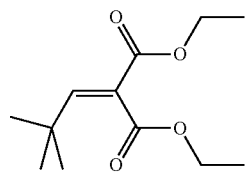

In a 1-liter flask, 38.4 g (0.28 mol) of ZnCl$_2$ was added in one portion by vigorous stirring to a mixture of 320 g (2.0 mol) of diethyl malonate, 172 g (2.0 mol) of pivalaldehyde, and 256 g (2.51 mol) of acetic anhydride. This mixture spontaneously warmed to ca. 105° C. The formed red mixture was refluxed for 36 h, then cooled to ambient temperature, and 800 ml of toluene was added. This solution was washed with 3×500 ml of water. The combined aqueous solution was extracted with 2×350 ml of toluene. The combined toluene extract and solution was dried over K$_2$CO$_3$, passed through ca. 7 cm layer of silica gel 60 (40-63 μm) on glass frit, and then evaporated to dryness. Fractional rectification of the residue gave yellowish oil of the title product, b.p. 132-135° C./20 mm Hg. Yield 254 g (56%).

Anal. calc. for C$_{12}$H$_{20}$O$_4$: C, 63.14; H, 8.83. Found: C, 63.19; H, 8.85.

$^1$H NMR (CDCl$_3$): δ 6.84 (s, 1H, CH$^t$Bu), 4.24 (q, J=7.1 Hz, 2H, CH$_2$Me), 4.18 (q, J=7.1 Hz, 2H, CH$_2$Me), 1.29 (t, J=7.1 Hz, 3H, CH$_2$Me), 1.24 (t, J=7.1 Hz, 3H, CH$_2$Me), 1.11 (s, 9H, $^t$Bu). $^{13}$C{$^1$H} NMR (CDCl$_3$): δ 166.9, 164.4, 154.9, 125.3, 61.3, 61.2, 34.1, 28.8, 14.0, 13.9.

Diethyl (2,2-dimethylpropyl)malonate

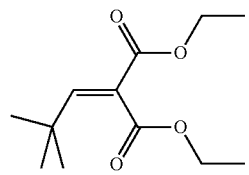 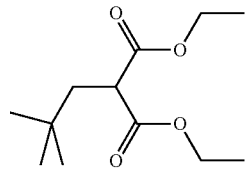

In 2-liter stainless steel pressure reactor, 1.60 g of 10% Pd/C was added to a solution of 114 g (0.50 mol) of diethyl (2,2-dimethylpropylidene)malonate in 650 ml of ethanol. Hydrogenation was carried out at 5 atm of hydrogen gas for 6 h at 40° C. The following GC analysis showed that conversion of the starting material into the title product was almost quantitative. The reaction mixture was added to 1500 cm$^3$ of cold water, and the product was extracted by 3×300 ml of dichloromethane. The combined organic extract was passed through short layer of silica gel 60 (40-63 μm), evaporated in vacuum, and then used without further purification. Yield of the title material was almost quantitative.

Anal. calc. for C$_{12}$H$_{22}$O$_4$: C, 62.58; H, 9.63. Found: C, 62.80; H, 9.78.

$^1$H NMR (CDCl$_3$): δ 4.16 (q, J=7.1 Hz, 4H, CH$_2$Me), 3.35 (t, J=6.3 Hz, 1H, CH$_2$CH), 1.90 (d, J=6.3 Hz, 2H, $^t$BuCH$_2$), 1.24 (t, J=7.1 Hz, 6H, CH$_2$Me), 0.87 (s, 9H, $^t$Bu). $^{13}$C{$^1$H} NMR (CDCl$_3$): δ 170.3, 61.3, 48.8, 41.8, 30.4, 29.0, 14.0.

(2,2-Dimethylpropyl)malonic acid (incl. 25% of Toluene)

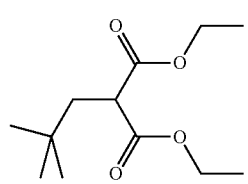 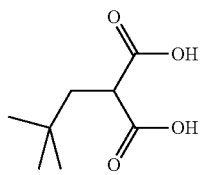

A solution of 125 g of KOH in 1000 cm$^3$ of water was added to a solution of the above obtained diethyl (2,2-dimethylpropyl)malonate in 500 cm$^3$ of methanol. The obtained mixture was refluxed for 5 h, and then methanol and ethanol were distilled off at atmospheric pressure. Ca. 3000 cm$^3$ of water was added to the residue, then the obtained solution was acidified by concentrated HCl solution to pH 1. The formed product was extracted with 3×500 ml of ether. To the combined extract 200 ml of toluene was added, and the obtained solution was evaporated in vacuum to give a ca. 3 to 1 mixture of the title product and toluene (based on NMR spectroscopy). This mixture was used without further purification.

$^1$H NMR (CDCl$_3$): δ 12.1 (br.s, 2H, CO$_2$H), 3.51 (t, J=6.3 Hz, 1H, CH$_2$CH), 2.0 (d, J=6.3 Hz, 2H, CH$_2$CH), 0.97 (s, 9H, $^t$Bu). $^{13}$C{$^1$H} NMR (CDCl$_3$): δ 176.4, 48.6, 41.8, 30.6, 28.9.

2-(2,2-Dimethylpropyl)acrylic acid

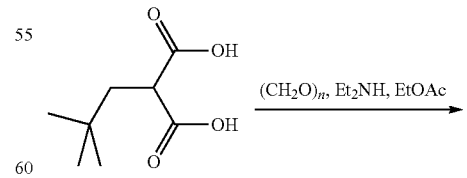

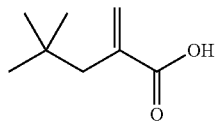

Diethylamine (60.0 ml, 42.4 g, 0.58 mol) was added dropwise by vigorous stirring to a solution of the above-obtained (2,2-dimethylpropyl)malonic acid (0.50 mol given almost quantitative yields on the hydrogenation and saponification stages) in 750 ml of ethyl acetate at 5° C. Then 21.1 g (0.702 mmol) of paraform was added, and the formed mixture was refluxed for 6 h, then cooled to 5° C., and finally, 500 ml of ether and 800 ml of 4.5 N HCl were added. After shaking for 30 sec the organic layer was separated, the aqueous layer was extracted with 2×300 ml of ether. The combined organic extract was dried over $Na_2SO_4$ and then evaporated to dryness. Fractional rectification of the residue gave colorless oil (b.p. 120-122° C./20 mm Hg) which crystallizes on storage at room temperature. Yield 62 g (87%) of the title compound.

Anal. calc. for $C_8H_{14}O_2$: C, 67.57; H, 9.92. Found: C, 67.49; H, 9.96.

$^1$H NMR ($CDCl_3$): δ 11.9 (br.s, 1H, $CO_2$H), 6.36 (m, 1H, HH'C=), 6.58 (m, 1H, HH'C=), 2.26 (s, 2H, $^tBuCH_2$), 0.89 (s, 9H, $^tBu$). $^{13}C\{^1H\}$ NMR ($CDCl_3$): δ 173.9, 138.1, 129.7, 43.8, 31.5, 29.1.

2-neopentyl-5-methoxy-6-tert-butylindan-1-one and 2-neopentyl-4-tert-butyl-7-methoxyindan-1-one

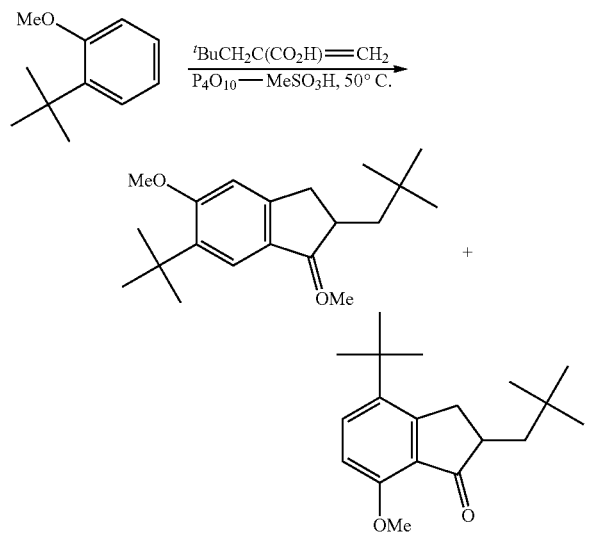

A mixture of 62.3 g (0.379 mol) of 1-tert-butyl-2-methoxybenzene and 59.9 g (0.421 mol) of 2-(2,2-dimethylpropyl)acrylic acid was added dropwise by vigorous stirring for ca. 40 min to Iton reagent obtained from 110 g of $P_4O_{10}$ and 560 ml of methanesulfonic acid at 50° C. The resulting mixture was stirred for additional 40 min at this temperature and then poured on a mixture of 1000 cm$^3$ of ice and 1000 cm$^3$ of cold water. The product was extracted by 3×250 ml of dichloromethane. The combined organic extract was washed by aqueous $K_2CO_3$, filtered through glass frit (G3), and evaporated to dryness. The residue was dissolved in 220 ml of hexanes. Crystalline solid precipitated from this solution at 5° C. was filtered off, washed by 2×150 ml of hexanes, and dried in vacuum. This procedure gave 51.9 g of white solid as a ca. 5 to 1 mixture of 2-neopentyl-5-methoxy-6-tert-butylindan-1-one and 2-neopentyl-4-tert-butyl-7-methoxyindan-1-one. These isomers were separated by flash chromatography on silica gel 60 (40-63 µm, 1500 cm$^3$ of silica gel, eluent: hexanes-dichloromethane-ether=20:10:1, vol.). This procedure gave 42.4 g (39%) of 22-neopentyl-5-methoxy-6-tert-butylindan-1-one and 8.47 g (8%) of 2-neopentyl-4-tert-butyl-7-methoxyindan-1-one. Additional quantity of the products was isolated from mother liquid by flash chromatography on silica gel 60 followed by crystallization of the crude products from hexanes. This procedure gave additional 4.38 g (4%) of 2-neopentyl-5-methoxy-6-tert-butylindan-1-one and 12.0 g (11%) of 2-neopentyl-4-tert-butyl-7-methoxyindan-1-one. Thus, the overall yields were 43 and 19% for 5- and 7-methoxy-substituted products, respectively.

2-neopentyl-5-methoxy-6-tert-butylindan-1-one

Anal. calc. for $C_{19}H_{28}O_2$: C, 79.12; H, 9.78. Found: C, 79.29; H, 9.85.

$^1$H NMR ($CDCl_3$): δ 7.67 (s, 1H, 7-H in indanone), 6.85 (s, 1H, 4-H in indanone), 3.91 (s, 3H, OMe), 3.33 (dd, J=17.1 Hz, J=7.6 Hz, 1H, 3-HH' in indanone), 2.75 (dd, J=17.1 Hz, J=3.8 Hz, 1H, 3-CHH' in indanone), 2.56 (m, 1H, 2-CH in indanone), 2.07 (dd, J=13.8 Hz, J=1.5 Hz, 1H, CHH'$^t$Bu), 1.36 (s, 9H, 6-$^t$Bu in indanone), 1.18 (dd, J=13.8 Hz, J=10.7 Hz, 1H, CHH'$^t$Bu), 0.99 (s, 9H, $^tBuCH_2$). $^{13}C\{^1H\}$ NMR ($CDCl_3$): δ 208.0, 164.6, 154.8, 138.7, 128.9, 122.0, 107.6, 55.2, 46.0, 45.2, 35.8, 35.1, 31.0, 29.9, 29.6.

2-neopentyl-4-tert-butyl-7-methoxyindan-1-one

Anal. calc. for C19H28O2: C, 79.12; H, 9.78. Found: C, 79.33; H, 9.90.

$^1$H NMR ($CDCl_3$): δ 7.51 (d, J=8.7 Hz, 1H, 5-H in indanone), 6.72 (d, J=8.7 Hz, 1H, 4-H in indanone), 3.90 (s, 3H, OMe), 3.59 (dd, J=16.8 Hz, J=7.9 Hz, 1H, 3-HH' in indanone), 2.91 (dd, J=16.8 Hz, J=4.7 Hz, 1H, 3-CHH' in indanone), 2.53 (m, 1H, 2-CH in indanone), 2.10 (dd, J=13.9 Hz, J=2.1 Hz, 1H, CHH'$^t$Bu), 1.39 (s, 9H, 4-$^t$Bu in indanone), 1.19 (dd, J=13.9 Hz, J=10.1 Hz, 1H, CHH'$^t$Bu), 1.00 (s, 9H, $^tBuCH_2$). $^{13}C\{^1H\}$ NMR ($CDCl_3$): δ 207.0, 156.3, 153.5, 139.1, 133.2, 125.1, 108.8, 55.6, 45.7, 45.0, 37.7, 35.1, 30.9, 30.7, 29.9.

2-neopentyl-4-bromo-5-methoxy-6-tert-butylindan-1-one

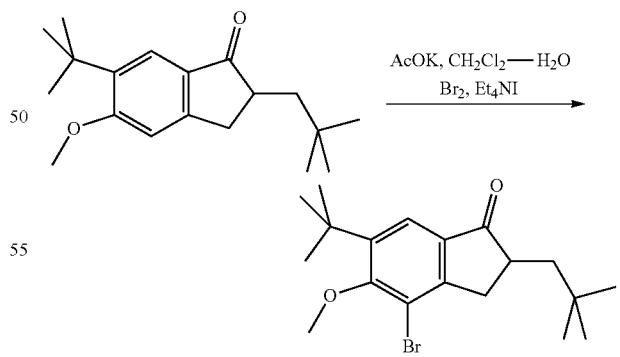

Bromine (23.5 g, 0.147 mol) was added dropwise by vigorous stirring for 5 min to a mixture of 42.4 g (0.146 mol) of 2-(2,2-dimethylpropyl)-5-methoxy-6-tert-butylindan-1-one, 58.0 g (0.426 mol) of sodium acetate trihydrate, 0.93 g of Et$_4$NI, 130 ml of dichloromethane, and 250 ml of water at 5° C. The resulting mixture was stirred for additional 1 h at this temperature. Further on, this mixture was washed by aqueous Na₂SO₃ to remove an excess of bromine, and then 500 ml of dichloromethane was added. The organic layer was separated, and the aqueous layer was extracted with 2×250 ml of dichloromethane. The combined organic extract was dried over K₂CO₃ and then evaporated to dryness to give 54.8 g of yellowish oil which crystallizes on storage at room temperature. This product was used without further purification.

Anal. calc. for $C_{19}H_{27}BrO_2$: C, 62.13; H, 7.41. Found: C, 62.32; H, 7.55.

¹H NMR (CDCl₃): δ 7.68 (s, 1H, 7-H in indanone), 4.00 (s, 3H, OMe), 3.32 (dd, J=17.5 Hz, J=7.8 Hz, 1H, 3-HH' in indanone), 2.69 (dd, J=17.4 Hz, J=4.0 Hz, 1H, 3-CHH' in indanone), 2.59 (m, 1H, 2-CH in indanone), 2.06 (dd, J=13.9 Hz, J=1.8 Hz, 1H, CHH'ᵗBu), 1.38 (s, 9H, 6-ᵗBu in indanone), 1.22 (dd, J=13.9 Hz, J=10.5 Hz, 1H, CHH'ᵗBu), 1.01 (s, 9H, ᵗBuCH₂). ¹³C {¹H} NMR (CDCl₃): δ 208.0, 162.7, 154.2, 145.4, 132.8, 121.4, 116.5, 61.6, 45.9, 45.3, 37.2, 35.7, 30.9, 30.6, 29.9.

2-neopentyl-4-(3,5-dimethylphenyl)-5-methoxy-6-tert-butylindan-1-one

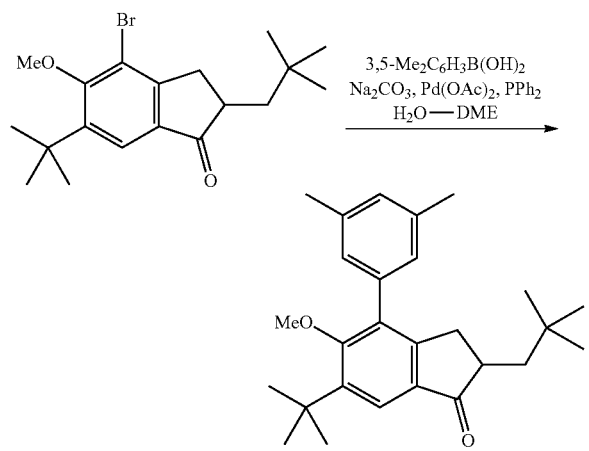

A mixture of 36.73 g (100.0 mmol) of 2-neopentyl-4-bromo-5-methoxy-6-tert-butylindan-1-one, 18.78 g (125.0 mmol, 1.25 equiv.) of (3,5-dimethylphenyl)boronic acid, 28.7 g (270.8 mmol) of Na₂CO₃, 1.19 g (5.3 mmol, 5.3 mol. %) of Pd(OAc)₂, 2.76 g (10.5 mmol, 10.5 mol. %) of PPh₃, 130 ml of water, and 320 ml of 1,2-dimethoxyethane was refluxed for 6.5 h. DME was evaporated using a rotary evaporator, 500 ml of water and 400 ml of dichloromethane were added to the residue. The organic layer was separated, and the aqueous one was additionally extracted with 2×150 ml of dichloromethane. The combined extract was dried over K₂CO₃ and then evaporated to dryness to give black oil. The crude product was purified by flash chromatography on silica gel 60 (40-63 μm, hexanes-dichloromethane=3:1, vol., then, 1:3, vol.) to give 38.9 g (99%) of 2-neopentyl-4-(3,5-dimethylphenyl)-5-methoxy-6-tert-butylindan-1-one as a grey solid mass.

¹H NMR (CDCl₃): δ 7.73 (s, 1H), 7.05-6.98 (m, 3H), 3.30 (s, 3H), 3.13 (dd, J=17.1 Hz, J=7.5 Hz, 1H), 2.61-2.47 (m, 2H), 2.38 (s, 6H), 2.08 (dd, J=13.9 Hz, J=1.7 Hz, 1H), 1.42 (s, 9H), 1.18 (dd, J=13.9 Hz, J=10.0 Hz, 1H), 0.94 (s, 9H). ¹³C{¹H} NMR (CDCl₃): δ 208.76, 163.42, 153.03, 143.22, 138.06, 136.21, 132.55, 130.98, 129.08, 127.19, 121.15, 60.48, 45.81, 45.28, 35.41, 35.34, 30.88, 30.53, 29.86, 21.38.

2-neopentyl-5-tert-butyl-6-methoxy-7-(3,5-dimethylphenyl)-1H-indene

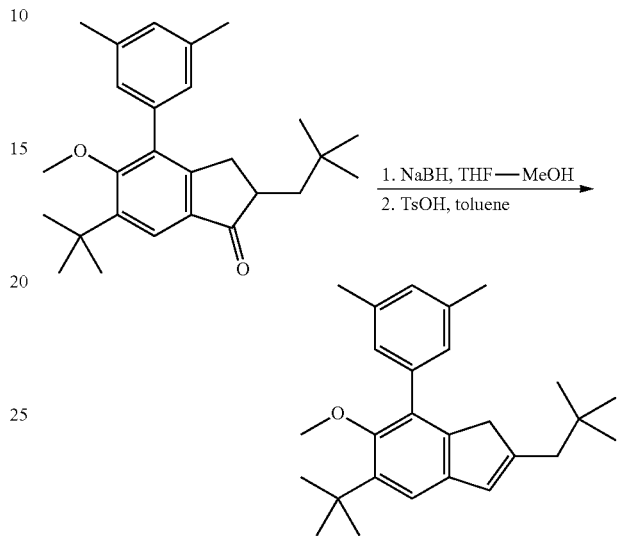

NaBH4 (5.0 g, 132 mmol) was added to a solution of 38.9 g (99.1 mmol) of 2-neopentyl-4-(3,5-dimethylphenyl)-5-methoxy-6-tert-butylindan-1-one in 200 ml of THF cooled to 5° C. Then, 100 ml of methanol was added dropwise to this mixture with vigorous stirring over ca. 7 h at 5° C. The resulting mixture was evaporated to dryness, and the residue was partitioned between 500 ml of dichloromethane and 500 ml of 1 M HCl. The organic layer was separated; the aqueous layer was additionally extracted with 100 ml of dichloromethane. The combined organic extract was evaporated to dryness to give slightly yellowish oil. TsOH (200 mg) was added to a solution of this oil in 300 ml of toluene, this mixture was refluxed with Dean-Stark head for 10 min and then cooled to room temperature using water bath. The formed solution was washed with 10% Na₂CO₃, the organic layer was separated, and the aqueous layer was extracted with 200 ml of dichloromethane. The combined organic extract was dried over K₂CO₃ and then passed through a short layer of silica gel 60 (40-63 μm). The silica gel layer was additionally washed with 100 ml of dichloromethane. The combined organic elute was evaporated to dryness, and the resulting solid was heated with 150 ml of n-hexane. The obtained heterogeneous mixture was allowed to stand overnight at room temperature and then at +5° C. for 30 min. The formed precipitate was filtered off (G3) and then dried in vacuo. This procedure gave 34.02 g (91%) of pure 2-neopentyl-5-tert-butyl-7-(3,5-dimethylphenyl)-6-methoxy-1H-indene.

¹H NMR (CDCl₃): δ 7.25 (s, 1H), 7.09 (s, 2H), 6.99 (s, 1H), 6.48 (s, 1H), 3.25 (s, 3H), 3.19 (s, 2H), 2.37 (s, 6H), 2.29 (s, 2H), 1.44 (s, 9H), 0.92 (s, 9H). ¹³C{¹H} NMR (CDCl₃): δ 154.34, 147.38, 141.88, 140.87, 140.46, 138.24, 137.66, 131.72, 129.20, 128.46, 127.22, 117.16, 60.65, 45.15, 43.74, 35.14, 31.77, 31.01, 29.86, 21.44.

Bis[2-neopentyl-4-(3,5-dimethylphenyl)-5-methoxy-6-tert-butyl-1H-inden-1-yl]dimethylsilane

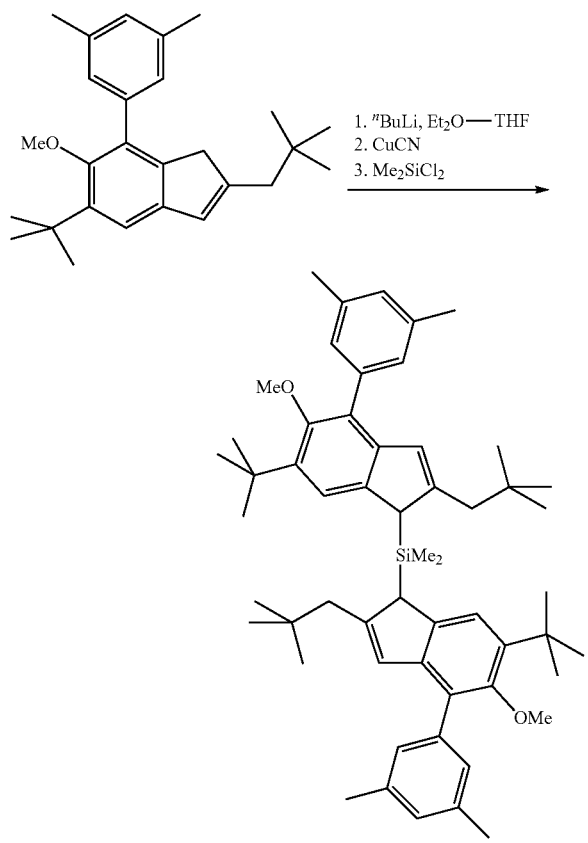

$^n$BuLi in hexanes (2.43 M, 18.8 ml, 45.68 mmol) was added in one portion to a suspension of 17.2 g (45.68 mmol) of 2-neopentyl-5-tert-butyl-6-methoxy-7-(3,5-dimethylphenyl)-1H-indene in 250 ml of ether at −50° C. This mixture was stirred overnight at room temperature, then the resulting yellowish solution was cooled to −40° C., and 300 mg of CuCN was added. The obtained mixture was stirred for 30 min at −25° C., and then 2.95 g (22.86 mmol) of dichlorodimethylsilane was added in one portion. This mixture was stirred overnight at room temperature, then it was diluted with 250 ml of dichloromethane and filtered through a pad of silica gel 60 (40-63 μm) which was additionally washed by 8×50 ml of dichloromethane. The combined filtrate was evaporated under reduced pressure to give a white semi-solid mass. This mass was triturated with 200 ml of n-hexane, the precipitated white powder was filtered off and washed by 2×25 ml of n-hexane. This procedure gave 8.38 g (45%) of bis[2-neopentyl-4-(3,5-dimethylphenyl)-5-methoxy-6-tert-butyl-1H-inden-1-yl]dimethylsilane as a pure rac-isomer. The mother liquor was evaporated to dryness, and the residue was heated to melt and dried under vacuum. This procedure gave 10.8 g (58%) of bis[2-neopentyl-4-(3,5-dimethylphenyl)-5-methoxy-6-tert-butyl-1H-inden-1-yl]dimethylsilane (a ca. 7:1 mixture of meso-/rac-stereoisomers in favor of meso-). Thus, the total yield of bis[2-neopentyl-4-(3,5-dimethylphenyl)-5-methoxy-6-tert-butyl-1H-inden-1-yl]dimethylsilane isolated in this synthesis was 19.18 g (~100%).

rac-Bis[2-neopentyl-4-(3,5-dimethylphenyl)-5-methoxy-6-tert-butyl-1H-inden-1-yl]dimethylsilane $^1$H NMR (CDCl$_3$): δ 7.72 (s, 1H), 7.15 (s, 2H), 7.00 (s, 1H), 6.40 (s, 1H), 4.03 (s, 1H), 3.27 (s, 3H), 2.38 (s, 6H), 2.22 (d, J=13.4 Hz, 1H), 2.06 (d, J=13.4 Hz, 1H), 1.44 (s, 9H), 0.80 (s, 9H), −0.37 (s, 3H). $^{13}$C {$^1$H} NMR (CDCl$_3$): δ 155.22, 149.41, 143.41, 139.46, 138.19, 137.45, 137.15, 128.19, 128.01, 127.68, 127.53, 119.94, 60.54, 47.72, 44.72, 35.17, 32.21, 31.26, 29.94, 21.45, −5.30.

meso-Bis[2-neopentyl-4-(3,5-dimethylphenyl)-5-methoxy-6-tert-butyl-1H-inden-1-yl]dimethylsilane $^1$H NMR (CDCl$_3$): δ 7.32 (s, 2H), 7.14 (s, 4H), 6.99 (s, 2H), 6.44 (s, 2H), 3.80 (s, 2H), 3.25 (s, 6H), 2.42 (d, J=13.4 Hz, 2H), 2.38 (s, 12H), 2.26 (d, J=13.4 Hz, 2H), 1.44 (s, 18H), 0.89 (s, 18H), −0.10 (s, 3H), −0.50 (s, 3H). $^{13}$C{$^1$H} NMR (CDCl$_3$): δ 155.14, 149.74, 143.18, 139.65, 138.12, 137.44, 137.09, 128.17, 128.02, 127.44, 127.23, 120.30, 60.46, 47.72, 45.32, 35.18, 32.35, 31.28, 29.93, 21.44, −2.27, −4.07.

Rac-dimethylsilanediyl-bis[2-neopentyl-4-(3,5-dimethylphenyl)-5-methoxy-6-tert-butylinden-1-yl] zirconium dichloride

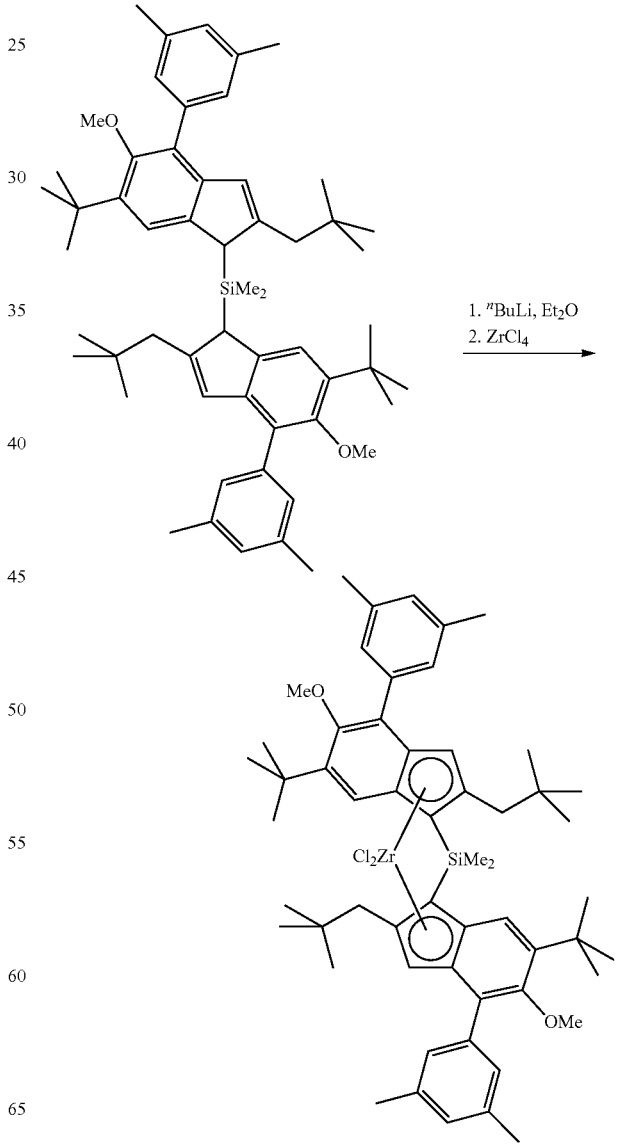

nBuLi in hexanes (2.43 M, 18.5 ml, 45.0 mmol) was added in one portion to a white suspension of 18.17 g (22.45 mmol) of bis[2-neopentyl-4-(3,5-dimethylphenyl)-5-methoxy-6-tert-butyl-1H-inden-1-yl]dimethylsilane in 250 ml of ether cooled to −20° C. This mixture was stirred for 4 h at room temperature, then the resulting yellow solution was cooled to −50° C., and 5.23 g (22.44 mmol) of $ZrCl_4$ was added. The reaction mixture was stirred for 48 h at room temperature to give red solution with some precipitate. This mixture was evaporated to dryness. The residue was heated with 150 ml of toluene, and the formed suspension was filtered while hot through glass frit (G4). The filtrate was evaporated to dryness, and the residue was dissolved in 50 ml of n-hexane. Yellow powder precipitated spontaneously from this solution was collected and dried in vacuum. This procedure gave 2.9 g of rac-zirconocene (13.3%, ca. 95% purity, impurity is not the meso-complex). The mother liquor was evaporated almost to dryness, and the residue was dissolved in 50 ml of n-hexane. Orange powder precipitated from this solution overnight at room temperature was collected and dried under vacuum. This procedure gave 1.5 g (6.9%) of meso-zirconocene. The mother liquor was evaporated once again to dryness, and the residue was dried for 5 h in vacuum, then it was triturated with 40 ml of n-hexane. The obtained suspension was filtered through glass frit (G3), and the obtained solid (on filter) was dried in vacuum to give 6.3 g of a ca. 70 to 30 mixture of rac- and meso-zirconocenes. Thus, the total yield of rac- and meso-zirconocenes isolated in this synthesis was 10.7 g (49.2%).

2.9 g of rac-zirconocene of ca. 95% purity was dissolved in 10 ml of ether, and 15 ml of n-hexane was added to this solution. Yellow powder precipitated from this solution was collected and dried in vacuum. This procedure gave 0.67 g of pure rac-zirconocene. The mother liquor was evaporated to dryness, and the residue was triturated with 10 ml of n-hexane. The obtained suspension was filtered through glass frit (G3), and the isolated precipitate was dried in vacuum to give 1.86 g of rac-zirconocene (ca. 95% purity).

Rac-dimethylsilanediyl-bis[2-neopentyl-4-(3,5-dimethylphenyl)-5-methoxy-6-tert-butylinden-1-yl]zirconium dichloride Anal. calc. for $C_{56}H_{74}Cl_2O_2SiZr$: C, 69.38; H, 7.69. Found: C, 69.61; H, 7.94.

$^1$H NMR (CDCl$_3$): δ 7.50 (s, 1H), 7.41-7.06 (br.s, 2H), 6.94 (s, 1H), 6.53 (s, 1H), 3.41 (s, 3H), 2.71 (d, J=13.4 Hz, 1H), 2.34 (s, 6H), 2.05 (d, J=13.4 Hz, 1H), 1.41 (s, 9H), 1.31 (s, 3H), 0.81 (s, 9H). $^{13}$C{$^1$H} NMR (CDCl$_3$): δ 159.66, 143.73, 138.57, 137.62, 136.67, 133.71, 128.75, 127.48, 127.26, 122.57, 120.79, 120.68, 82.11, 62.54, 45.74, 35.79, 33.12, 30.41, 29.75, 21.49, 5.40.

Meso-dimethylsilanediyl-bis[2-neopentyl-4-(3,5-dimethylphenyl)-5-methoxy-6-tert-butylinden-1-yl] zirconium dichloride $^1$H NMR (CDCl$_3$): δ 7.43 (s, 2H), 7.55-7.04 (br.s, 4H), 6.95 (s, 2H), 6.50 (s, 2H), 3.24 (s, 6H), 2.84 (d, J=13.4 Hz, 2H), 2.42 (d, J=13.4 Hz, 2H), 2.35 (s, 12H), 1.42 (s, 3H), 1.37 (s, 18H), 1.22 (s, 3H), 0.81 (s, 18H). $^{13}$C{$^1$H} NMR (CDCl$_3$): 158.58, 143.95, 138.45, 137.54, 136.38, 134.19, 128.73, 127.51, 127.16, 125.77, 123.06, 120.15, 84.18, 62.03, 45.76, 35.68, 33.33, 30.61, 29.72, 21.40, 7.25, 3.15.

In the Table 1 below a summary of the metallocenes employed in the Catalyst examples is disclosed. IE1 and IE2 are inventive examples, CE1-CE8 are comparative examples:

TABLE 1

Catalyst examples (free of external carrier)

| Catalyst Example | Metallocene | MC structure |
|---|---|---|
| IE1 | MC-IE1<br>rac-Me$_2$Si(2-Me-4-Ph-5-OMe-6-tBuInd)$_2$ZrCl$_2$ | 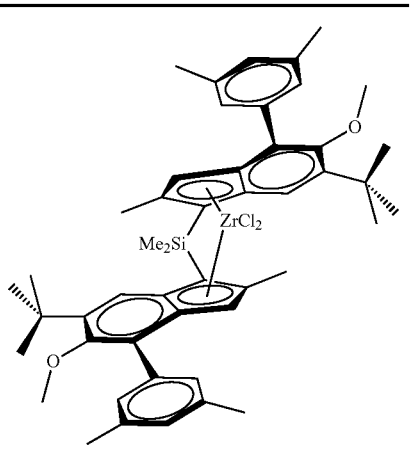 |

TABLE 1-continued
Catalyst examples (free of external carrier)
| Catalyst Example | Metallocene | MC structure |
|---|---|---|
| IE2 (a + b) | MC-IE2<br>rac-anti-Me$_2$Si(2,6-Me$_2$-4-(3,5-Me$_2$Ph)Ind)(2-Me-4-(3,5-Me$_2$Ph)-5-OMe-6-tBu-Ind)ZrCl$_2$ | 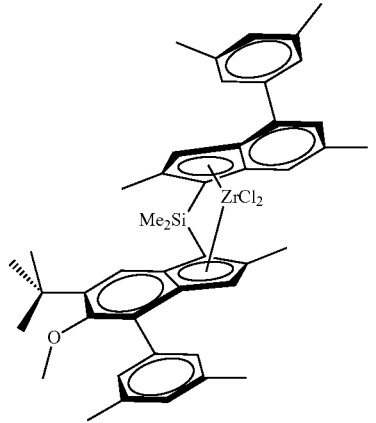 |
| CE1 | MC-CE1<br>rac-Me$_2$Si(2-Me-4-PhInd)$_2$ZrCl$_2$,<br>(EP576970) | 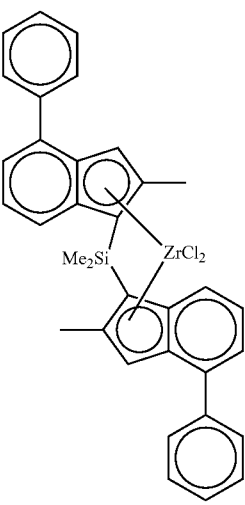 |
| CE2 | MC-CE2<br>rac-Me$_2$Si(2-Me-4-Ph-5-OMe-6-tBuInd)$_2$ZrCl$_2$<br>(WO 2007/116034) | 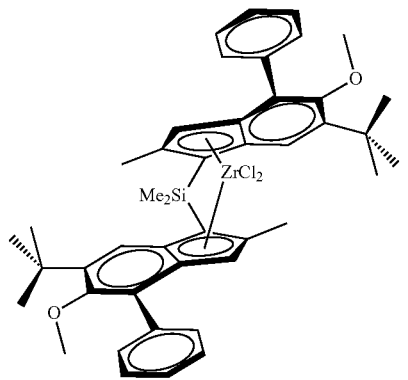 |

TABLE 1-continued

Catalyst examples (free of external carrier)

| Catalyst Example | Metallocene | MC structure |
| --- | --- | --- |
| CE3 | MC-CE3<br>rac-Me$_2$Si[2-Me-4-(3,5-tBu2Ph)Ind]$_2$ZrCl$_2$<br>(WO2002/002576) | |
| CE4 | MC-CE4<br>rac-Me$_2$Si(2-Me-4-(3,5-tBu$_2$Ph)-5-OMe-6-tBu-Ind)$_2$ZrCl$_2$ | |
| CE5 | MC-CE5<br>rac-Me$_2$Si(2-Me-4-(3',5'-Me$_2$Ph)Ind)$_2$ZrCl$_2$<br>(Journal of Molecular Catalysis A: Chemical 412 (2016) 39-46.) | |

TABLE 1-continued

Catalyst examples (free of external carrier)

| Catalyst Example | Metallocene | MC structure |
|---|---|---|
| CE6 | MC-CE6<br>Rac-Me$_2$Si (2-Me-4-(3',5'-iPr$_2$Ph)-5-OMe-6-tBu-Ind)$_2$ZrCl$_2$ | |
| CE7 | MC-CE7<br>Me$_2$Si(2-Me-4-(3,5-di-tBu-phenyl)-5-OMe-6-tBu-Ind-1-yl][2,6-Me$_2$-4-(3,5-di-tBu)-Ind-1-yl]ZrCl$_2$ | |

TABLE 1-continued

Catalyst examples (free of external carrier)

| Catalyst Example | Metallocene | MC structure |
|---|---|---|
| CE8 | MC-CE8<br>rac-Me(CyHex)Si(2-Me-4-(4'-tBuPh)Ind)₂ZrCl₂ | (structure diagram) |

Catalyst Preparation Examples—Free of External Carrier

Inventive Catalyst IE1

Inside the glovebox, 86.2 mg of dry and degassed surfactant solution (1H,1H-Perfluoro(2-methyl-3-oxahexan-1-ol (CAS number 26537-88-2) (Apollo Scientific) degassed by argon bubbling prior to use) was mixed with 2 mL of MAO in a septum bottle and left to react overnight. The following day, 65.02 mg of metallocene MC-IE1 (0,076 mmol, 1 equivalent) was dissolved with 4 mL of the MAO solution in another septum bottle and left to stir inside the glovebox.

After 60 minutes, 4 mL of the MAO-metallocene solution and 1 mL of the surfactant solution were successively added into a 50 mL emulsification glass reactor containing 40 mL of PFC at −10° C. and equipped with an overhead stirrer (stirring speed=600 rpm). Total amount of MAO is 5 mL (300 equivalents). A red emulsion formed immediately and stirred during 15 minutes at −10° C./600 rpm. Then the emulsion was transferred via a 2/4 teflon tube to 100 mL of hot PFC at 90° C. and stirred at 600 rpm until the transfer is completed. Then the speed was reduced to 300 rpm. After 15 minute stirring, the oil bath was removed and the stirrer turned off. The catalyst was left to settle up on top of the PFC and after 35 minutes the solvent was siphoned off. The remaining red catalyst was dried during 2 hours at 50° C. over an argon flow. 0.9 g of a red free flowing powder was obtained.

Inventive Catalyst IE2a

Inside the glovebox, 86 mg of dry and degassed surfactant solution as in IE1 was mixed with 2 mL of MAO in a septum bottle and left to react overnight. The following day, 59.6 mg of MC-IE2 (0,076 mmol, 1 equivalent) were dissolved with 4 mL of the MAO solution in another septum bottle and left to stir inside the glovebox. After 60 minutes, 4 mL of the MAO-metallocene solution and 1 mL of the surfactant solution were successively added into a 50 mL emulsification glass reactor containing 40 mL of PFC at −10° C. and equipped with an overhead stirrer (stirring speed=600 rpm). Total amount of MAO is 5 mL (300 equivalents). A red emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.73 g of a red free flowing powder was obtained.

Inventive Catalyst IE2b

Inside the glovebox, 72 mg of dry and degassed surfactant solution as in IE1 was mixed with 2 mL of MAO in a septum bottle and left to react overnight. The following day, 39.8 mg MC-IE2 (0,076 mmol, 1 equivalent) were dissolved with 4 mL of the MAO solution in another septum bottle and left to stir inside the glovebox. After 60 minutes, 4 mL of the MAO-metallocene solution and 1 mL of the surfactant solution were successively added into a 50 mL emulsification glass reactor containing 40 mL of PFC at −10° C. and equipped with an overhead stirrer (stirring speed=600 rpm). Total amount of MAO is 5 mL (450 equivalents). A red emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.72 g of a red free flowing powder was obtained.

Comparative Catalyst CE1

Inside the glovebox, 80 µL of dry and degassed surfactant solution (mixture of perfluoroalkylethyl acrylate esters (CAS 65605-70-1) degassed by argon bubbling prior to use) was mixed with 2 mL of MAO in a septum bottle and left to react overnight. The following day, 47.8 mg of MC-CE1 (0,076 mmol, 1 equivalent) were dissolved with 4 mL of the MAO solution in another septum bottle and left to stir inside the glovebox. After 60 minutes, 4 mL of the MAO-metallocene solution and 1 mL of the surfactant solution were successively added into a 50 mL emulsification glass reactor containing 40 mL of PFC at −10° C. and equipped with an overhead stirrer (stirring speed=600 rpm). Total amount of MAO is 5 mL (300 equivalents). A red emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.72 g of a red free flowing powder was obtained.

Comparative Catalyst CE2

Inside the glovebox, 80 µL of dry and degassed surfactant solution as in CE1 was mixed with 2 mL of MAO in a septum bottle and left to react overnight. The following day, 60.9 mg of MC-CE2 (0,076 mmol, 1 equivalent) were dissolved with 4 mL of the MAO solution in another septum bottle and left to stir inside the glovebox.

After 60 minutes, 4 mL of the MAO-metallocene solution and 1 mL of the surfactant solution were successively added into a 50 mL emulsification glass reactor containing 40 mL of PFC at −10° C. and equipped with an overhead stirrer (stirring speed=600 rpm). Total amount of MAO is 5 mL (300 equivalents). A red emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.64 g of a red free flowing powder was obtained.

Comparative Catalyst CE3

Inside the glovebox, 80 µL of dry and degassed surfactant solution as in CE1 was mixed with 2 mL of MAO in a septum bottle and left to react overnight. The following day, 64.9 mg of MC-CE3 (0,076 mmol, 1 equivalent) were dissolved with 4 mL of the MAO solution in another septum bottle and left to stir inside the glovebox.

After 60 minutes, 4 mL of the MAO-metallocene solution and 1 mL of the surfactant solution were successively added into a 50 mL emulsification glass reactor containing 40 mL of PFC at −10° C. and equipped with an overhead stirrer (stirring speed=600 rpm). Total amount of MAO is 5 mL (300 equivalents). A red emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.45 g of a red free flowing powder was obtained.

Comparative Catalyst CE4

Inside the glovebox, 80 µL of dry and degassed surfactant solution as in CE1 was mixed with 2 mL of MAO in a septum bottle and left to react overnight. The following day, 78.0 mg of MC-CE4 (0,076 mmol, 1 equivalent) were dissolved with 4 mL of the MAO solution in another septum bottle and left to stir inside the glovebox.

After 60 minutes, 4 mL of the MAO-metallocene solution and 1 mL of the surfactant solution were successively added into a 50 mL emulsification glass reactor containing 40 mL of PFC at −10° C. and equipped with an overhead stirrer (stirring speed=600 rpm). Total amount of MAO is 5 mL (300 equivalents). A red emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.37 g of a red free flowing powder was obtained.

Comparative Catalyst CE5

Inside the glovebox, 54 µL of dry and degassed surfactant solution as in CE1 was mixed with 2 mL of MAO in a septum bottle and left to react overnight. The following day, 51.95 mg of metallocene MC-CE5 (0,076 mmol, 1 equivalent) was mixed with 4 ml of 30 wt.-% Chemtura MAO in a septum bottle and the solution was stirred for 60 minutes and then 1 mL of the MAO/surfactant solution was added. The mixture was left to react at room temperature inside the glovebox. After 30 minutes stirring, the MAO-metallocene-surfactant solution was added into a 50 mL emulsification glass reactor containing 40 mL of PFC at −10° C. and equipped with an overhead stirrer (stirring speed=600 rpm). Total amount of MAO is 5 mL (300 equivalents). A red emulsion formed immediately and stirred during 15 minutes at −10° C./600 rpm. Then the emulsion was transferred via a 2/4 teflon tube to 100 mL of hot PFC at 90° C. and stirred at 600 rpm until the transfer is completed. Then the speed was reduced to 300 rpm. After 15 minute stirring, the oil bath was removed and the stirrer turned off. The catalyst was left to settle up on top of the PFC and after 35 minutes the solvent was siphoned off. The remaining red catalyst was dried during 2 hours at 50° C. over an argon flow. 1.1 g of a red free flowing powder was obtained.

Comparative Catalyst CE6

Inside the glovebox, 80 µL of dry and degassed surfactant solution as in CE1 was mixed with 2 mL of MAO in a septum bottle and left to react overnight. The following day, 73.6 mg of MC-CE6 (0,076 mmol, 1 equivalent) were dissolved with 4 mL of the MAO solution in another septum bottle and left to stir inside the glovebox.

After 60 minutes, 4 mL of the MAO-metallocene solution and 1 mL of the surfactant solution were successively added into a 50 mL emulsification glass reactor containing 40 mL of PFC at −10° C. and equipped with an overhead stirrer (stirring speed=600 rpm). Total amount of MAO is 5 mL (300 equivalents). A red emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.80 g of a red free flowing powder was obtained.

Comparative Catalyst CE7a

Inside the glovebox, 80 μL of dry and degassed surfactant solution as in CE1 was mixed with 2 mL of MAO in a septum bottle and left to react overnight. The following day, 72.4 mg of MC-CE7 (0,076 mmol, 1 equivalent) were dissolved with 4 mL of the MAO solution in another septum bottle and left to stir inside the glovebox. After 60 minutes, 4 mL of the MAO-metallocene solution and 1 mL of the surfactant solution were successively added into a 50 mL emulsification glass reactor containing 40 mL of PFC at −10° C. and equipped with an overhead stirrer (stirring speed=600 rpm). Total amount of MAO is 5 mL (300 equivalents). A red emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.51 g of a red free flowing powder was obtained.

Comparative Catalyst CE7b

Inside the glovebox, 52.6 mg of dry and degassed surfactant solution 3-(Nonafluoro-tert-butyl)propan-1-ol ((CAS number 14115-49-2) (Apollo Scientific) degassed by argon bubbling prior to use) was mixed with 2 mL of MAO in a septum bottle and left to react overnight. The following day, 72.3 mg of metallocene MC-IE1 (0,076 mmol, 1 equivalent) was mixed with 4 ml of 30 wt.-% Chemtura MAO in a septum bottle and the solution was stirred for 60 minutes.

After, 4 mL of the MAO-metallocene solution and 1 mL of the surfactant solution were successively added into a 50 mL emulsification glass reactor containing 40 mL of PFC at −10° C. and equipped with an overhead stirrer (stirring speed=600 rpm). Total amount of MAO is 5 mL (300 equivalents). A red emulsion formed immediately and stirred during 15 minutes at −10° C./600 rpm. Then the emulsion was transferred via a 2/4 teflon tube to 100 mL of hot PFC at 90° C. and stirred at 600 rpm until the transfer is completed. Then the speed was reduced to 300 rpm. After 15 minute stirring, the oil bath was removed and the stirrer turned off. The catalyst was left to settle up on top of the PFC and after 35 minutes the solvent was siphoned off. The remaining red catalyst was dried during 2 hours at 50° C. over an argon flow. 0.7 g of a red free flowing powder was obtained.

Comparative Catalyst CE8

Catalyst was prepared according to the procedure of CE7 using 80 μL of dry and degassed surfactant solution as in CE1 and using as metallocene MC-CE8, in an amount of 61.5 mg. 0.51 g of a red free flowing powder was obtained.

TABLE 2

Catalyst elemental analysis

| Catalyst | ICP Zr (wt.-%) | Al/Zr (mol/mol) |
| --- | --- | --- |
| IE1 | 0.35 | 328 |
| IE2a | 0.41 | 288 |
| IE2b | 0.28 | 422 |
| CE8 | 0.29 | 273 |
| CE7a | 0.32 | 364 |
| CE7b | 0.39 | 310 |
| CE6 | 0.35 | 286 |
| CE5 | 0.35 | 308 |
| CE4 | 0.28 | 399 |
| CE3 | 0.36 | 338 |
| CE2 | 0.25 | 276 |
| CE1 | 0.41 | 298 |

Off-Line Prepolymerisation

Off-line prepolymerised catalysts IE1-p, IE2a-p, IE2b-p, CE2-p, CE7b-p and CE8-p Catalysts IE1, IE2a, IE2b, CE2, CE7b and CE8 were off-line prepolymerised according to the following procedure:

Dry and degassed perfluoro-1,3-dimethylcyclohexane (15 ml) and catalyst to be pre-polymerised was loaded into a 125 ml reactor inside a glovebox and the reactor was sealed. The reactor was then taken out from the glove box and placed inside a water cooled bath kept at 25° C. The overhead stirrer and feeding lines were connected and stirring speed was set to 450 rpm.

The experiment was started by opening the propylene feed into the reactor. The total pressure in the reactor was raised to 5 barg and held constant by propylene feed via mass flow controller until the target degree of polymerisation was reached. The reaction was stopped by flashing the volatile components. The reactor was then taken back to glovebox and inside glove box the reactor content was poured into a glass vessel and perfluoro-1.3-dimethylcyclohexane was evaporated until a constant weight was obtained to yield the pre-polymerised catalyst. Catalyst amounts and yield of the off-line prepolymerised catalysts are given in Table 3.

TABLE 3

Off-line prepolymerisation experiments

| Catalyst | Catalyst amount mg | Off-line Prepolymerised Catalyst code | DP* wt/wt |
| --- | --- | --- | --- |
| IE1 | 408.5 | IE1-p | 3.2 |
| IE2a | 392.0 | IE2a-p | 3.2 |
| IE2b | 399.5 | IE2b-p | 3.4 |
| CE2b | 665.6 | CE2b-p | 2.7 |
| CE7b | 390.5 | CE7-p | 3.5 |
| CE8 | 405.2 | CE8-p | 3.5 |

*DP-prepolymerisation degree defined as weight of polymer matrix/weight of solid catalyst before pre-polymerisation step.

Polymerisation Examples
Chemical used in the polymerisation experiments:

| | |
|---|---|
| PFC | Perfluoro-1,3-dimethylcyclohexane purchased from F2 chemicals Limited (trade name Flutec PP3) CAS-No. 335-27-3 |
| Triethylaluminum | Triethylaluminum purchased from Chemtura (trade name TEA-S) CAS-No. 97-93-8 (>94%), triethylaluminium CAS-No. 1116-70-7 (<5%), tributylaluminium |
| Propylene | Propylene obtained from Borealis Polymers Oy. Before use, purified by passing through columns containing $Al_2O_3$/Cu catalyst, molecular sieves and COS Selexorb. |
| Ethylene | Purchased from AGA, HiQ grade 3.5. Before use, purified by passing through columns containing alumina, CuO/Cu COS Selexorb, molecular sieves |
| Nitrogen | Purchased from AGA, HiQ nitrogen, grade 5.0. Before use, purified to remove $O_2$ and $H_2O$. |
| Hydrogen | Purchased from AGA (grade 6.0) and purified before use. |
| Pentane | Purchased from Scharlau (reagent grade, ≥99%). Before use, pentane is dried with molecular sieves and bubbled with nitrogen. |

Homopolymerisation of Propylene
Polymerisation Procedure for Propylene Homopolymerisation in Bulk The polymerisations were performed in a 5 litre jacketed stainless-steel reactor equipped with a stirrer, lines for monomer and hydrogen, an exhaust line and feeding systems for catalyst and scavenger.

The catalyst feeder comprises two stainless steel cylinders in series. Inside a glovebox, desired amount of catalyst (5 to 35 mg) was loaded into the lower steel cylinder of the feeder and the second cylinder, containing 5 ml of dry PFC, was attached on top. The steel cylinder of the scavenger feeder was filled with 200 μl of triethylaluminum and 5 ml of dry pentane. Outside glovebox, the feed cylinders were attached to the reactor and the connections flushed with nitrogen. Reactor temperature was controlled to 20° C. The contents of the scavenger feeder was flushed into the reactor with nitrogen over pressure. Then, desired amount of hydrogen (mmol, see table 4a), followed by 1100 g of liquid propylene, was fed into the reactor. Stirring speed was set to 400 rpm. The reactor temperature was stabilised to 20° C. and after minimum of 5 minutes, the polymerisation was started by injecting the catalyst into the reactor as described in the following. The valve between the two cylinders of the catalyst feeder was opened and the catalyst was then immediately flushed into the reactor with nitrogen over pressure. The feeder was pressurised three times with nitrogen and flushed into the reactor. Total nitrogen loading to reactor was about 0.42 mol.

After 5 minutes prepolymerisation at 20° C., the reactor temperature was raised to 70° C. over a period of 15 minutes. The polymerisation was continued at 70° C. for 60 minutes and then stopped by flushing the reactor to normal pressure. Polymer was collected after flushing the reactor with nitrogen several times, left to dry until constant mass was reached, and then weighed to record the yield.

The catalyst activity was calculated based on the 60 minute period according to the following formula:

$$\text{Catalyst Activity (kg-}PP\text{/g-}Cat\text{/h)} = \frac{\text{amount of polymer produced (kg)}}{\text{catalyst loading (g)} \times \text{polymerisation time (h)}}$$

$C_3/C_2$ random copolymerisation

The polymerisations were performed in a 5 litre jacketed stainless-steel reactor equipped with a stirrer, lines for monomers and hydrogen, an exhaust line and feeding systems for catalyst and scavenger.

The catalyst feeder comprises two stainless steel cylinders in series. Inside a glovebox, desired amount of catalyst (5 to 20 mg) was loaded into the lower steel cylinder of the feeder and the second cylinder, containing 5 ml of dry PFC, was attached on top. The steel cylinder of the scavenger feeder was filled with 200 μl of triethylaluminum and 5 ml of dry pentane. Outside glovebox, the feed cylinders were attached to the reactor and the connections flushed with nitrogen. Reactor temperature was controlled to 30° C. The content of the scavenger feeder was flushed into the reactor with nitrogen over pressure. Then, desired amount of hydrogen (6 mmol), followed by 1100 g of liquid propylene and 50 g of ethylene, was fed into the reactor. Stirring speed was set to 400 rpm. The reactor temperature was stabilised to 30° C. and after minimum of 5 minutes, the polymerisation was started by injecting the catalyst into the reactor as described in the following. The valve between the two cylinders of the catalyst feeder was opened and the catalyst was then immediately flushed into the reactor with nitrogen over pressure. The feeder was pressurised three times with nitrogen and flushed into the reactor. Total nitrogen loading to reactor was about 0.38 mol.

The reactor temperature was raised to 70° C. over a period of 15 minutes. The polymerisation was continued at 70° C. for 30 minutes and then stopped by flushing the reactor to normal pressure. Polymer was collected after flushing the reactor with nitrogen several times, left to dry until constant mass was reached, and then weighed to record the yield.

The catalyst activity was calculated based on the 30 minute period according to the following formula:

$$\text{Catalyst Activity (kg-}PP\text{/g-}Cat\text{/h)} = \frac{\text{amount of polymer produced (kg)}}{\text{catalyst loading (g)} \times \text{polymerisation time (h)}}$$

Polymerisation results of C3/C2 random copolymerisations are collected in Table 5.

Propylene-Hexene Copolymerisation with Off-Line Prepolymerised Catalysts

Polymerisation grade propylene was additionally purified according to standard industrial procedures.

1-Hexene (INEOS alpha olefins) was additionally purified by purging with N2 and drying over 3A molecular sieves supplied by M-Braun. Triethylaluminium (TEAL) was received from Chemtura as 0.62 molar solution in n-heptane and used as received.

A stirred autoclave (equipped with a ribbon stirrer) with a total volume of 21.2 dm³ containing 0.2 bar-g of propylene is filled with additional 4.45 kg propylene and the chosen amount of 1-hexene. After addition of 0.8 ml TEAL solution using a stream of 250 g propylene, the reactor is stirred at 20° C. and 250 rpm for at least 20 min. Afterwards the reactor is brought up to the set pre-polymerization temperature (HB-Therm) and the catalyst is injected as described in the following.

The solid, pre-polymerized catalyst (type and amount as listed in the tables) is loaded into a 5-mL stainless steel vial inside the glove box. The vial is attached to the autoclave, then a second 5-mL vial containing 4 ml n-heptane and pressurized with 10 bars of N2 is added on top. The chosen amount of H2 is dosed into the reactor via flow controller. The valve between the two vials is opened and the solid catalyst is contacted with heptane under N2 pressure for 2 s, and then flushed into the reactor with 250 g propylene. Stirring speed is held at 250 rpm and pre-polymerisation is run for the set time. Now the polymerisation temperature is increased to 75° C. The reactor temperature is held constant throughout the polymerization. The polymerization time is measured starting when the temperature is 2° C. below the set polymerization temperature. When the polymerization time 60 min has lapsed, the reaction is stopped by injecting 5 ml ethanol, cooling the reactor and flashing the volatile components. After flushing the reactor 3 times with N2 and one vacuum/N2 cycle, the product is taken out and dried overnight in a hood. 50-100 g of the polymer is additivated with 0.2 wt % Ionol and 0.1 wt % PEPQ (dissolved in acetone) and dried also overnight in a hood and additionally 2 hours in a vacuum drying oven at 60° C.

The propylene-hexene copolymerisation conditions and results are listed in tables 6 and 7.

TABLE 4a

Propylene homopolymerisation in liquid propylene. Polymerisation time 60 minutes. Tp = 70° C.

| Pol. Example* | Catalyst | Catalyst (mg) | H2 (mmol) | Yield (g) | Activity (kg-PP/g-Cat/h) | Metal activity (kg-PP/g-Zr/h) | MFR2 (g/10 min) | MFR21 (g/10 min) | Tm (° C.) |
|---|---|---|---|---|---|---|---|---|---|
| PC-1.1 | CE1 | 32.3 | 1 | 323 | 10 | 2437 | | 7.4 | 150.8 |
| PC-1.2 | CE1 | 28.5 | 6 | 319 | 11.2 | 2733 | | 42.9 | 150 |
| PC-1.3 | CE1 | 22 | 15 | 258 | 11.7 | 2856 | 5.21 | | 149.9 |
| PC-2.1 | CE2 | 5.9 | 1 | 167 | 28.4 | 11349 | | 2.2 | 143.4 |
| PC-2.2 | CE2 | 5.6 | 6 | 284 | 50.7 | 20264 | | 19 | 143.9 |
| PC-2.3 | CE2 | 5 | 15 | 265 | 53.1 | 21224 | 3.3 | | 144 |
| PC-3.1 | CE3 | 11.1 | 1 | 99 | 9 | 3088 | | 9.4 | 156.5 |
| PC-3.2 | CE3 | 5.5 | 6 | 100 | 18.2 | 6270 | 1.9 | | 157.5 |
| PC-3.3 | CE3 | 10.7 | 15 | 218 | 20.4 | 7025 | 21 | | 156.6 |
| PC-4.1 | CE4 | 13.2 | 1 | 91 | 6.9 | 2465 | | 32.8 | 156 |
| PC-4.2 | CE4 | 8.6 | 6 | 130 | 15.1 | 5395 | 17.1 | | 155.3 |
| PC-4.3 | CE4 | 11 | 15 | 190 | 17.3 | 6172 | 259 | | 155.3 |
| PC-5.1 | CE5 | 10.4 | 1 | 140 | 13.5 | 3852 | | 5.26 | 151.3 |
| PC-5.2 | CE5 | 9.7 | 6 | 254 | 26.2 | 7476 | | 40.8 | 151.9 |
| PC-5.3 | CE5 | 10.7 | 15 | 281 | 26.3 | 7511 | 5.26 | | 151.8 |
| PC-6.1 | CE6 | 10.1 | 1 | 111 | 10.9 | 3126 | | 4.71 | 154.5 |
| PC-6.2 | CE6 | 9.3 | 6 | 233 | 25 | 7152 | 1.71 | | 153.6 |
| PC-6.3 | CE6 | 9.9 | 15 | 260 | 26.2 | 7492 | 20.5 | | 152.5 |
| PC-7.1 | CE7a | 11.1 | 1 | 110 | 9.9 | 3102 | | 21 | 156.7 |
| PC-7.2 | CE7a | 15.4 | 6 | 311 | 20.2 | 6317 | 4.5 | | 156.3 |
| PC-7.3 | CE7a | 11.7 | 15 | 305 | 26.1 | 8152 | 35 | | 156.1 |
| PI-1.1 | IE1 | 10.6 | 1 | 258 | 24.4 | 6965 | | 1.6 | 149.8 |
| PI-1.2 | IE1 | 9.2 | 6 | 478 | 51.9 | 14832 | | 14.8 | 149.2 |
| PI-1.3 | IE1 | 9.1 | 15 | 646 | 70.9 | 20267 | 1.03 | | 151.3 |
| PI-2a.1 | IE2a | 12.3 | 1 | 210 | 17 | 4158 | | 5.1 | 151 |
| PI-2a.2 | IE2a | 5.9 | 6 | 257 | 43.6 | 10641 | | 69.2 | 150.6 |
| PI-2a.3 | IE2a | 7.5 | 15 | 383 | 51.1 | 12452 | 11.2 | | 150.1 |
| PI-2b.1 | IE2b | 14.4 | 1 | 205 | 14.2 | 5082 | | 3.69 | n.d. |
| PI-2b.2 | IE2b | 7.4 | 6 | 304 | 41.1 | 14662 | | 57.3 | n.d. |
| PI-2b.3 | IE2b | 6.7 | 15 | 388 | 57.9 | 20677 | 7.68 | | n.d. |

*PC- = comparative; PI- = inventive

TABLE 4b

NMR polymer microstructure characterisation results

| Pol. Example* | Catalyst | 2,1e% | mmmm% |
|---|---|---|---|
| PC-1.2 | CE1 | 0.94 | 98.96 |
| PC-2.2 | CE2 | 1.57 | 99.75 |
| PC-3.2 | CE3 | 0.41 | 99.35 |
| PC-4.2 | CE4 | 0.56 | 99.42 |
| PC-5.2 | CE5 | 0.82 | 99.15 |
| PC-6.2 | CE6 | 0.77 | 99.43 |
| PC-7.2 | CE7a | 0.47 | 99.69 |
| PI-1.2 | IE1 | 1.06 | 99.75 |
| PI-2a.2 | IE2a | 1 | 99.52 |

TABLE 5

Ethylene-propylene random copolymerisations. Polymerisation time 30 minutes. Tp = 70° C.

| Pol. example | Catalyst | Catalyst amount (mg) | C2 (g) | Yield (g) | Activity (kg-PP/g-Cat/h) | Metal activity (kg-PP/g-Zr/h) | Mw (kg/mol) | Mw/Mn | Tm (° C.) | NMR C2 (wt. %) |
|---|---|---|---|---|---|---|---|---|---|---|
| P1-1.4 | IE1 | 5.1 | 50.1 | 318 | 124.6 | 35608 | 760 | 2.6 | 119 | 4 |
| PC-2.4 | CE2 | 10 | 50 | 234 | 46.8 | 18736 | 674 | 2.5 | 115.3 | 4.4 |
| PC-5.4 | CE5 | 11.7 | 50 | 147 | 25.1 | 7160 | 227 | 2.2 | 123.2 | 3.7 |
| PC-4.4 | CE6 | 10.2 | 50 | 206 | 40.4 | 11535 | 426 | 2.7 | 114.2 | 4.3 |
| PC-4.4 | CE4 | 9.9 | 50 | 205 | 41.4 | 14798 | 277 | 2.4 | 115.7 | 4.6 |
| PI-2a.4 | IE2a | 10.3 | 50 | 491 | 95.3 | 23249 | 467 | 2.7 | 118.7 | 3.8 |
| PC-7.4 | CE7a | 11.1 | 50 | 150 | 27 | 8440 | 274 | 2.4 | 114.3 | 5.1 |

TABLE 6

Copolymerisation of propylene and 1-hexene with off-line prepolymerised catalysts., conditions. Polymerisation time 60 minutes. Tp = 75° C.

| Pol. example | Catalyst | Pre-polymerizstion | | | | | | Main polymerisation |
|---|---|---|---|---|---|---|---|---|
| | | Off-line prepolymerized catalyst amount mg | MC content in dosed off-line prepol catalyst mg | T ° C. | time min | H2 NL | C6 g | Average calculated C6/(C3) wt-% in liquid phase w % |
| PC-2.5 | CE2-p | 105 | 0.6 | 20 | 10 | 1.43 | 237 | 6.12 |
| PC-7.5 | CE7b-p | 185 | 2.1 | 20 | 10 | 1.43 | 237 | 6.18 |
| PC-8.5 | CE-8-p | 249 | 1.3 | 20 | 10 | 1.43 | 237 | 6.19 |
| P1-1.5 | IE1-p | 102 | 1.1 | 20 | 10 | 1.43 | 237 | 6.21 |
| PI-2a.4 | IE2a-p | 100 | 1.1 | 20 | 10 | 1.43 | 237 | 6.16 |
| PI-2b.5 | IE2b-p | 126 | 0.9 | 20 | 10 | 1.43 | 237 | 6.02 |

TABLE 7

Copolymerisation of propylene and 1-hexene with off-line prepolymerised catalysts, results

| Pol example | Catalyst | yield g | Catalyst Activity* kg/$g_{prep.cat}$/h | MC activity** kg/$g_{MC}$/h | $MFR_2$ g/10 min | C6 (IR) wt % | R*** | Mn kg/mol | Mw kg/mol | Mw/Mn | $T_m$ ° C. |
|---|---|---|---|---|---|---|---|---|---|---|---|
| PC-2.5 | CE2-p | 313 | 3 | 505 | 72.7 | 4.2 | 0.67 | 55 | 122 | 2.2 | 120.9 |
| PC-7.5 | CE7b-p | 540 | 2.9 | 278 | 111.9 | 4.9 | 0.78 | 54 | 112 | 2.1 | 125.5 |
| PC-8.5 | CE8-p | 439 | 1.8 | 333 | 14.7 | 4.1 | 0.65 | 76 | 180 | 2.4 | 126.9 |
| P1-1.5 | IE1-p | 631 | 6.2 | 557 | 3.7 | 5.1 | 0.81 | 72 | 156 | 2.2 | 121.9 |
| PI-2a.4 | IE2a-p | 468 | 4.7 | 437 | 38.8 | 5.2 | 0.84 | 66 | 144 | 2.2 | 121.5 |
| PI-2b.5 | IE2b-p | 530 | 4.2 | 592 | 41.1 | 5.4 | 0.86 | 112 | 246 | 2.2 | 120.6 |

*activity based on the amount of off-line prepolymerised catalyst
**activity based on the metallocene amount
***R is the relative reactivity ratio of the two monomers for the given catalyst system defined by:
R = (ratio C6/C3 w/w in polymer)/(ratio C6/C3 w/w in liquid phase)

Below a summary of properties of catalysts of the examples. Comparing especially of metallocenes 1E2 and CE7, which differ only in the 3,5 substituents of the phenyl ring at 4 position of the indenyl, show clearly the benefits of the metallocenes of the present invention.

TABLE 8

Summary of properties of catalysts of the examples

| | hPP 15 mmol H2 Activity kg-PP/g-Cat/h | hPP 15 mmol H2 Tm ° C. | C2/C3 Activity kg-PP/g-Cat/h | C6/C3-p Activity kg-PP/g-prepcat/h | C6/C3-p R*** |
|---|---|---|---|---|---|
| IE1 | 70.9 | 151.3 | 124.6 | 6.2 | 0.81 |
| IE2a | 51.1 | 150.1 | 95.3 | 4.7 | 0.84 |
| IE2b | 57.9 | n.d | | 4.2 | 0.86 |
| CE1 | 11.7 | 149.9 | | | |
| CE2 | 53.1 | 144.0 | 46.8 | 3.0 | 0.67 |
| CE3 | 20.4 | 156.6 | | | |
| CE4 | 17.3 | 155.3 | 41.4 | | |
| CE5 | 26.3 | 151.8 | 25.1 | | |
| CE6 | 26.2 | 152.5 | 40.4 | | |
| CE7a | 26.1 | 156.1 | 27.0 | | |
| CE7b | | | | 2.9 | 0.78 |
| CE8 | | | | 1.8 | 0.65 |

***R is the relative reactivity ratio of the two monomers for the given catalyst system defined by: R = (ratio C6/C3 w/w in polymer)/(ratio C6/C3 w/w in liquid phase)

Catalyst Preparation Examples—Supported on Carrier

The silica-MAO catalysts have been prepared on 30μ SUNSPERA DM-L-303 silica produced by AGC Si-Tech Co, additionally calcined at 600° C. for 2 hours under air.

Step 1—Preparation of Silica-MAO

Toluene was dried over molecular sieves and degassed by bubbling with argon for at least 30 minutes. Inside the glovebox, 10 g of the calcined silica was charged into a round-bottom flask equipped with an overhead stirrer and a sealed septum, and then ~50 mL of dry and degassed toluene was added into it. The resulting suspension was cooled down to 0° C. under mild stirring (200-300 rpm) and 25 mL of MAO solution added dropwise. After around 60 minutes, the cooling bath was removed and stirring was continued for 2 hours. The silica-MAO slurry was allowed to settle and then the supernatant toluene solution was siphoned off via a 2/4 teflon tube. Then, around 30 mL of dried and degassed toluene was added and the slurry was stirred for 15 minutes at room temperature.

The flask was placed into the oil bath and warmed up to 80° C. and the slurry solution was stirred for additional 15 min. Then the silica-MAO slurry was again allowed to settle for 10 min. The hot toluene solution was siphoned off.

This washing procedure was repeated one more time, and then an additional washing has been performed using pentane (30 ml pentane, stirring 15 min, settling 10 min). The pentane layer was siphoned off, then the solid was dried under argon flow at for about 3 h and at 50° C. The white flowing MAO-silica powder was collected and used for all supported catalyst preparations.

IE-3 Preparation of Supported Metallocene Catalyst Based on MC-IE1 (Inventive)

Inside the glove box, 0.25 mL of MAO solution was added to MC-IE1 solution (32 mg of MC-IE1 in 1 ml of toluene) in a septum bottle.

1 g of dry silica-MAO powder was placed into a 20 mL glass vial, and the complex solution was added. The resulting slurry was allowed to stand overnight in the glove box. Then 5 mL of dried and degassed toluene was added; the bath temperature was set to 60° C. and stirred for 30 minutes. The solid catalyst was allowed to settle, and then the toluene layer was removed. The washing step was repeated twice more (2×5 mL toluene).

Then an additional washing step has been performed at room temperature using 5 ml of dry pentane. The slurry solution was stirred gently for 30 min. The pentane layer was siphoned off and then the solid was dried under argon flow at room temperature for 3 h. 1 g of a red silica supported flowing powder was collected.

IE-4 Preparation of Supported Metallocene Catalysts Based on MC-IE4 (Inventive)

Preparation was carried out as for catalyst Example IE-3, but using 33 mg of metallocene MC-IE4

CE-9 Preparation of Supported Metallocene Catalyst Based on MC-CE9 (Comparison)

Preparation was carried out as for catalyst Example IE-3 but using 32 mg of metallocene MC-CE9

CE-10 Preparation of Metallocene Catalyst Based on MC-CE10

Preparation was carried out as for catalyst Example IE-3 but using 30 mg of metallocene MC-CE10

The available composition data of the catalysts from ICP are listed in Table 9.

TABLE 9

Composition data of the catalysts used in this investigation

| Catalyst | MC | Zr (wt %) | Al (wt %) | Al/Zr (molar) | MC (wt %) |
|---|---|---|---|---|---|
| SiO$_2$/MAO-MC-CE9 | MC-CE9 | 0.20 | 14.8 | 250 | 1.69 |
| SiO$_2$/MAO-MC-CE10 | MC-CE10 | 0.18 | 14.8 | 280 | 1.63 |
| SiO$_2$/MAO-MC-IE1 | MC-IE1 | 0.18 | 15.4 | 290 | 1.69 |
| SiO$_2$/MAO-MC-IE4 | MC-IE4 | 0.19 | 15.6 | 280 | 2.02 |

Polymerisation Procedure for 2-Step Propylene Homopolymerisation (hPP) in Bulk+Gas Phase Experiments Step 1: Prepolymerisation and Bulk Homopolymerisation A 20.9 L stainless-steel reactor containing 0.4 bar-g propylene was filled with 3950 g propylene. Triethylaluminum (0.80 ml of a 0.62 mol/1 solution in heptane) was placed into a stainless steel vial and injected into the reactor by means of a flow of 240 g propylene. 2.0 NL of H2 was added via mass flow controller in one minute. The solution was stirred at 20° C. and 250 rpm for at least 20 min. The catalyst was injected as described in the following. The desired amount of solid, prepolymerised catalyst was loaded into a 5 ml stainless steel vial inside a glovebox and a second 5 ml vial containing 4 ml n-heptane pressurized with 10 bars of nitrogen was added on top of the first vial. This catalyst feeder system was mounted on a port on the lid of the reactor, the valve between the two vials was opened and the solid catalyst was contacted with heptane under nitrogen pressure for 2 s, and then flushed into the reactor with 240 g propylene. The prepolymerisation was run for 10 min. At the end of the prepolymerisation step the temperature was raised to 80° C. The reactor temperature was held constant at 80° C. throughout the polymerisation. The liquid propylene polymerisation was run for 40 minutes. The polymerisation time was measured starting when the internal reactor temperature reached 2° C. below the set polymerisation temperature.

Step 2: Gas Phase Homopolymerisation

After the bulk step was completed, the stirrer speed was reduced to 50 rpm and the pressure was reduced to 23.5 bar-g by venting the monomer. Afterwards the stirrer speed was set to 180 rpm, the reactor pressure was set at 24 bar-g while keeping the reactor temperature at 80° C., and 2.0 NL hydrogen were added via flow controller in 4 minutes. The gas phase homopolymerisation was run for 60 minutes, while keeping the pressure constant by feeding propylene via mass flow controller and the temperature constant at 80° C. by thermostat.

POLYMERISATION RESULTS

The 2-step hPP in bulk+gas phase polymerisation results with the silica/MAO catalysts based on the 30μ Sunspera silica and metallocenes MC-CE9, MC-CE10, MC-IE1 and MC-IE4 are listed in 10 and 11.

Operability and morphology were very good for all homopolymerisation experiments: no reactor fouling, no fines and no agglomerated particles could be observed. Bulk density was always high (0.45 to 0.49 g/cc). Xylene solubles are below 0.5 wt %, as typical of hPP from metallocene catalysts.

Kinetic profiles are stable for all catalysts in both the bulk and the gas phase steps, indicating that these silica catalysts have a kinetic profile compatible with the loop+gas phase reactor sequences of industrial polypropylene processes.

Given the different chemical compositions of the catalysts, productivities have been compared based on their metallocene content.

TABLE 10

2-step homopolymerisation experiments:
Prepolymerisation 10 min, all H2 fed before catalyst injection;
bulk step at 80° C., 40 min; gas phase step at 80° C., 24 bar-g, 60 min.

| Experiment # | Catalyst Amount Mg | MC amount in catalyst mg | Time from 20° C. to 80° C. min | Time from bulk to GP min | C3 fed in GP (MFC) g | total yield g | Overall productivity $kg/g_{cat}$ | overall productivity $kg/g_{MC}$ | Bulk split wt % | GP1 split wt % | MFR2 g/10 min | Powder bulk density $g/cm^3$ |
|---|---|---|---|---|---|---|---|---|---|---|---|---|
| CE-9  | 113 | 1.91 | 18 | 11 | 495 | 2158 | 19 | 1130 | 77 | 23 | 1.9 | 0.49 |
| CE-10 | 79  | 1.29 | 18 | 15 | 364 | 1585 | 20 | 1231 | 77 | 23 | 2.6 | 0.47 |
| IE-3  | 62  | 1.05 | 15 | 5  | 574 | 2145 | 35 | 2047 | 73 | 27 | 1.8 | 0.47 |
| IE-4  | 46  | 0.93 | 19 | 22 | 430 | 2021 | 44 | 2175 | 79 | 21 | 6.1 | 0.46 |

TABLE 11

2-step homopolymers: analytics

| Experiment # | XS wt % | $T_m$ ° C. | $M_w$ g/mol | $M_w/M_n$ |
|---|---|---|---|---|
| CE-9  | 0.4 | 150 | 335000 | 3.5 |
| CE-10 | 0.2 | 151 | 311500 | 3.5 |
| IE-3  | 0.5 | 151 | 390000 | 4.3 |
| IE-4  | 0.2 | 152 | 284000 | 4.6 |

The invention claimed is:

1. A complex of formula (II)

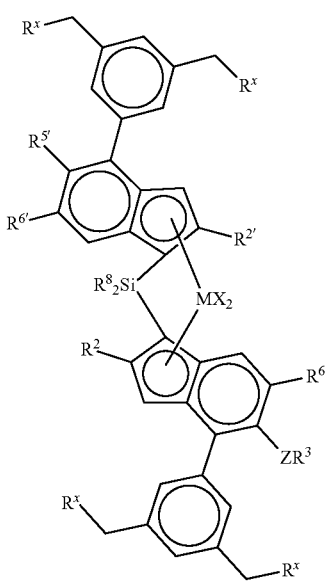

(II)

wherein
M is zirconium or hafnium;
each X is independently a hydrogen atom, a halogen atom, a $C_{1-6}$ alkoxy group, a $C_{1-6}$ alkyl group, a phenyl group, or a benzyl group;
$R^2$ and $R^{2'}$ are each independently a $C_1$-$C_{10}$ alkyl group;
$R^{5'}$ is hydrogen or $ZR^{3'}$;
Z is O or S;
$R^3$ and $R^{3'}$ are each independently a $C_{1-10}$ linear or branched alkyl, $C_{2-10}$ alkenyl, $C_{3-10}$ cycloalkyl, $C_{3-10}$ cycloalkenyl, $C_{6-10}$ aryl, $C_{7-10}$ alkylaryl, or $C_{7-10}$ arylalkyl group, optionally substituted by one or more halo groups;
$R^6$ and $R^{6'}$ are each independently a $C_{1-10}$ alkyl group or a $C_{6-10}$ aryl group;
each $R^8$ is independently a $C_{1-20}$ hydrocarbyl group or wherein two $R^8$ groups taken together with the atoms to which they are attached form a ring; and
each $R^x$ is independently H or a $C_{1-10}$ alkyl group.

2. The complex as claimed in claim 1, wherein $R^2$ and $R^{2'}$ are independently a linear or branched $C_{1-6}$ alkyl group.

3. The complex as claimed in claim 1, wherein $R^6$ and $R^{6'}$ are independently a linear or branched $C_{1-10}$ alkyl group.

4. The complex as claimed in claim 1, wherein $R^6$ is a branched $C_{3-8}$ alkyl group, and $R^{6'}$ is a linear $C_{1-8}$ alkyl group or branched $C_{3-8}$ alkyl group.

5. The complex as claimed in claim 1, wherein:
$R^3$ is a $C_{1-6}$ alkyl group; and
$R^{3'}$ is a $C_{1-6}$ alkyl group.

6. The complex as claimed in claim 1, wherein each $R^x$ is H or $C_{1-6}$ alkyl.

7. The complex as claimed in claim 1, wherein said complex is of formula (IIIa) or formula (IIIb):

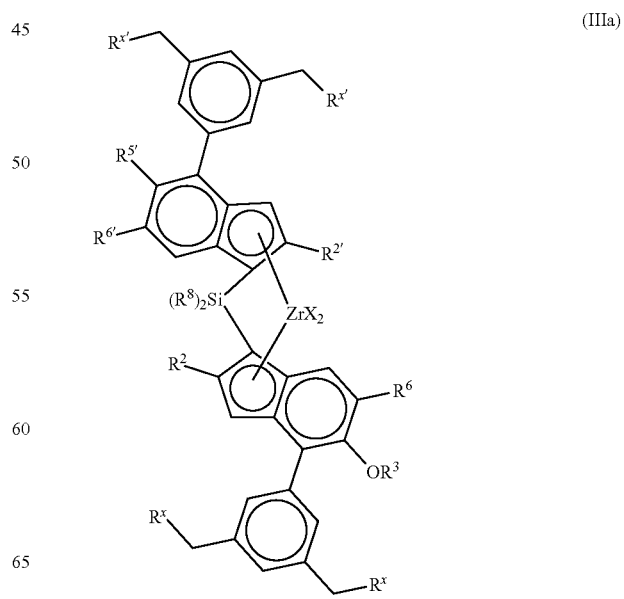

(IIIa)

-continued (IIIb)

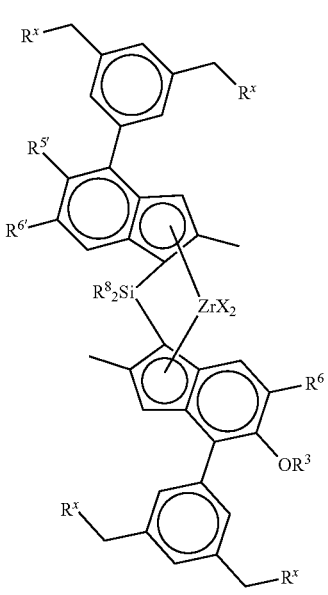

wherein each $R^8$ is independently a $C_{1-6}$ alkyl group or $C_{3-7}$ cycloalkyl group;

$R^6$ is a $C_{1-10}$ alkyl group;

$R^{6'}$ is a $C_{1-10}$ alkyl group;

$R^{5'}$ is hydrogen or $OR^3$; and $R^2$ and $R^{2'}$ are independently a $C_{1-6}$ alkyl.

8. The complex as claimed in claim 1, wherein said complex is of formula (IVa) or formula (IVb):

(IVa)

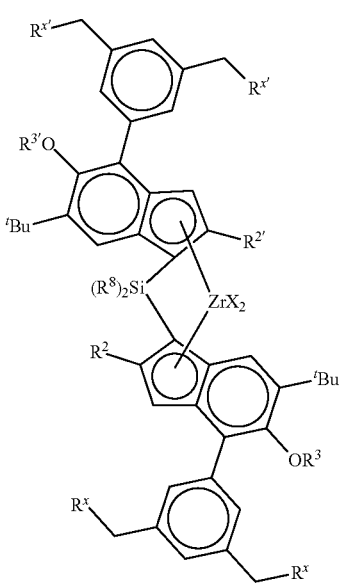

-continued (IVb)

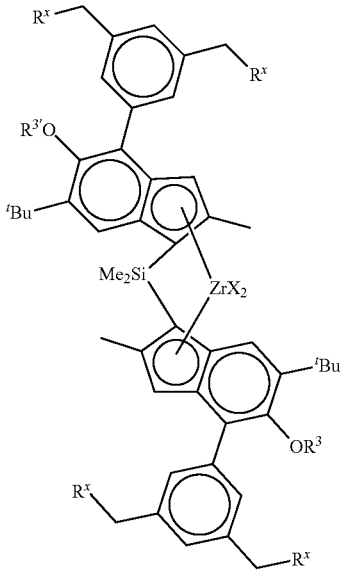

wherein each $R^x$ is independently H or a $C_{1-4}$ alkyl group.

9. The complex as claimed in claim 1, wherein said complex is of formula (V):

(V)

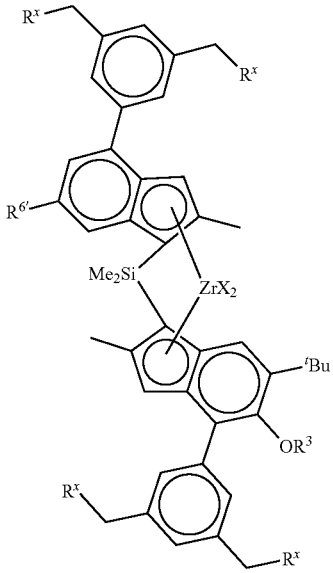

wherein each $R^x$ is independently H or methyl; and $R^{6'}$ is a linear or branched $C_{1-4}$ hydrocarbyl group.

10. The complex as claimed in claim 1, wherein the complex is symmetrical.

11. The complex as claimed in claim 1, wherein the complex is of formula

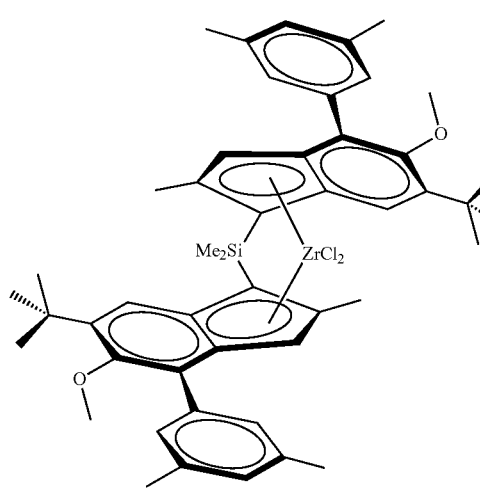

rac-Me$_2$Si(2-Me-4-(3,5-Me$_2$Ph)-5-OMe-6-tBu-Ind)$_2$ZrCl$_2$

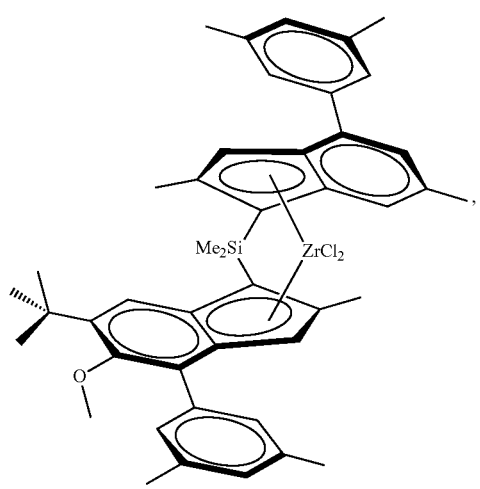

rac-anti-Me$_2$Si(2,6-Me$_2$-4-(3,5-Me$_2$Ph)Ind)(2-Me-4-(3,5-Me$_2$Ph)-5-OMe-6-tBu-Ind)ZrCl$_2$

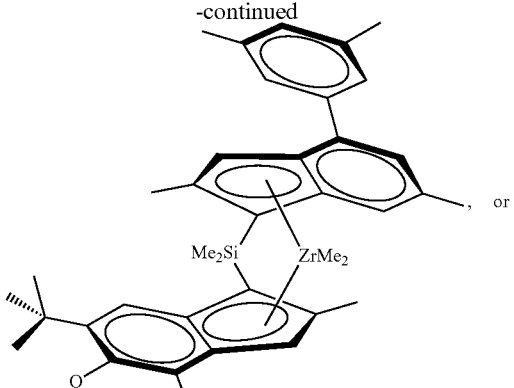

rac-anti-Me$_2$Si(2,6-Me$_2$-4-(3,5-Me$_2$Ph)Ind)(2-Me-4-(3,5-Me$_2$Ph)-5-OMe-6-tBu-Ind)ZrMe$_2$

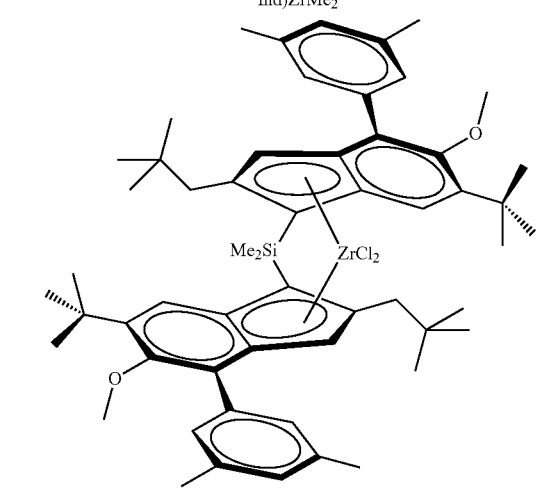

rac-Me$_2$Si(2-neopentyl-4-(3',5'-Me$_2$Ph)-5-OMe-6-tBu-Ind)$_2$ZrCl$_2$

12. A catalyst comprising
   (i) the complex as claimed in claim 1; and
   (ii) a cocatalyst comprising a compound of a group 13 metal.

13. The catalyst of claim 12, wherein the catalyst is a solid catalyst.

14. A process for the manufacture of the catalyst as claimed in claim 12, the process comprising:
   forming a liquid/liquid emulsion system, which comprises a solution of catalyst components (i) and (ii) dispersed in a solvent so as to form dispersed droplets, and
   solidifying said dispersed droplets to form solid particles.

15. The catalyst of claim 12, wherein the catalyst is supported on silica.

16. A process for the polymerization of at least one olefin, the process comprising reacting said at least one olefin with the catalyst as claimed in claim 12.

* * * * *